(12) United States Patent
Iwamura et al.

(10) Patent No.: US 10,392,345 B2
(45) Date of Patent: *Aug. 27, 2019

(54) CRYSTAL OF SALT OF NOVEL 3-AZABICYCLO[3.1.0]HEXANE DERIVATIVE AND PHARMACEUTICAL USE THEREOF

(71) Applicants: SANWA KAGAKU KENKYUSHO CO., LTD., Nagoya-shi, Aichi (JP); UBE INDUSTRIES, LTD., Ube-shi, Yamaguchi (JP)

(72) Inventors: Ryo Iwamura, Ube (JP); Yasunori Tsuzaki, Ube (JP); Hiroyuki Setoguchi, Ube (JP); Hiroto Akaza, Ube (JP); Yasuhito Yamamoto, Ube (JP); Akira Takama, Ube (JP); Yuka Kuno, Nagoya (JP)

(73) Assignees: SANWA KAGAKU KENKYUSHO CO., LTD., Aichi (JP); UBE INDUSTRIES, LTD., Yamaguchi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/575,188

(22) PCT Filed: May 19, 2016

(86) PCT No.: PCT/JP2016/064942
§ 371 (c)(1),
(2) Date: Nov. 17, 2017

(87) PCT Pub. No.: WO2016/186184
PCT Pub. Date: Nov. 24, 2016

(65) Prior Publication Data
US 2018/0148409 A1 May 31, 2018

(30) Foreign Application Priority Data

May 20, 2015 (JP) ................................ 2015-103161

(51) Int. Cl.
*C07D 209/52* (2006.01)
*A61K 31/403* (2006.01)
*A61P 25/36* (2006.01)

(52) U.S. Cl.
CPC .......... *C07D 209/52* (2013.01); *A61K 31/403* (2013.01); *A61P 25/36* (2018.01); *C07B 2200/13* (2013.01)

(58) Field of Classification Search
CPC .................................................. C07D 209/52
See application file for complete search history.

(56) References Cited

U.S. PATENT DOCUMENTS 6,313,312 B1 11/2001 Banks et al.
2002/0025948 A1 2/2002 Banks et al.
(Continued)

FOREIGN PATENT DOCUMENTS

WO 00039089 A1 7/2000
WO 01098267 A1 12/2001
(Continued)

OTHER PUBLICATIONS

Pandit "Introduction to the pharmaceutical sciences" 2006, Lippincott, Williams and Wilkins: Baltimore, p. 19.*
(Continued)

*Primary Examiner* — David K O'Dell
(74) *Attorney, Agent, or Firm* — Cantor Colburn LLP

(57) ABSTRACT

Disclosed herein are a crystal comprising a compound, which has μ-opioid receptor antagonistic action, few side effects, and high safety, and having high purity and excellent physical properties (stability, solubility, etc.), and a method for producing the crystal.

The crystal is a crystal of a salt comprising: a compound represented by a formula (I)

[Chemical Formula 1]

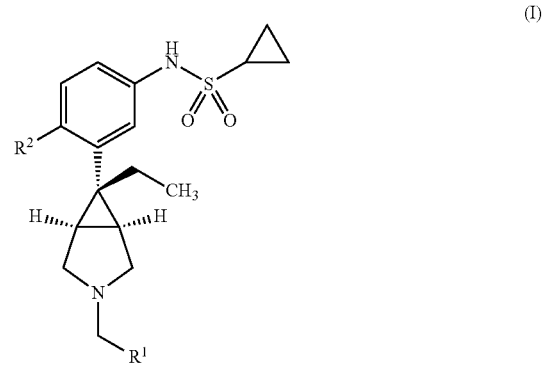

(I)

[wherein $R^2$ is a hydrogen atom or a halogen atom, and $R^1$ is a group selected from the group consisting of

[Chemical Formula 2]

(Continued)

-continued

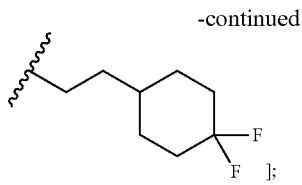

and an acid selected from the group consisting of hydrochloric acid, hydrobromic acid, and oxalic acid, or a hydrate thereof.

26 Claims, 16 Drawing Sheets

(56) References Cited

U.S. PATENT DOCUMENTS

| | | |
|---|---|---|
| 2002/0072616 A1 | 6/2002 | Banks et al. |
| 2003/0087898 A1 | 5/2003 | McHardy et al. |
| 2005/0043327 A1 | 2/2005 | Coe et al. |
| 2005/0043345 A1 | 2/2005 | Coe et al. |
| 2005/0075387 A1 | 4/2005 | Tickner et al. |
| 2005/0113437 A1 | 5/2005 | McHardy et al. |
| 2016/0280645 A1 | 11/2016 | Taniko et al. |

FOREIGN PATENT DOCUMENTS

| | | |
|---|---|---|
| WO | 03035622 A1 | 5/2003 |
| WO | 2005018645 A1 | 3/2005 |
| WO | 2005018670 A1 | 3/2005 |
| WO | 2005033080 A1 | 4/2005 |
| WO | 2005037790 A1 | 4/2005 |
| WO | 2008075162 A2 | 6/2008 |
| WO | 2015076310 A1 | 5/2015 |

OTHER PUBLICATIONS

Stahl "Handbook of Pharmaceutical Salts: Properties Selection and Use" Verlag Helvetica Chinnica Acta: 2002, pp. 118-121 220-235, 288-289, 300-301.*
Paulekuhn "Trends in Active Pharmaceutical Ingredient Salt Selection based on Analysis of the Orange Book Database" Journal of Medicinal Chemistry 2007, 50, 6665-6672.*
Gonzalez, J. P. and Brogden, R. N. "Naltrexone: A Review of its Pharmacodynamic and Pharmacokinetic Properties and Therapeutic Efficacy in the Management of Opioid Dependence" Drugs vol. 35, pp. 192-213 (1988).
International Search Report for International Application No. PCT/JP2016/064942, dated Jul. 26, 2016, 5 pages.
Lunn, G., et al., "SAR and Biological evaluation of 3-azabicyclo[3.1.0]hexane derivatives as μ opioid ligands" Bioorganic & Medicinal Chemistry Letters, vol. 22 (2012) pp. 2200-2203.
Lunn. G., et al. "Discovery and synthesis of a new class of opioid ligand having a 3-azabicyclo[3.1.0]hexane core. An example of a 'magic methyl' giving a 35-fold improvement in binding" Bioorganic & Medicinal Chemistry Letters 21 (2011) 4608-4611.
McHardy, S. F., et al. "Discovery of CP-866,087, a mu opioid receptor antagonist for the treatment of alcohol abuse and dependence" Med. Chem. Commun., 2011, 2, 1001.

* cited by examiner

[FIG. 1]
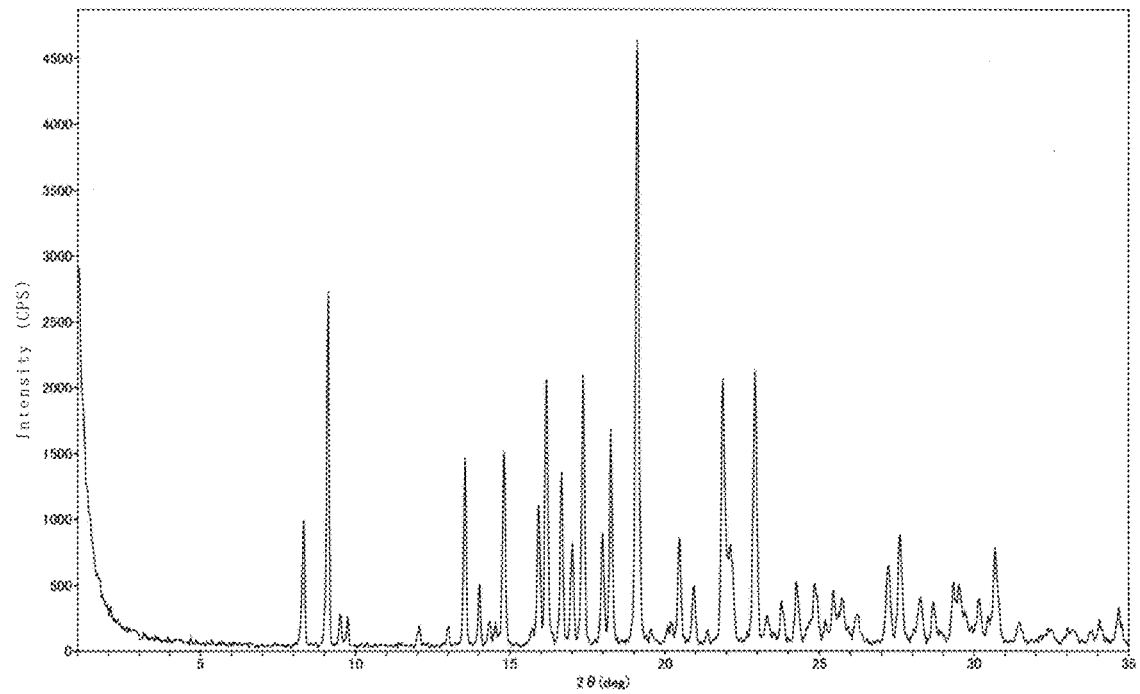
| 2θ (°) | d-spacing (Å) | 2θ (°) | d-spacing (Å) | 2θ (°) | d-spacing (Å) | 2θ (°) | d-spacing (Å) |
|---|---|---|---|---|---|---|---|
| 8.335 | 10.5997 | 17.019 | 5.2055 | 23.554 | 3.7741 | 29.342 | 3.0415 |
| 9.119 | 9.6902 | 17.363 | 5.1032 | 23.782 | 3.7384 | 29.521 | 3.0234 |
| 9.513 | 9.2890 | 17.998 | 4.9246 | 24.263 | 3.6653 | 29.701 | 3.0055 |
| 9.742 | 9.0717 | 18.260 | 4.8544 | 24.683 | 3.6039 | 29.919 | 2.9840 |
| 12.059 | 7.3334 | 19.118 | 4.6385 | 24.844 | 3.5810 | 30.161 | 2.9607 |
| 13.015 | 6.7966 | 19.543 | 4.5387 | 25.202 | 3.5308 | 30.461 | 2.9322 |
| 13.563 | 6.5234 | 20.100 | 4.4142 | 25.459 | 3.4958 | 30.698 | 2.9101 |
| 14.024 | 6.3101 | 20.204 | 4.3916 | 25.723 | 3.4605 | 31.459 | 2.8414 |
| 14.357 | 6.1644 | 20.480 | 4.3330 | 26.238 | 3.3938 | 32.159 | 2.7811 |
| 14.541 | 6.0867 | 20.956 | 4.2357 | 27.220 | 3.2735 | 32.419 | 2.7594 |
| 14.818 | 5.9733 | 21.394 | 4.1501 | 27.600 | 3.2293 | 33.037 | 2.7092 |
| 15.720 | 5.6328 | 21.882 | 4.0585 | 28.047 | 3.1788 | 33.239 | 2.6932 |
| 15.938 | 5.5562 | 22.120 | 4.0154 | 28.277 | 3.1535 | 33.833 | 2.6473 |
| 16.195 | 5.4684 | 22.939 | 3.8738 | 28.681 | 3.1100 | 34.064 | 2.6299 |
| 16.677 | 5.3115 | 23.319 | 3.8115 | 28.901 | 3.0868 | 34.680 | 2.5845 |

[FIG. 2]
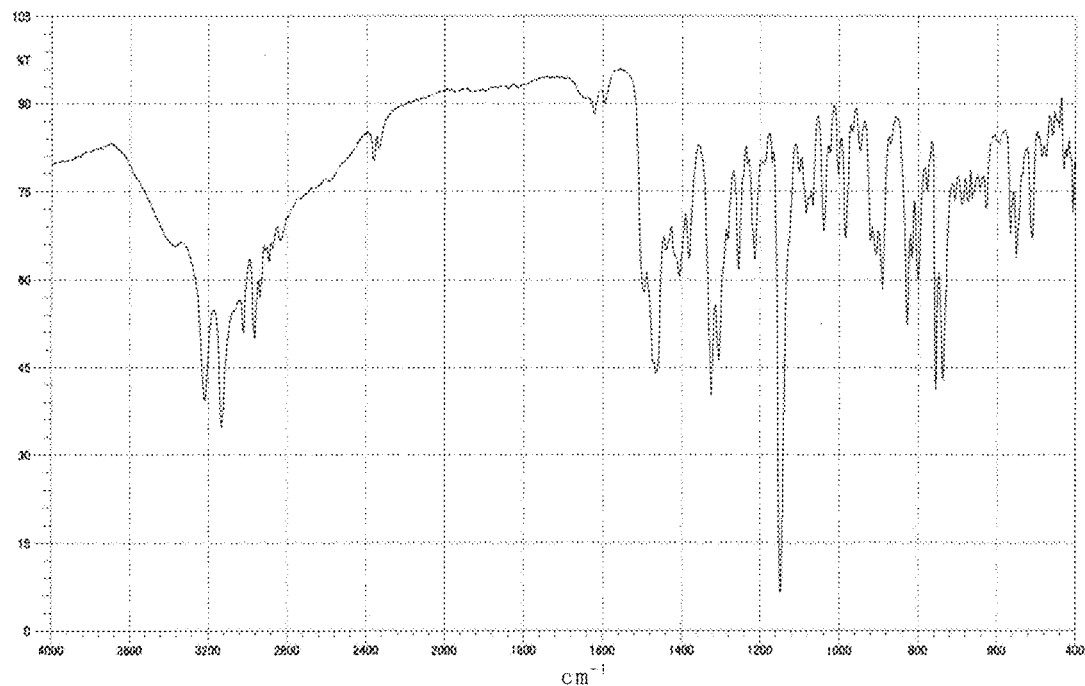
| peak (cm⁻¹) | peak (cm⁻¹) | peak (cm⁻¹) | peak (cm⁻¹) |
|---|---|---|---|
| 406.98 | 688.59 | 1022.27 | 1406.11 |
| 422.41 | 707.88 | 1039.63 | 1438.90 |
| 430.13 | 736.81 | 1066.64 | 1465.90 |
| 441.70 | 756.10 | 1076.28 | 1494.83 |
| 447.49 | 777.31 | 1083.99 | 1595.13 |
| 457.13 | 800.46 | 1101.35 | 1622.13 |
| 474.49 | 815.89 | 1149.57 | 2833.43 |
| 484.13 | 827.46 | 1168.86 | 2873.94 |
| 493.78 | 869.90 | 1190.08 | 2891.30 |
| 509.21 | 891.11 | 1213.23 | 2908.65 |
| 549.71 | 906.54 | 1232.51 | 2939.52 |
| 565.14 | 920.05 | 1253.73 | 2964.59 |
| 628.79 | 947.05 | 1282.66 | 3022.45 |
| 642.30 | 966.34 | 1303.88 | 3132.40 |
| 663.51 | 983.70 | 1325.10 | 3219.19 |
| 675.09 | 1002.98 | 1381.03 | 3371.57 |

[FIG. 3]
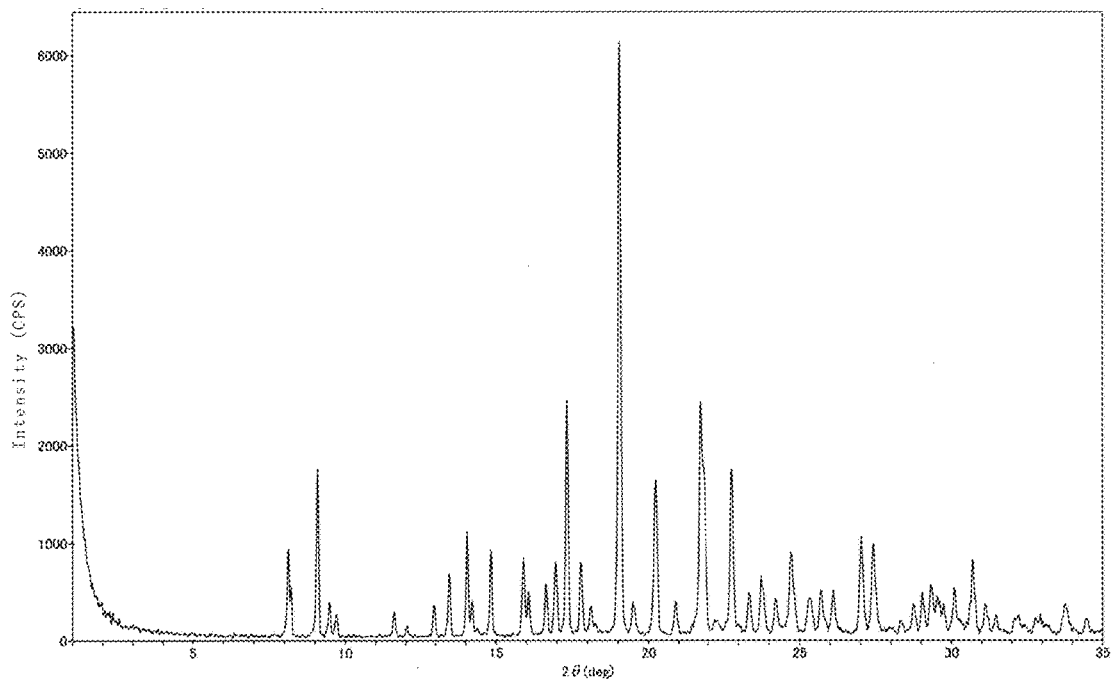
| 2θ (°) | d-spacing (Å) | 2θ (°) | d-spacing (Å) | 2θ (°) | d-spacing (Å) | 2θ (°) | d-spacing (Å) |
|---|---|---|---|---|---|---|---|
| 8.137 | 10.8576 | 16.641 | 5.3231 | 24.221 | 3.6716 | 30.296 | 2.9478 |
| 8.216 | 10.7522 | 16.961 | 5.2232 | 24.721 | 3.5984 | 30.703 | 2.9096 |
| 9.100 | 9.7099 | 17.337 | 5.1109 | 25.340 | 3.5119 | 31.121 | 2.8715 |
| 9.485 | 9.3166 | 17.797 | 4.9799 | 25.701 | 3.4634 | 31.497 | 2.8381 |
| 9.717 | 9.0951 | 18.117 | 4.8924 | 26.118 | 3.4090 | 31.709 | 2.8196 |
| 11.618 | 7.6110 | 18.260 | 4.8544 | 27.039 | 3.2950 | 32.103 | 2.7859 |
| 12.038 | 7.3461 | 19.059 | 4.6529 | 27.421 | 3.2500 | 32.221 | 2.7759 |
| 12.959 | 6.8260 | 19.501 | 4.5483 | 27.962 | 3.1884 | 32.397 | 2.7612 |
| 13.461 | 6.5726 | 20.241 | 4.3837 | 28.310 | 3.1499 | 32.784 | 2.7295 |
| 14.057 | 6.2953 | 20.901 | 4.2467 | 28.742 | 3.1035 | 32.942 | 2.7168 |
| 14.217 | 6.2249 | 21.740 | 4.0847 | 29.041 | 3.0723 | 33.218 | 2.6948 |
| 14.382 | 6.1535 | 22.222 | 3.9972 | 29.322 | 3.0434 | 33.761 | 2.6527 |
| 14.839 | 5.9650 | 22.778 | 3.9008 | 29.540 | 3.0215 | 34.055 | 2.6305 |
| 15.900 | 5.5692 | 23.343 | 3.8076 | 29.740 | 3.0017 | 34.462 | 2.6004 |
| 16.062 | 5.5135 | 23.744 | 3.7443 | 30.101 | 2.9665 | | |

[FIG. 4]
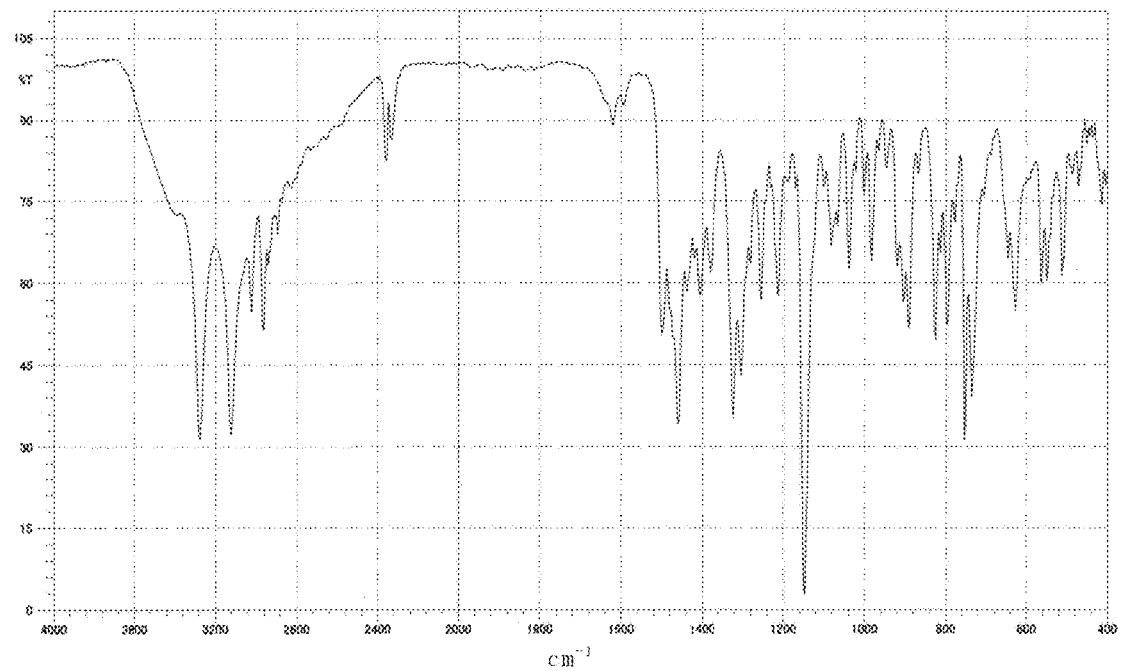
| peak (cm⁻¹) | peak (cm⁻¹) | peak (cm⁻¹) | peak (cm⁻¹) |
|---|---|---|---|
| 405.05 | 754.17 | 1037.70 | 1421.54 |
| 414.70 | 779.24 | 1066.64 | 1438.90 |
| 437.84 | 796.60 | 1082.07 | 1460.11 |
| 445.56 | 813.96 | 1101.35 | 1500.62 |
| 451.34 | 825.53 | 1147.65 | 1595.13 |
| 472.56 | 867.97 | 1170.79 | 1622.13 |
| 487.99 | 891.11 | 1190.08 | 2893.22 |
| 513.07 | 904.61 | 1213.23 | 2931.80 |
| 549.71 | 920.05 | 1255.66 | 2941.44 |
| 563.21 | 947.05 | 1280.73 | 2964.59 |
| 626.87 | 966.34 | 1303.88 | 3022.45 |
| 646.15 | 983.70 | 1323.17 | 3122.75 |
| 705.95 | 1001.06 | 1381.03 | 3277.06 |
| 736.81 | 1022.27 | 1406.11 | |

[FIG. 5]
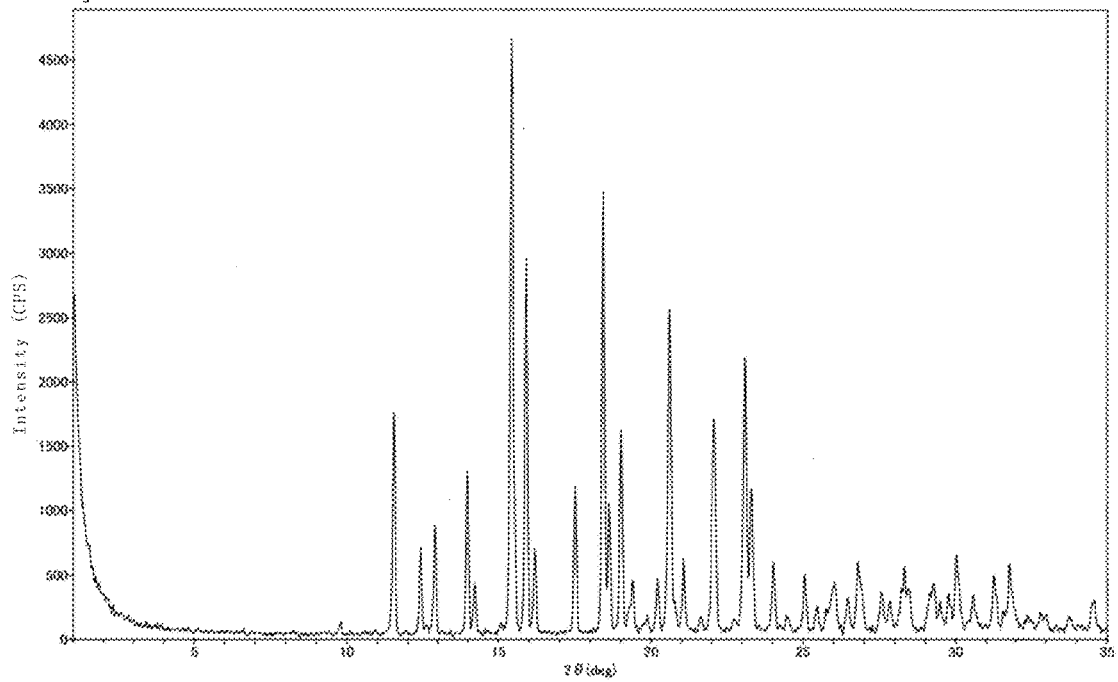
| 2θ (°) | d-spacing (Å) | 2θ (°) | d-spacing (Å) | 2θ (°) | d-spacing (Å) | 2θ (°) | d-spacing (Å) |
|---|---|---|---|---|---|---|---|
| 9.810 | 9.0087 | 19.021 | 4.6620 | 25.460 | 3.4957 | 30.040 | 2.9723 |
| 10.938 | 8.0820 | 19.384 | 4.5754 | 25.763 | 3.4553 | 30.579 | 2.9211 |
| 11.555 | 7.6518 | 19.877 | 4.4632 | 26.038 | 3.4193 | 31.278 | 2.8574 |
| 12.439 | 7.1103 | 20.204 | 4.3916 | 26.462 | 3.3656 | 31.591 | 2.8299 |
| 12.917 | 6.8482 | 20.603 | 4.3074 | 26.801 | 3.3237 | 31.803 | 2.8114 |
| 13.982 | 6.3290 | 21.061 | 4.2148 | 27.565 | 3.2333 | 32.403 | 2.7607 |
| 14.222 | 6.2226 | 21.638 | 4.1037 | 27.842 | 3.2018 | 32.842 | 2.7248 |
| 15.098 | 5.8632 | 22.080 | 4.0225 | 28.224 | 3.1593 | 33.001 | 2.7121 |
| 15.440 | 5.7341 | 22.744 | 3.9065 | 28.321 | 3.1487 | 33.760 | 2.6528 |
| 15.920 | 5.5625 | 23.103 | 3.8467 | 28.477 | 3.1318 | 34.157 | 2.6229 |
| 16.201 | 5.4666 | 23.321 | 3.8113 | 29.161 | 3.0599 | 34.577 | 2.5920 |
| 17.518 | 5.0584 | 24.039 | 3.6989 | 29.280 | 3.0478 | | |
| 18.438 | 4.8080 | 24.467 | 3.6352 | 29.482 | 3.0273 | | |
| 18.623 | 4.7607 | 25.060 | 3.5505 | 29.779 | 2.9978 | | |

[FIG. 6]
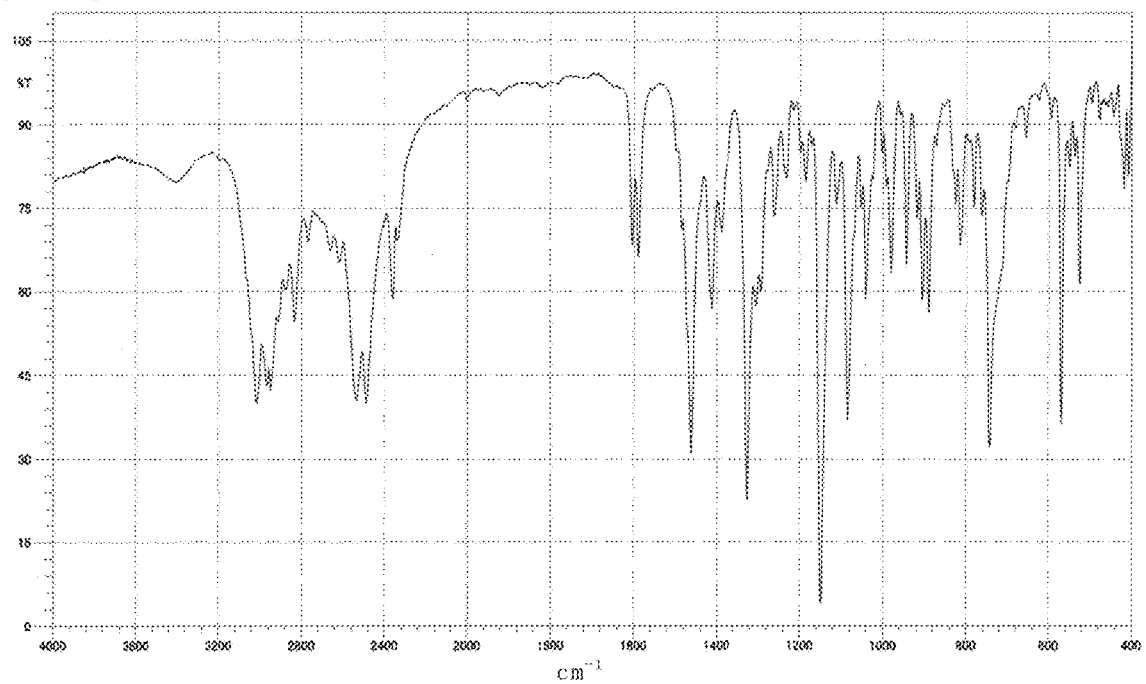
| peak (cm⁻¹) | peak (cm⁻¹) | peak (cm⁻¹) | peak (cm⁻¹) |
|---|---|---|---|
| 408.91 | 761.88 | 1111.00 | 1589.34 |
| 418.55 | 781.17 | 1149.57 | 1602.85 |
| 428.20 | 813.96 | 1184.29 | 2339.65 |
| 443.63 | 825.53 | 1197.79 | 2362.80 |
| 457.13 | 871.82 | 1215.15 | 2488.17 |
| 462.92 | 889.18 | 1232.51 | 2536.39 |
| 470.63 | 904.61 | 1261.45 | 2619.33 |
| 476.42 | 918.12 | 1276.88 | 2661.77 |
| 495.71 | 943.19 | 1292.31 | 2767.85 |
| 524.64 | 958.62 | 1305.81 | 2833.43 |
| 538.14 | 979.84 | 1325.10 | 2873.94 |
| 549.71 | 991.41 | 1388.75 | 2912.51 |
| 569.00 | 1002.98 | 1411.89 | 2949.16 |
| 594.08 | 1041.56 | 1462.04 | 2964.59 |
| 653.87 | 1053.13 | 1485.19 | 3016.67 |
| 742.59 | 1083.99 | 1498.69 | 3404.36 |

[FIG. 7]
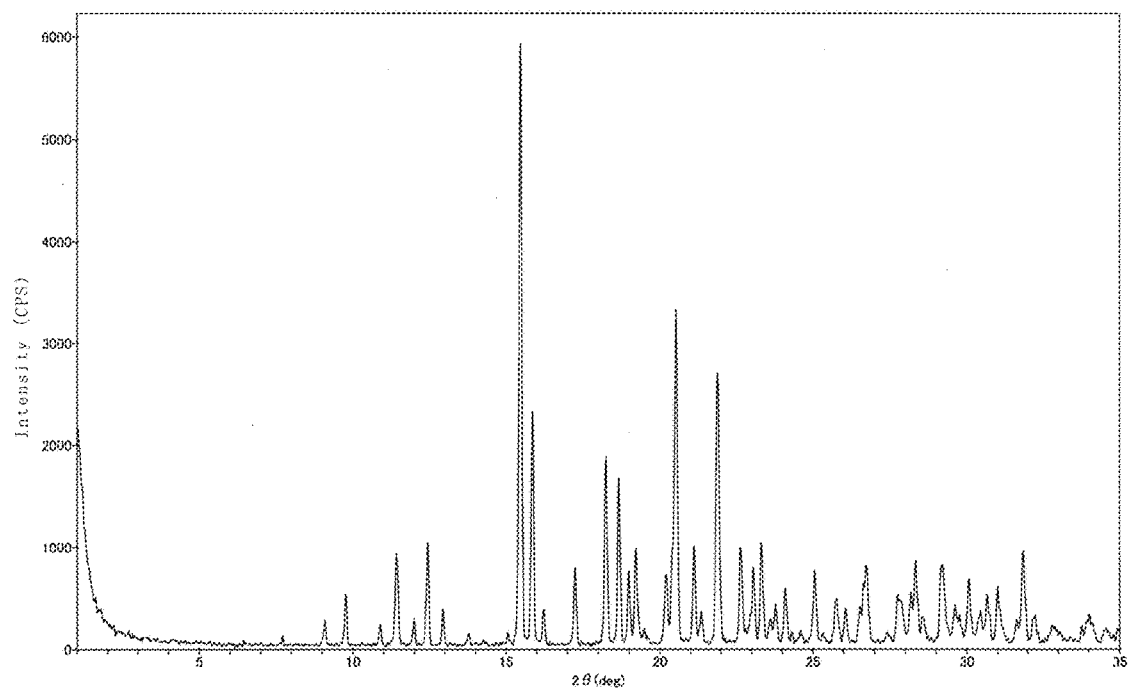
| 2θ (°) | d-spacing (Å) | 2θ (°) | d-spacing (Å) | 2θ (°) | d-spacing (Å) | 2θ (°) | d-spacing (Å) |
|---|---|---|---|---|---|---|---|
| 6.456 | 13.680 | 18.257 | 4.855 | 25.061 | 3.551 | 30.063 | 2.970 |
| 7.022 | 12.578 | 18.677 | 4.747 | 25.336 | 3.512 | 30.440 | 2.934 |
| 7.722 | 11.439 | 18.997 | 4.668 | 25.777 | 3.454 | 30.661 | 2.914 |
| 9.096 | 9.715 | 19.221 | 4.614 | 26.062 | 3.416 | 31.002 | 2.882 |
| 9.774 | 9.042 | 19.500 | 4.549 | 26.525 | 3.358 | 31.640 | 2.826 |
| 10.884 | 8.122 | 20.201 | 4.392 | 26.644 | 3.343 | 31.858 | 2.807 |
| 11.420 | 7.742 | 20.523 | 4.324 | 26.739 | 3.331 | 32.238 | 2.775 |
| 11.983 | 7.380 | 21.117 | 4.204 | 27.103 | 3.287 | 32.802 | 2.728 |
| 12.455 | 7.101 | 21.342 | 4.160 | 27.418 | 3.250 | 32.879 | 2.722 |
| 12.941 | 6.836 | 21.898 | 4.056 | 27.761 | 3.211 | 33.058 | 2.708 |
| 13.779 | 6.422 | 22.642 | 3.924 | 27.877 | 3.198 | 33.392 | 2.681 |
| 14.033 | 6.306 | 23.045 | 3.856 | 28.183 | 3.164 | 33.780 | 2.651 |
| 14.257 | 6.207 | 23.320 | 3.811 | 28.340 | 3.147 | 34.019 | 2.633 |
| 15.479 | 5.720 | 23.616 | 3.764 | 28.564 | 3.123 | 34.118 | 2.626 |
| 15.863 | 5.582 | 23.780 | 3.739 | 29.217 | 3.054 | 34.559 | 2.593 |
| 16.225 | 5.459 | 24.101 | 3.690 | 29.621 | 3.013 | 35.000 | 2.562 |
| 17.258 | 5.134 | 24.605 | 3.615 | 29.759 | 3.000 | | |

[FIG. 8]
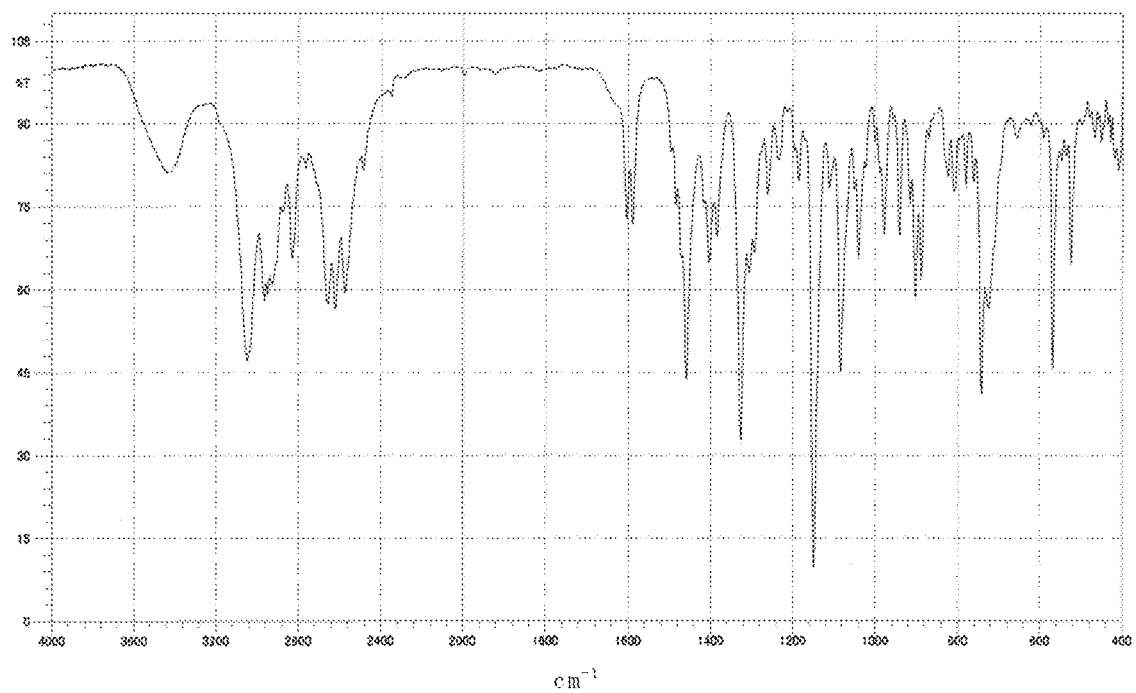
| peak (cm⁻¹) | peak (cm⁻¹) | peak (cm⁻¹) | peak (cm⁻¹) |
|---|---|---|---|
| 408.91 | 761.88 | 1083.99 | 1485.19 |
| 418.55 | 781.17 | 1112.93 | 1496.76 |
| 428.20 | 810.10 | 1147.65 | 1589.34 |
| 433.98 | 825.53 | 1186.22 | 1602.85 |
| 451.34 | 871.82 | 1197.79 | 2574.97 |
| 466.77 | 889.18 | 1215.15 | 2621.26 |
| 480.28 | 902.69 | 1236.37 | 2657.91 |
| 524.64 | 916.19 | 1261.45 | 2763.99 |
| 536.21 | 941.26 | 1292.31 | 2829.57 |
| 547.78 | 956.69 | 1305.81 | 2877.79 |
| 569.00 | 979.84 | 1325.10 | 2927.94 |
| 592.15 | 991.41 | 1384.89 | 2951.09 |
| 621.08 | 1001.06 | 1404.18 | 2964.59 |
| 655.80 | 1024.20 | 1417.68 | 3037.89 |
| 725.23 | 1041.56 | 1458.18 | 3049.46 |
| 742.59 | 1051.20 | 1471.69 | 3433.29 |

[FIG. 9]
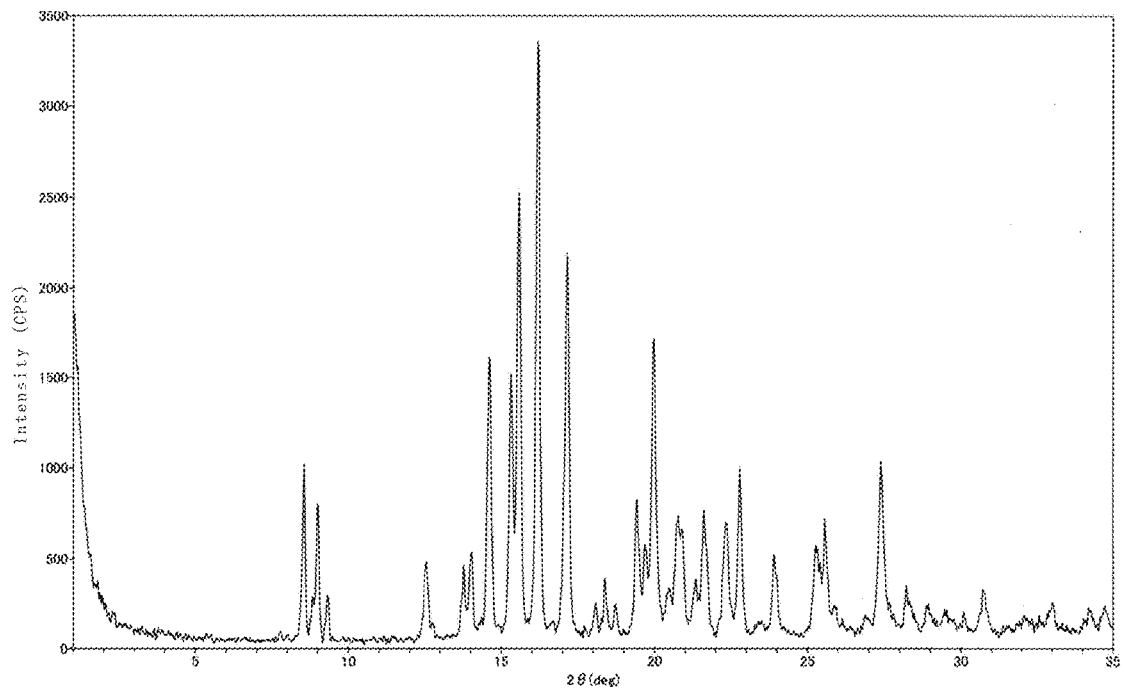
| 2θ (°) | d-spacing (Å) | 2θ (°) | d-spacing (Å) | 2θ (°) | d-spacing (Å) | 2θ (°) | d-spacing (Å) |
|---|---|---|---|---|---|---|---|
| 7.776 | 11.3602 | 16.201 | 5.4666 | 21.341 | 4.1601 | 29.540 | 3.0215 |
| 8.016 | 11.0210 | 16.652 | 5.3196 | 21.619 | 4.1074 | 30.103 | 2.9663 |
| 8.557 | 10.3253 | 17.160 | 5.1632 | 22.341 | 3.9761 | 30.725 | 2.9076 |
| 8.842 | 9.9934 | 17.728 | 4.9989 | 22.800 | 3.8971 | 31.509 | 2.8370 |
| 9.001 | 9.8167 | 18.098 | 4.8977 | 23.499 | 3.7828 | 31.859 | 2.8067 |
| 9.323 | 9.4782 | 18.385 | 4.8218 | 23.919 | 3.7172 | 32.096 | 2.7864 |
| 12.559 | 7.0427 | 18.737 | 4.7320 | 25.281 | 3.5199 | 32.586 | 2.7457 |
| 12.744 | 6.9407 | 19.421 | 4.5668 | 25.580 | 3.4795 | 33.019 | 2.7106 |
| 13.779 | 6.4214 | 19.700 | 4.5028 | 25.881 | 3.4398 | 34.220 | 2.6182 |
| 14.037 | 6.3039 | 19.979 | 4.4405 | 26.900 | 3.3117 | 34.740 | 2.5802 |
| 14.619 | 6.0542 | 20.480 | 4.3330 | 27.401 | 3.2522 | | |
| 15.321 | 5.7785 | 20.779 | 4.2715 | 28.223 | 3.1594 | | |
| 15.580 | 5.6830 | 20.898 | 4.2472 | 28.938 | 3.0829 | | |

[FIG. 10]
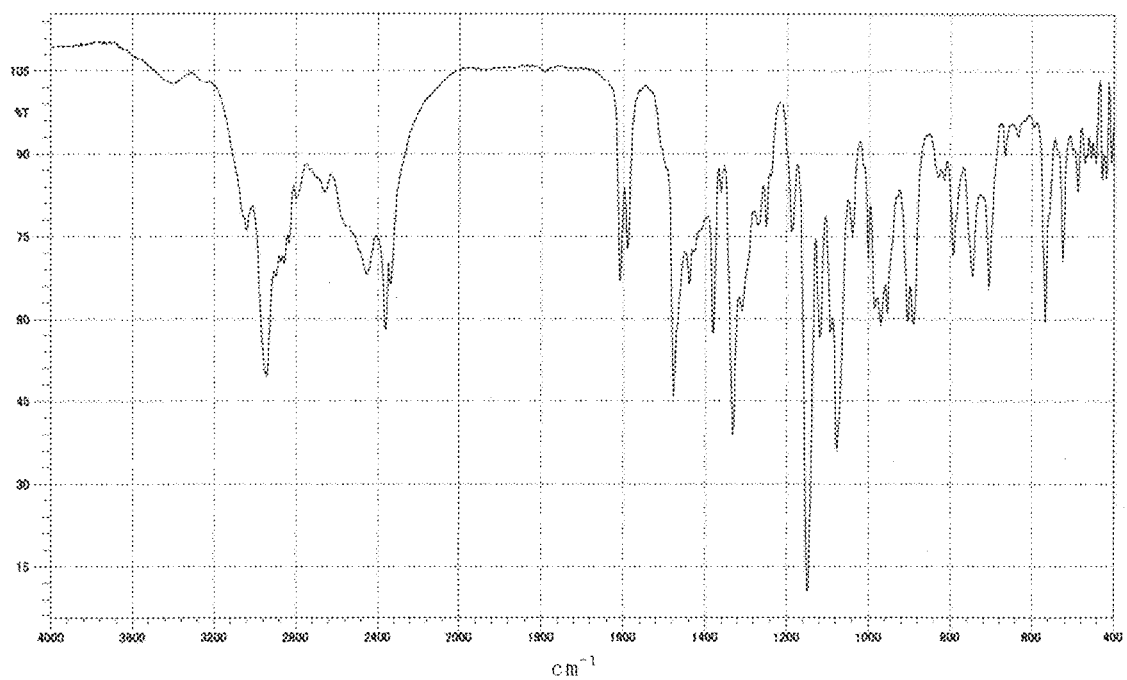
| peak (cm⁻¹) | peak (cm⁻¹) | peak (cm⁻¹) | peak (cm⁻¹) |
| --- | --- | --- | --- |
| 405.05 | 705.95 | 1093.64 | 1589.34 |
| 418.55 | 746.45 | 1118.71 | 1606.70 |
| 428.20 | 794.67 | 1147.65 | 2339.65 |
| 443.63 | 815.89 | 1188.15 | 2362.80 |
| 455.20 | 829.39 | 1249.87 | 2453.45 |
| 464.84 | 891.11 | 1271.09 | 2659.84 |
| 470.63 | 904.61 | 1309.67 | 2798.71 |
| 487.99 | 954.76 | 1330.88 | 2833.43 |
| 524.64 | 970.19 | 1361.74 | 2856.58 |
| 567.07 | 985.62 | 1381.03 | 2873.94 |
| 596.00 | 1001.06 | 1427.32 | 2897.08 |
| 632.65 | 1039.63 | 1438.90 | 2941.44 |
| 667.37 | 1076.28 | 1477.47 | 3039.81 |

[FIG. 11]
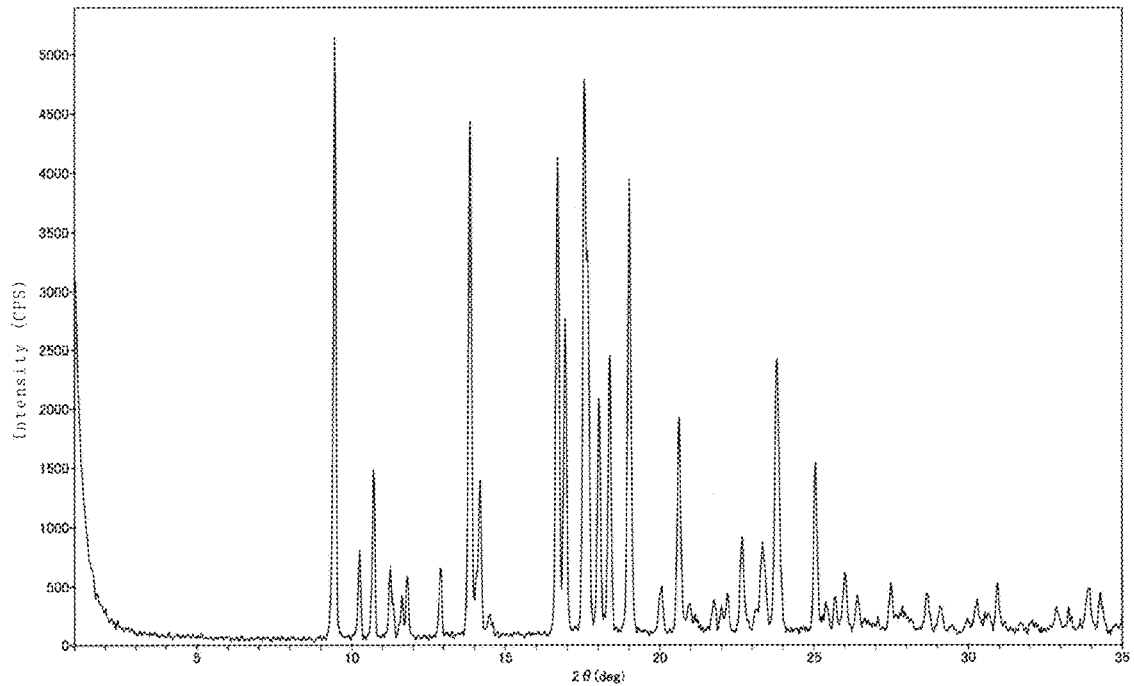
| 2θ (°) | d-spacing (Å) | 2θ (°) | d-spacing (Å) | 2θ (°) | d-spacing (Å) | 2θ (°) | d-spacing (Å) |
|---|---|---|---|---|---|---|---|
| 9.463 | 9.3389 | 17.658 | 5.0186 | 23.341 | 3.8081 | 29.103 | 3.0659 |
| 10.260 | 8.6144 | 18.038 | 4.9138 | 23.819 | 3.7327 | 29.493 | 3.0262 |
| 10.722 | 8.2448 | 18.380 | 4.8231 | 25.058 | 3.5508 | 29.978 | 2.9784 |
| 11.261 | 7.8513 | 19.020 | 4.6622 | 25.385 | 3.5058 | 30.281 | 2.9492 |
| 11.641 | 7.5957 | 20.059 | 4.4230 | 25.681 | 3.4660 | 30.660 | 2.9137 |
| 11.818 | 7.4825 | 20.638 | 4.3002 | 26.002 | 3.4240 | 30.943 | 2.8876 |
| 12.916 | 6.8487 | 20.961 | 4.2347 | 26.401 | 3.3732 | 31.683 | 2.8218 |
| 13.876 | 6.3768 | 21.141 | 4.1991 | 26.653 | 3.3418 | 32.091 | 2.7869 |
| 14.195 | 6.2344 | 21.742 | 4.0843 | 27.065 | 3.2919 | 32.879 | 2.7218 |
| 14.498 | 6.1048 | 21.998 | 4.0373 | 27.499 | 3.2409 | 33.263 | 2.6913 |
| 16.701 | 5.3042 | 22.182 | 4.0042 | 27.862 | 3.1995 | 33.936 | 2.6395 |
| 16.941 | 5.2294 | 22.680 | 3.9175 | 28.158 | 3.1666 | 34.297 | 2.6125 |
| 17.563 | 5.0457 | 23.139 | 3.8409 | 28.663 | 3.1120 | 34.799 | 2.5760 |

[FIG. 12]
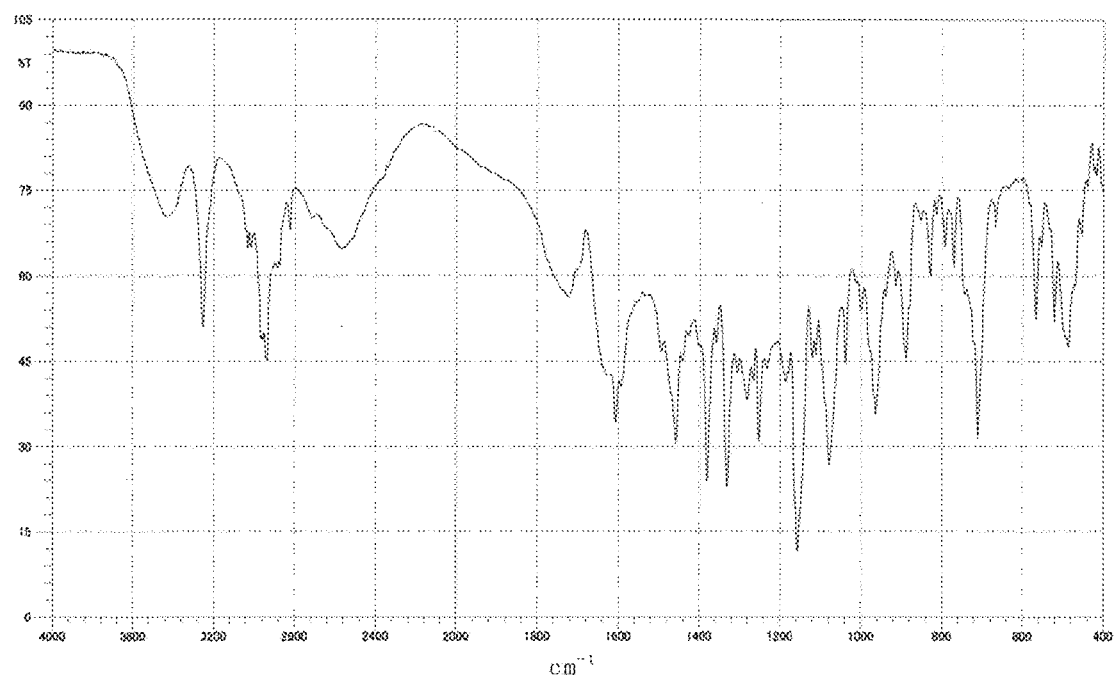
| peak (cm⁻¹) | peak (cm⁻¹) | peak (cm⁻¹) | peak (cm⁻¹) |
| --- | --- | --- | --- |
| 453.27 | 889.18 | 1305.81 | 1724.36 |
| 470.63 | 914.26 | 1330.88 | 2551.82 |
| 486.06 | 939.33 | 1357.89 | 2571.11 |
| 520.78 | 964.41 | 1381.03 | 2711.92 |
| 553.57 | 1001.06 | 1427.32 | 2823.79 |
| 567.07 | 1037.70 | 1442.75 | 2875.86 |
| 667.37 | 1078.21 | 1458.18 | 2887.44 |
| 711.73 | 1111.00 | 1494.83 | 2937.59 |
| 771.53 | 1120.64 | 1535.34 | 2956.87 |
| 792.74 | 1157.29 | 1554.63 | 3018.60 |
| 813.96 | 1232.51 | 1593.20 | 3032.10 |
| 829.39 | 1251.80 | 1606.70 | 3253.91 |
| 852.54 | 1280.73 | 1703.14 | 3431.36 |

[FIG. 13]
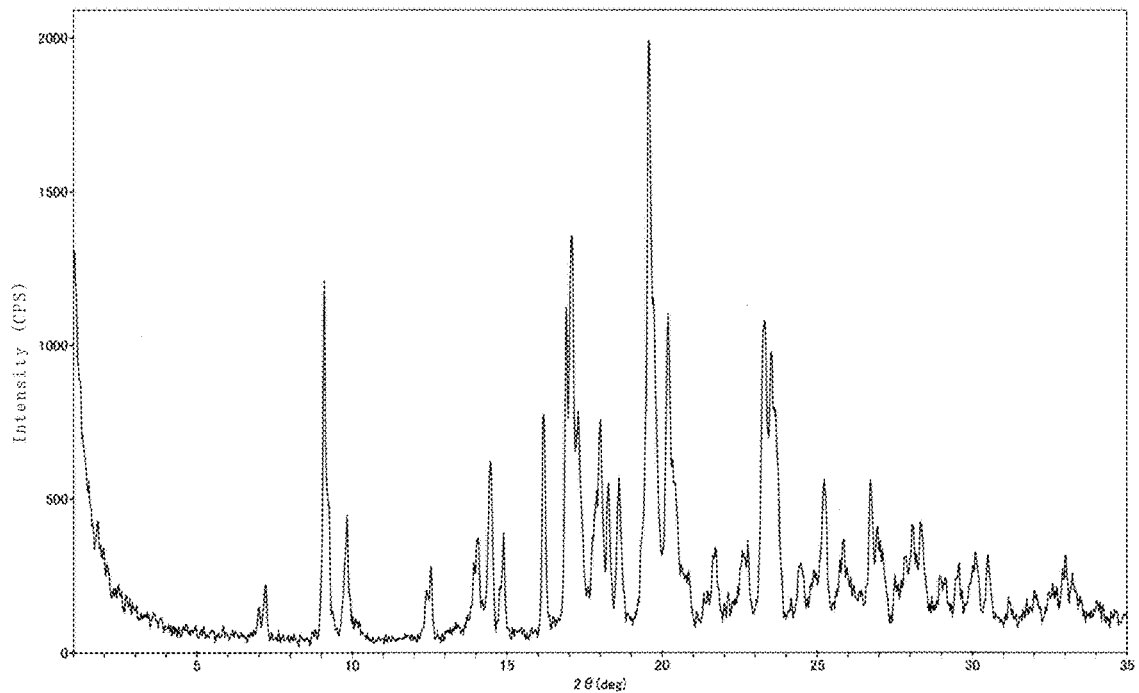
| 2θ (°) | d-spacing (Å) | 2θ (°) | d-spacing (Å) | 2θ (°) | d-spacing (Å) | 2θ (°) | d-spacing (Å) |
|---|---|---|---|---|---|---|---|
| 6.984 | 12.6464 | 16.919 | 5.2361 | 22.779 | 3.9006 | 29.137 | 3.0624 |
| 7.201 | 12.2654 | 17.081 | 5.1869 | 23.320 | 3.8114 | 29.570 | 3.0185 |
| 9.103 | 9.7067 | 17.317 | 5.1168 | 23.557 | 3.7735 | 30.102 | 2.9663 |
| 9.252 | 9.5505 | 17.902 | 4.9508 | 24.460 | 3.6362 | 30.502 | 2.9283 |
| 9.840 | 8.9818 | 18.018 | 4.9192 | 24.900 | 3.5730 | 31.171 | 2.8670 |
| 10.124 | 8.7301 | 18.278 | 4.8497 | 25.239 | 3.5258 | 31.773 | 2.8140 |
| 12.402 | 7.1312 | 18.621 | 4.7613 | 25.855 | 3.4431 | 32.023 | 2.7927 |
| 12.539 | 7.0535 | 19.599 | 4.5258 | 26.724 | 3.3332 | 32.602 | 2.7444 |
| 13.355 | 6.6246 | 20.200 | 4.3924 | 26.976 | 3.3026 | 33.020 | 2.7105 |
| 13.942 | 6.3468 | 20.858 | 4.2555 | 27.520 | 3.2385 | 33.241 | 2.6930 |
| 14.061 | 6.2935 | 21.344 | 4.1595 | 27.878 | 3.1977 | 34.038 | 2.6318 |
| 14.479 | 6.1124 | 21.719 | 4.0886 | 28.083 | 3.1748 | | |
| 14.898 | 5.9415 | 22.134 | 4.0128 | 28.344 | 3.1462 | | |
| 16.182 | 5.4730 | 22.639 | 3.9245 | 28.978 | 3.0787 | | |

[FIG. 14]
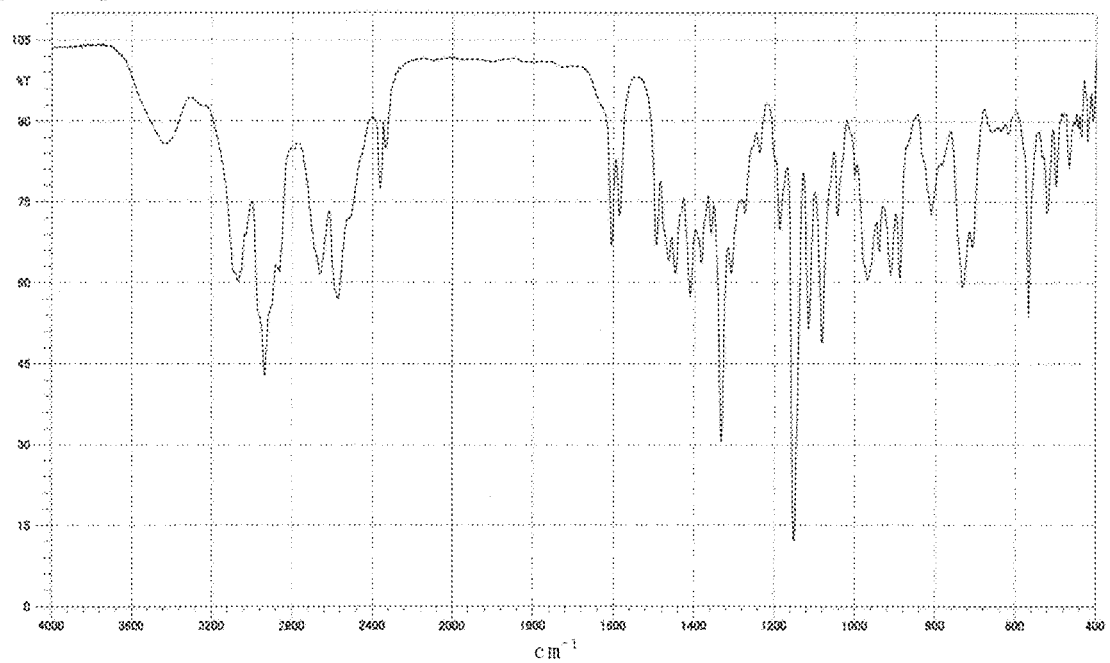
| peak (cm⁻¹) | peak (cm⁻¹) | peak (cm⁻¹) | peak (cm⁻¹) |
|---|---|---|---|
| 406.98 | 732.95 | 1186.22 | 1604.77 |
| 420.48 | 785.03 | 1236.37 | 2517.10 |
| 435.91 | 810.10 | 1273.02 | 2571.11 |
| 443.63 | 889.18 | 1307.74 | 2659.84 |
| 453.27 | 910.40 | 1330.88 | 2791.00 |
| 466.77 | 939.33 | 1357.89 | 2864.29 |
| 499.56 | 970.19 | 1382.96 | 2935.66 |
| 520.78 | 1001.06 | 1409.96 | 3030.17 |
| 534.28 | 1043.49 | 1448.54 | 3070.68 |
| 567.07 | 1082.07 | 1463.97 | 3089.96 |
| 619.15 | 1114.86 | 1494.83 | 3425.58 |
| 707.88 | 1151.50 | 1585.49 | |

[FIG. 15]
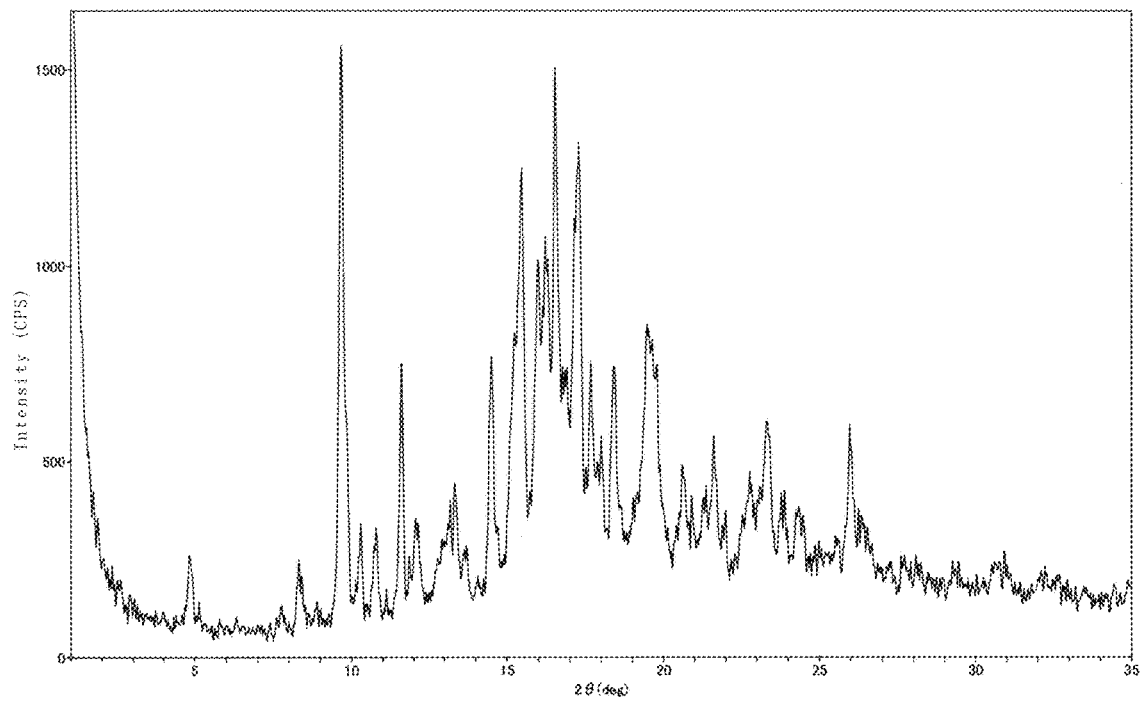
| 2θ (°) | d-spacing (Å) | 2θ (°) | d-spacing (Å) | 2θ (°) | d-spacing (Å) | 2θ (°) | d-spacing (Å) |
|---|---|---|---|---|---|---|---|
| 4.841 | 18.2409 | 12.941 | 6.8352 | 17.682 | 5.0118 | 23.322 | 3.8111 |
| 5.796 | 15.2353 | 13.183 | 6.7104 | 18.018 | 4.9191 | 23.896 | 3.7208 |
| 6.338 | 13.9343 | 13.344 | 6.6301 | 18.404 | 4.8170 | 24.342 | 3.6536 |
| 7.774 | 11.3629 | 13.721 | 6.4483 | 19.038 | 4.6578 | 24.996 | 3.5595 |
| 8.322 | 10.6162 | 14.077 | 6.2865 | 19.481 | 4.5530 | 25.526 | 3.4867 |
| 8.896 | 9.9324 | 14.519 | 6.0960 | 19.639 | 4.5166 | 25.982 | 3.4266 |
| 9.681 | 9.1289 | 15.241 | 5.8087 | 19.796 | 4.4812 | 26.361 | 3.3782 |
| 10.299 | 8.5819 | 15.478 | 5.7202 | 20.621 | 4.3038 | 27.278 | 3.2667 |
| 10.782 | 8.1989 | 16.000 | 5.5348 | 20.912 | 4.2445 | 27.717 | 3.2159 |
| 11.115 | 7.9537 | 16.239 | 5.4537 | 21.379 | 4.1529 | 28.095 | 3.1735 |
| 11.617 | 7.6116 | 16.543 | 5.3543 | 21.623 | 4.1065 | 29.266 | 3.0491 |
| 11.862 | 7.4549 | 16.916 | 5.2370 | 21.998 | 4.0374 | 30.640 | 2.9155 |
| 12.061 | 7.3319 | 17.165 | 5.1616 | 22.562 | 3.9377 | 32.246 | 2.7738 |
| 12.765 | 6.9295 | 17.300 | 5.1218 | 22.800 | 3.8972 | 32.624 | 2.7425 |

[FIG. 16]
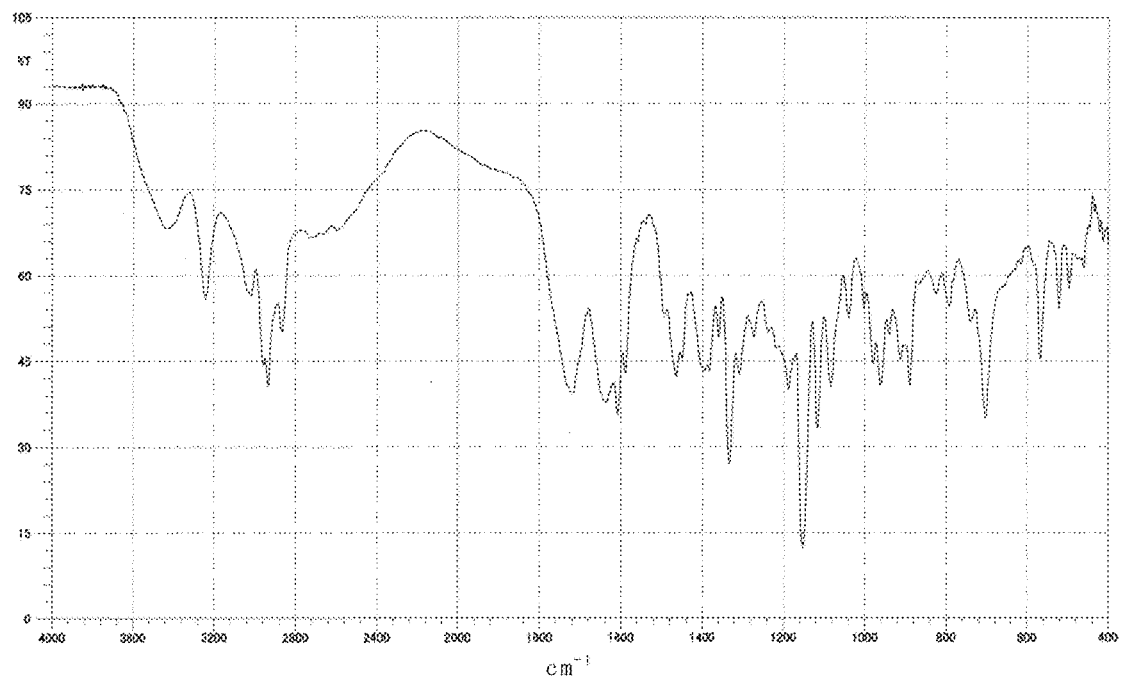
| peak (cm⁻¹) | peak (cm⁻¹) | peak (cm⁻¹) | peak (cm⁻¹) |
|---|---|---|---|
| 460.99 | 889.18 | 1273.02 | 1608.63 |
| 497.63 | 912.33 | 1307.74 | 1635.64 |
| 522.71 | 939.33 | 1332.81 | 1718.58 |
| 569.00 | 962.48 | 1357.89 | 2596.19 |
| 615.29 | 979.84 | 1381.03 | 2661.77 |
| 628.79 | 1002.98 | 1396.46 | 2729.27 |
| 661.58 | 1039.63 | 1450.47 | 2864.29 |
| 704.02 | 1083.99 | 1463.97 | 2935.66 |
| 740.67 | 1116.78 | 1494.83 | 2960.73 |
| 792.74 | 1151.50 | 1539.20 | 3022.45 |
| 825.53 | 1188.15 | 1558.48 | 3244.27 |
| 866.04 | 1238.30 | 1589.34 | 3435.22 |

CRYSTAL OF SALT OF NOVEL 3-AZABICYCLO[3.1.0]HEXANE DERIVATIVE AND PHARMACEUTICAL USE THEREOF

CROSS-REFERENCE TO RELATED APPLICATIONS

This Application is a U.S. National Stage Application of PCT/JP2016/064942 filed May 19, 2016, which claims priority to Japanese Application No. 2015103161 filed May 20, 2015 all of which are incorporated by reference in their entirety.

THE NAMES OF THE PARTIES TO A JOINT RESEARCH AGREEMENT

The present disclosure was made by or on behalf of the below listed parties to a joint research agreement. The joint research agreement was in effect on or before the date the present disclosure was made and the present disclosure was made as a result of activities undertaken within the scope of the joint research agreement. The parties to the joint research agreement are (1) Sanwa Kagaku Kenkyusho Co., Ltd. and (2) Ube Industries, Ltd.

TECHNICAL FIELD

The present invention relates to a crystal of a salt of a novel 3-azabicyclo[3.1.0]hexane derivative useful as a drug and medicinal uses thereof. The compound has various medicinal uses as a μ-opioid receptor antagonist.

BACKGROUND ART

Opioid is a collective term for alkaloid and synthetic or endogenous peptides having morphine-like activities such as narcotic analgesics and their related synthetic analgesics. As opioid receptors involved in the expression of action of opioids, four subtypes of μ, κ, δ, and ORL-1 are currently known. Among them, μ-opioid receptors are receptors that are most relevant to the action of morphine. In addition to morphine, fentanyl and methionine enkephalin and β-endorphin, which are endogenous opioids, also act on μ-opioid receptors.

Administration of morphine or fentanyl, which is a μ-opioid receptor agonist, causes itchiness. Also in animal experiments, morphine induces the act of scratching in spinal intrathecal administration to monkeys, administration to the medullary dorsal horn of rats, and intracisternal administration to mice. Further, itchiness of refractory pruritic diseases is improved by μ-opioid receptor antagonists, and therefore it is considered that activation of μ-opioid receptors by methionine enkephalin and β-endorphin, which are endogenous opioids, is involved in the occurrence of itchiness.

It has been confirmed in various clinical tests that μ-opioid receptor antagonists such as naltrexone suppresses itchiness in dialysis patients and patients with cholestatic liver cirrhosis. Therefore, the development of μ-opioid receptor antagonists as antipruritic drugs has been expected, but there has been no approved drugs until now. In addition, naltrexone has side effects such as nausea, vomiting, and hyperalgesia, such as abdominal pain, and diarrhea, and is therefore not necessarily satisfactory as an antipruritic drug (Non-Patent Literature 1). Therefore, there has been demand for the development of a μ-opioid receptor-selective drug that has few side effects and high safety.

Many 3-azabicyclo[3.1.0]hexane derivatives having μ-opioid receptor antagonistic action have heretofore been reported (Patent Literatures 1 to 15, Non-Patent Literatures 2 to 4), but all the compounds disclosed in these documents are different in structure from the compound according to the present invention.

CITATIONS LIST

Patent Literatures

Patent Literature 1: WO 2000/039089
Patent Literature 2: U.S. Pat. No. 6,313,312
Patent Literature 3: WO 2001/098267
Patent Literature 4: US Patent Application Publication No. 2002/0025948
Patent Literature 5: WO 2003/035622
Patent Literature 6: US Patent Application Publication No. 2003/0087898
Patent Literature 7: WO 2005/018645
Patent Literature 8: US Patent Application Publication No. 2005/0043327
Patent Literature 9: WO 2005/018670
Patent Literature 10: US Patent Application Publication No. 2005/0043345
Patent Literature 11: WO 2005/033080
Patent Literature 12: US Patent Application Publication No. 2005/0075387
Patent Literature 13: WO 2005/037790
Patent Literature 14: US Patent Application Publication No. 2005/0113437
Patent Literature 15: WO 2008/075162

Non-Patent Literatures

Non-Patent Literature 1: Drugs, 35, 192-213 (1988)
Non-Patent Literature 2: Bioorganic and Medicinal Chemistry Letters, 21 (2011) 4608-4611
Non-Patent Literature 3: Medicinal Chemistry Communications, 2 (2011) 1001-1005
Non-Patent Literature 4: Bioorganic and Medicinal Chemistry Letters, 22 (2012) 2200-2203

SUMMARY OF INVENTION

Technical Problems

In general, crystal polymorphs have different physical properties (stability, solubility, etc.). In drug development, stability that affects quality control and solubility that affects bioavailability are very important, and therefore it is necessary to search crystal forms having excellent physical properties.

Accordingly, it is an object of the present invention to provide a crystal comprising a compound which has μ-opioid receptor antagonistic action, few side effects, and high safety, and having high purity and excellent physical properties (stability, solubility, etc.), and a method for producing the crystal, and to provide an agent for preventing or treating pruritus based on μ-opioid receptor antagonistic action.

Solutions to Problems

In view of the above points, the present inventors have intensively studied to develop a μ-opioid receptor antagonist having a novel structure to achieve the above object. As a result, the present inventors have found that a compound represented by the following general formula (I) and a pharmacologically-acceptable salt thereof have very excellent μ-opioid receptor antagonistic action, and have found a crystal of salt of the compound having excellent physical properties as a drug substance and a method for producing the same. These findings have led to the completion of the present invention.

More specifically, the present invention includes the following [1] to [18].

[1] A crystal of a salt comprising: a compound represented by a formula (I)

[Chemical Formula 1]

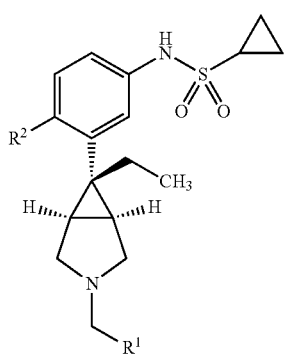

(I)

[wherein $R^2$ is a hydrogen atom or a halogen atom, and $R^1$ is a group selected from the group consisting of

[Chemical Formula 2]

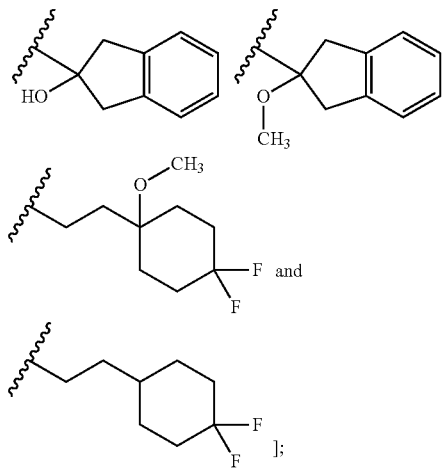

and an acid selected from the group consisting of hydrochloric acid, hydrobromic acid, and oxalic acid.

[2] A crystal of N-(3{(1R,5S,6r)-6-ethyl-3-[(2-hydroxy-2,3-dihydro-1H-inden-2-yl)methyl]-3-azabicyclo[3.1.0]hexan-6-yl}-4-fluorophenyl)cyclopropanesulfonamide hydrochloride.

[3] The crystal according to [2], which has a diffraction peak at a diffraction angle (2θ±0.2°) of 8.3° in powder X-ray diffraction.

[4] A crystal of N-(3{(1R,5S,6r)-6-ethyl-3-[2-hydroxy-2,3-dihydro-1H-inden-2-yl)methyl]-3-azabicyclo[3.1.0]hexan-6-yl}-4-fluorophenyl)cyclopropanesulfonamide hydrobromide.

[5] The crystal according to [4], which has a diffraction peak at a diffraction angle (2θ±0.2°) of 9.1° in powder X-ray diffraction.

[6] A crystal of N-(3-{(1R,5S,6r)-6-ethyl-3-[(2-methoxy-2,3-dihydro-1H-inden-2-yl)methyl]-3-azabicyclo[3.1.0]hexan-6-yl}phenyl)cyclopropanesulfonamide hydrochloride.

[7] The crystal according to [6], which has a diffraction peak at a diffraction angle (2θ±0.2°) of 11.6° in powder X-ray diffraction.

[8] A crystal of N-(3-{(1R,5S,6r)-6-ethyl-3-[(2-methoxy-2,3-dihydro-1H-inden-2-yl)methyl]-3-azabicyclo[3.1.0]hexan-6-yl}phenyl)cyclopropanesulfonamide hydrobromide.

[9] The crystal according to [8], which has a diffraction peak at a diffraction angle (2θ±0.2°) of 9.8° in powder X-ray diffraction.

[10] A crystal of N-(3-{(1R,5S,6r)-3-[3-(4,4-difluoro-1-methoxycyclohexyl)propyl]-6-ethyl-3-azabicyclo[3.1.0]hexan-6-yl}phenyl)cyclopropanesulfonamide hydrochloride.

[11] The crystal according to [10], which has a diffraction peak at a diffraction angle (2θ±0.2°) of 16.2° in powder X-ray diffraction.

[12] A crystal of N-{3-{(1R,5S,6r)-3-[3-(4,4-difluoro-1-methoxycyclohexyl)propyl]-6-ethyl-3-azabicyclo[3.1.0]hexan-6-yl}phenyl)cyclopropanesulfonamide oxalate.

[13] The crystal according to [12], which has a diffraction peak at a diffraction angle (2θ±0.2°) of 9.5° in powder X-ray diffraction.

[14] A crystal of N-(3-{(1R,5S,6r)-3-[3-(4,4-difluorocyclohexyl)propyl]-6-ethyl-3-azabicyclo[3.1.0]hexan-6-yl}phenyl)cyclopropanesulfonamide hydrobromide.

[15] The crystal according to [14], which has a diffraction peak at a diffraction angle (2θ±0.2°) of 9.1° in powder X-ray diffraction.

[16] A crystal of N-(3-{(1R,5S,6r)-3-[3-(4,4-difluorocyclohexyl)propyl]-6-ethyl-3-azabicyclo[3.1.0]hexan-6-yl}phenyl)cyclopropanesulfonamide oxalate.

[17] The crystal according to [16], which has a diffraction peak at a diffraction angle (2θ±0.2°) of 9.7° in powder X-ray diffraction.

[18] A pharmaceutical composition comprising the crystal according to any one of [1] to [17] as an active ingredient.

Advantageous Effects of Invention

The compound constituting the crystal of a salt according to the present invention (hereinafter referred to as "compound represented by the formula (I)" or "compound (I)") has excellent μ-opioid receptor antagonistic action and is useful as a preventive or therapeutic agent for pruritus. Further, the crystal according to the present invention has excellent physical properties (stability, solubility, etc.), and is very suitable for use as a drug because an organic solvent used in production of the crystal is not incorporated into the crystal. It is to be noted that the compound (I) is an antagonist that exerts little agonistic action on μ-opioid receptors and has high μ-opioid receptor selectivity, and therefore the crystal according to the present invention or a pharmaceutical composition containing the crystal is a safe and useful drug having few side effects.

BRIEF DESCRIPTION OF DRAWINGS

FIG. 1 is a graph showing a powder X-ray diffraction pattern of a crystal obtained in Example 1.

FIG. 2 is an infrared absorption spectrum of the crystal obtained in Example 1.

FIG. 3 is a graph showing a powder X-ray diffraction pattern of a crystal obtained in Example 2.

FIG. 4 is an infrared absorption spectrum of the crystal obtained in Example 2.

FIG. 5 is a graph showing a powder X-ray diffraction pattern of a crystal obtained in Example 3.

FIG. 6 is an infrared absorption spectrum of the crystal obtained in Example 3.

FIG. 7 is a graph showing a powder X-ray diffraction pattern of a crystal obtained in Example 4.

FIG. 8 is an infrared absorption spectrum of the crystal obtained in Example 4.

FIG. 9 is a graph showing a powder X-ray diffraction pattern of a crystal obtained in Example 5.

FIG. 10 is an infrared absorption spectrum of the crystal obtained in Example 5.

FIG. 11 is a graph showing a powder X-ray diffraction pattern of a crystal obtained in Example 6.

FIG. 12 is an infrared absorption spectrum of the crystal obtained in Example 6.

FIG. 13 is a graph showing a powder X-ray diffraction pattern of a crystal obtained in Example 7.

FIG. 14 is an infrared absorption spectrum of the crystal obtained in Example 7.

FIG. 15 is a graph showing a powder X-ray diffraction pattern of a crystal obtained in Example 8.

FIG. 16 is an infrared absorption spectrum of the crystal obtained in Example 8.

DETAILED DESCRIPTION OF INVENTION

Definitions of terms used in this description will be described below.

The salts of the compound (I) or hydrates thereof may each form two or more crystals (crystal polymorphs) which have different internal structures and physicochemical properties depending on reaction conditions and crystallization conditions. Further, the salts of the compound (I) or hydrates thereof may each form an amorphous solid. Therefore, a mixture of the crystal specified in the claims and another crystal of the salt of the compound (I) or an amorphous solid is also included in the present invention as long as the crystal specified in the claims is contained in an arbitrary ratio. That is, the content of the specific crystal form according to the present invention is preferably 50% or more, more preferably 80% or more, still more preferably 90% or more, particularly preferably 95% or more, most preferably 97% or more.

In the present invention, the crystal refers to a solid having an internal structure three-dimensionally formed by regular repetition of constituent atoms (or groups thereof), and is distinguished from an amorphous solid not having such a regular internal structure. Whether or not a solid is a crystal can be confirmed by a crystallographically-known method (e.g., powder X-ray crystallographic analysis, differential scanning calorimetric analysis). For example, when a clear peak is observed in an X-ray diffraction pattern obtained by irradiating a certain solid with characteristic X-rays (e.g., copper Kα1 rays), the solid is determined to be a crystal, and when no clear peak is observed, the solid is determined to be an amorphous solid. When a peak can be read but is not clear (e.g., when a peak is broad), the solid is determined to be a crystal having low crystallinity, and such a crystal having low crystallinity is also included in the crystal according to the present invention.

In powder X-ray crystal diffraction, a sample solid is usually irradiated with Kα rays obtained by irradiating copper with accelerated electron beams to measure X-ray intensity, and the relationship between the X-ray intensity and the diffraction angle is represented as a pattern (also referred to as X-ray diffraction pattern). Here, the Kα rays contain Kα1 rays and Kα2 rays, and refer to those in which Kα1 rays and Kα2 rays are not separated unless otherwise specified. The X-ray diffraction pattern may be obtained by analyzing diffraction derived from both Kα1 rays and Kα2 rays, or may be obtained by analyzing only diffraction derived from Kα1 rays taken out from diffraction derived from both Kα1 rays and Kα2 rays. In the present invention, the powder X-ray diffraction pattern obtained by irradiation with Kα rays includes an X-ray diffraction pattern obtained by analyzing diffraction derived from Kα rays and an X-ray diffraction pattern obtained by analyzing diffraction derived from Kα1 rays.

The d-spacing [angstrom (Å)] can be calculated by the formula: $2d \sin \theta = n\lambda$ wherein n=1. It is to be noted that 1 Å is synonymous with $10^{-10}$ m. In the above formula, the wavelength λ of Kα rays is 1.54 Å, and the wavelength λ of Kα1 rays is 1.541 Å.

According to "Japanese Pharmacopoeia Technical Information 2011 2.58 Powder X-ray Diffraction Method", the diffraction angle (2θ) in powder X-ray diffraction may generally have a margin of error of ±0.2°. Therefore, the value of the diffraction angle should be understood as including a numeric value within the range of about ±0.2°. That is, not only the crystals whose peaks in powder X-ray diffraction appear at completely the same diffraction angle but also the crystals whose peaks appear at the diffraction angle with an error of about ±0.2° are included in the scope of the present invention. It is to be noted that the intensity and resolution of the diffraction peak may vary according to the state of the crystal and various conditions such as measurement conditions of powder X-ray diffraction. However, the crystal can be identified by the diffraction angle, the pattern of two or more diffraction peaks, etc.

In this description, for example, the phrase "having a diffraction peak at a diffraction angle (2θ±0.2°) of 8.3°" means "having a diffraction peak at a diffraction angle (2θ) of 8.1° to 8.5°". Other diffraction angles should be understood in a similar manner.

Here, the relationship between the d-spacing and the diffraction angle is represented by the following formula: $2d \sin \theta = n\lambda$. That is, when the wavelength λ of the characteristic X-rays used for measurement is 1.541 Å, for example, the phrase "having a diffraction peak at a diffraction angle (2θ±0.2°) of 8.3°" can be read as "having a diffraction peak at a d-spacing of 10.6 Å" because, in the above formula, n is 1 and λ is 1.541. The margin of error of the d-spacing means a range calculated from the margin of error of the diffraction angle described above. That is, the phrase "having a diffraction peak at a diffraction angle (2θ±0.2°) of 8.3°" means "having a diffraction peak at a diffraction angle (2θ) of 8.1° to 8.5°", and can further be read as "having a diffraction peak at a d-spacing of 10.4 Å to 10.9 Å". Therefore, in this description, for example, the phrase "having a diffraction peak at a d-spacing of virtually 10.6 Å" means "having a diffraction peak at a d-spacing of 10.4 Å to 10.9 Å", and other d-spacings should be understood in a similar manner.

According to "Japanese Pharmacopoeia Technical Information 2011 2.25 Infrared Spectrophotometry", the wave number may generally have a margin of error of ±0.5% of the wave-number scale. Therefore, the value of the wave number in this description should be understood as including a numeric value in the range of about ±0.5% of the wave-number scale. When infrared spectrophotometry is performed under substantially the same conditions as in this description, 0.5% of the wave-number scale is 18 cm$^{-1}$ because the wave-number scale is 3600 cm$^{-1}$. Therefore, in this description, for example, the phrase "having an absorption peak at a wave number ($v_{max}$±18 cm$^{-1}$) of virtually 737 cm$^{-1}$" means "having an absorption peak in the range of a wave-number ($v_{max}$) of 719 cm$^{-1}$ to 755 cm$^{-1}$". The other wave numbers should be understood in a similar manner.

Hereinbelow, embodiments of the present invention will be described.

The present invention provides a crystal of a salt comprising: a compound represented by a formula (I)

[Chemical Formula 3]

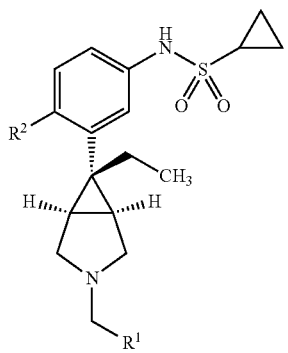

(I)

[wherein R$^2$ is a hydrogen atom or a halogen atom, and R$^1$ is a group selected from the group consisting of

[Chemical Formula 4]

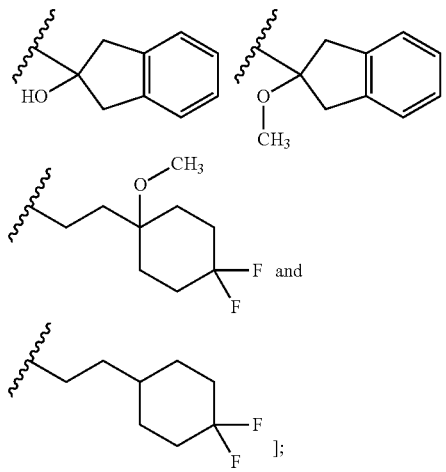

];

and an acid selected from the group consisting of hydrochloric acid, hydrobromic acid, and oxalic acid.

One embodiment of the present invention provides a crystal of N-(3-{(1R,5S,6r)-6-ethyl-3-[(2-hydroxy-2,3-dihydro-1H-inden-2-yl)methyl]-3-azabicyclo[3.1.0]hexan-6-yl}-4-fluorophenyl)cyclopropanesulfonamide hydrochloride.

This crystal is a crystal obtained by precipitating a hydrochloride of the above-described compound using a mixed solvent of an alcohol and water.

This crystal is a crystal having a characteristic diffraction peak at a diffraction angle (2θ±0.2°) of 8.3° in powder X-ray diffraction.

Further, this crystal can also be described as a crystal having characteristic diffraction peaks at diffraction angles (2θ±0.2°) of 8.3° and 13.6° in powder X-ray diffraction.

Further, this crystal can also be described as a crystal having characteristic diffraction peaks at diffraction angles (2θ±0.2°) of 8.3° and 17.4° in powder X-ray diffraction.

Further, this crystal can also be described as a crystal having characteristic diffraction peaks at diffraction angles (2θ±0.2°) of 8.3°, 13.6°, and 17.4° in powder X-ray diffraction.

Further, this crystal can also be described as a crystal having characteristic diffraction peaks at diffraction angles (2θ±0.2°) of 8.3°, 13.6°, 17.4°, and 24.3° in powder X-ray diffraction.

Further, this crystal can also be described as a crystal having characteristic diffraction peaks at diffraction angles (2θ±0.2°) of 8.3°, 13.6°, 16.2°, 17.4°, 19.1°, and 24.3° in powder X-ray diffraction.

Further, this crystal can also be described as a crystal having characteristic diffraction peaks at diffraction angles (2θ±0.2°) at 8.3°, 9.7°, 13.6°, 14.8°, 16.2°, 17.4°, 19.1°, 21.9°, and 24.3° in powder X-ray diffraction.

Further, this crystal can also be described as a crystal having characteristic diffraction peaks at diffraction angles (2θ±0.2°) of 8.3°, 9.1°, 9.7°, 13.6°, 14.8°, 16.2°, 17.4°, 18.3°, 19.1°, 21.9°, 22.9°, and 24.3° in powder X-ray diffraction.

Further, this crystal can also be described as a crystal having a characteristic diffraction peak at a d-spacing of virtually 10.6 Å in powder X-ray diffraction. It is to be noted that "having a diffraction peak at a d-spacing of virtually 10.6 Å" means "having a diffraction peak at a d-spacing of 10.4 to 10.9 Å".

Further, this crystal can also be described as a crystal having characteristic diffraction peaks at d-spacings of virtually 10.6 Å and 6.50 Å in powder X-ray diffraction. It is to be noted that "having diffraction peaks at d-spacings of virtually 10.6 Å and 6.50 Å" means "having diffraction peaks at d-spacings of 10.4 to 10.9 Å and 6.41 to 6.60 Å".

Further, this crystal can also be described as a crystal having characteristic diffraction peaks at d-spacings of virtually 10.6 Å and 5.09 Å in powder X-ray diffraction. It is to be noted that "having diffraction peaks at d-spacings of virtually 10.6 Å and 5.09 Å" means "having diffraction peaks at d-spacings of 10.4 to 10.9 Å and 5.03 to 5.15 Å".

Further, this crystal can also be described as a crystal having characteristic diffraction peaks at d-spacings of virtually 10.6 Å, 6.50 Å, and 5.09 Å in powder X-ray diffraction. It is to be noted that "having diffraction peaks at d-spacings of virtually 10.6 Å, 6.50 Å, and 5.09 Å" means "having diffraction peaks at d-spacings of 10.4 to 10.9 Å, 6.41 to 6.60 Å, and 5.03 to 5.15 Å".

Further, this crystal can also be described as a crystal having characteristic diffraction peaks at d-spacings of virtually 10.6 Å, 6.50 Å, 5.09 Å, and 3.66 Å in powder X-ray diffraction. It is to be noted that "having diffraction peaks at d-spacings of virtually 10.6 Å, 6.50 Å, 5.09 Å, and 3.66 Å" means "having diffraction peaks at d-spacings of 10.4 to 10.9 Å, 6.41 to 6.60 Å, 5.03 to 5.15 Å, and 3.63 to 3.69 Å".

Further, this crystal can also be described as a crystal having characteristic diffraction peaks at d-spacings of virtually 10.6 Å, 6.50 Å, 5.46 Å, 5.09 Å, 4.64 Å, and 3.66 Å in powder X-ray diffraction. It is to be noted that "having diffraction peaks at d-spacings of virtually 10.6 Å, 6.50 Å, 5.46 Å, 5.09 Å, 4.64 Å, and 3.66 Å" means "having diffraction peaks at d-spacings of 10.4 to 10.9 Å, 6.41 to 6.60 Å, 5.40 to 5.53 Å, 5.03 to 5.15 Å, 4.59 to 4.69 Å, and 3.63 to 3.69 Å".

Further, this crystal can also be described as a crystal having characteristic diffraction peaks at d-spacings of virtually 10.6 Å, 9.11 Å, 6.50 Å, 5.98 Å, 5.46 Å, 5.09 Å, 4.64 Å, 4.05 Å, and 3.66 Å. It is to be noted that "having diffraction peaks at d-spacings of virtually 10.6 Å, 9.11 Å, 6.50 Å, 5.98 Å, 5.46 Å, 5.09 Å, 4.64 Å, 4.05 Å, and 3.66 Å" means "having diffraction peaks at d-spacings of 10.4 to 10.9 Å, 8.92 to 9.30 Å, 6.41 to 6.60 Å, 5.90 to 6.06 Å, 5.40 to 5.53 Å, 5.03 to 5.15 Å, 4.59 to 4.69 Å, 4.02 to 4.09 Å, and 3.63 to 3.69 Å".

Further, this crystal can also be described as a crystal having characteristic diffraction peaks at d-spacings of virtually 10.6 Å, 9.71 Å, 9.11 Å, 6.50 Å, 5.98 Å, 5.46 Å, 5.09 Å, 4.84 Å, 4.64 Å, 4.05 Å, 3.88 Å, and 3.66 Å. It is to be noted that "having diffraction peaks at d-spacings of virtually 10.6 Å, 9.71 Å, 9.11 Å, 6.50 Å, 5.98 Å, 5.46 Å, 5.09 Å, 4.84 Å, 4.64 Å, 4.05 Å, 3.88 Å, and 3.66 Å" means "having diffraction peaks at d-spacings of 10.4 to 10.9 Å, 9.50 to 9.92 Å, 8.92 to 9.30 Å, 6.41 to 6.60 Å, 5.90 to 6.06 Å, 5.40 to 5.53 Å, 5.03 to 5.15 Å, 4.79 to 4.90 Å, 4.59 to 4.69 Å, 4.02 to 4.09 Å, 3.85 to 3.91 Å, and 3.63 to 3.69 Å".

Further, this crystal can also be described as a crystal having characteristic absorption peaks at wave numbers ($v_{max}$±18 cm$^{-1}$) of virtually 737 cm$^{-1}$ and 3219 cm$^{-1}$ in its infrared absorption spectrum.

Further, this crystal can also be described as a crystal having characteristic absorption peaks at wave numbers ($v_{max}$±18 cm$^{-1}$) of virtually 737 cm$^{-1}$, 800 cm$^{-1}$, 1150 cm$^{-1}$, 1466 cm$^{-1}$, and 3219 cm$^{-1}$ in its infrared absorption spectrum.

Further, this crystal can also be described as a crystal having characteristic absorption peaks at wave numbers ($v_{max}$±18 cm$^{-1}$) of virtually 737 cm$^{-1}$, 756 cm$^{-1}$, 800 cm$^{-1}$, 1150 cm$^{-1}$, 1304 cm$^{-1}$, 1325 cm$^{-1}$, 1466 cm$^{-1}$, 3132 cm$^{-1}$, and 3219 cm$^{-1}$ in its infrared absorption spectrum.

Further, this crystal can also be described as a crystal having characteristic absorption peaks at wave numbers ($v_{max}$±18 cm$^{-1}$) of virtually 629 cm$^{-1}$, 737 cm$^{-1}$, 756 cm$^{-1}$, 800 cm$^{-1}$, 816 cm$^{-1}$, 1003 cm$^{-1}$, 1150 cm$^{-1}$, 1304 cm$^{-1}$, 1325 cm$^{-1}$, 1466 cm$^{-1}$, 3132 cm$^{-1}$, and 3219 cm$^{-1}$ in its infrared absorption spectrum.

One embodiment of the present invention provides a crystal of N-(3-{(1R,5S,6r)-6-ethyl-3-[(2-hydroxy-2,3-dihydro-1H-inden-2-yl)methyl]-3-azabicyclo[3.1.0]hexan-6-yl}-4-fluorophenyl)cyclopropanesulfonamide hydrobromide.

The crystal is a crystal obtained by precipitating a hydrobromide of the above-described compound using a mixed solvent of an alcohol and water.

This crystal is a crystal having a characteristic diffraction peak at a diffraction angle (2θ±0.2°) of 9.1° in powder X-ray diffraction.

Further, this crystal can also be described as a crystal having characteristic diffraction peaks at diffraction angles (2θ±0.2°) of 9.1° and 14.1° in powder X-ray diffraction.

Further, this crystal can also be described as a crystal having characteristic diffraction peaks at diffraction angles (2θ±0.2°) of 9.1° and 17.3° in powder X-ray diffraction.

Further, this crystal can also be described as a crystal having characteristic diffraction peaks at diffraction angles (2θ±0.2°) of 9.1°, 14.1°, and 17.3° in powder X-ray diffraction.

Further, this crystal can also be described as a crystal having characteristic diffraction peaks at diffraction angles (2θ±0.2°) of 9.1°, 14.1°, 17.3°, and 24.2° in powder X-ray diffraction.

Further, this crystal can also be described as a crystal having characteristic diffraction peaks at diffraction angles (2θ±0.2°) of 9.1°, 14.1°, 17.3°, 19.1°, 20.2°, and 24.2° in powder X-ray diffraction.

Further, this crystal can also be described as a crystal having characteristic diffraction peaks at diffraction angles (2θ±0.2°) of 9.1°, 9.7°, 14.1°, 14.8°, 17.3°, 19.1°, 20.2°, 21.7° and 24.2° in powder X-ray diffraction.

Further, this crystal can also be described as a crystal having characteristic diffraction peaks at diffraction angles (2θ±0.2°) of 8.1°, 8.2°, 9.1°, 9.7°, 14.1°, 14.8°, 17.3°, 19.1°, 20.2°, 21.7°, 22.8° and 24.2° in powder X-ray diffraction.

Further, this crystal can also be described as a crystal having a characteristic diffraction peak at a d-spacing of virtually 9.71 Å in powder X-ray diffraction. It is to be noted that "having a diffraction peak at a d-spacing of virtually 9.71 Å" means "having a diffraction peak at a d-spacing of 9.50 to 9.92 Å".

Further, this crystal can also be described as a crystal having characteristic diffraction peaks at d-spacings of 9.71 Å and 6.27 Å in powder X-ray diffraction. It is to be noted that "having diffraction peaks at d-spacings of virtually 9.71 Å and 6.27 Å" means "having diffraction peaks at d-spacings of 9.50 to 9.92 Å and 6.19 to 6.36 Å".

Further, this crystal can also be described as a crystal having characteristic diffraction peaks at d-spacings of virtually 9.71 Å and 5.12 Å in powder X-ray diffraction. It is to be noted that "having diffraction peaks at d-spacings of virtually 9.71 Å and 5.12 Å" means "having diffraction peaks at d-spacings of 9.50 to 9.92 Å and 5.06 to 5.18 Å".

Further, this crystal can also be described as a crystal having characteristic diffraction peaks at d-spacings of virtually 9.71 Å, 6.27 Å, and 5.12 Å in powder X-ray diffraction. It is to be noted that "having diffraction peaks at d-spacings of virtually 9.71 Å, 6.27 Å, and 5.12 Å" means "having diffraction peaks at d-spacings of 9.50 to 9.92 Å, 6.19 to 6.36 Å, and 5.06 to 5.18 Å".

Further, this crystal can also be described as a crystal having characteristic diffraction peaks at d-spacings of virtually 9.71 Å, 6.27 Å, 5.12 Å, and 3.67 Å in powder X-ray diffraction. It is to be noted that "having diffraction peaks at d-spacings of virtually 9.71 Å, 6.27 Å, 5.12 Å, and 3.67 Å" means that "having diffraction peaks at d-spacings of 9.50 to 9.92 Å, 6.19 to 6.36 Å, 5.06 to 5.18 Å, and 3.64 to 3.70 Å".

Further, this crystal can also be described as a crystal having characteristic diffraction peaks at d-spacings of virtually 9.71 Å, 6.27 Å, 5.12 Å, 4.64 Å, 4.39 Å, and 3.67 Å in powder X-ray diffraction. It is to be noted that "having diffraction peaks at d-spacings of virtually 9.71 Å, 6.27 Å, 5.12 Å, 4.64 Å, 4.39 Å, and 3.67 Å" means "having diffraction peaks at d-spacings of 9.50 to 9.92 Å, 6.19 to 6.36 Å, 5.06 to 5.18 Å, 4.59 to 4.69 Å, 4.35 to 4.43 Å, and 3.64 to 3.70 Å".

Further, this crystal can also be described as a crystal having characteristic diffraction peaks at d-spacings of virtually 9.71 Å, 9.11 Å, 6.27 Å, 5.98 Å, 5.12 Å, 4.64 Å, 4.39 Å, 4.09 Å, and 3.67 Å in powder X-ray diffraction. It is to be noted that "having diffraction peaks at d-spacings of virtually 9.71 Å, 9.11 Å, 6.27 Å, 5.98 Å, 5.12 Å, 4.64 Å, 4.39 Å, 4.09 Å, and 3.67 Å" means "having diffraction peaks at d-spacings of 9.50 to 9.92 Å, 8.92 to 9.30 Å, 6.19 to 6.36 Å, 5.90 to 6.06 Å, 5.06 to 5.18 Å, 4.59 to 4.69 Å, 4.35 to 4.43 Å, 4.05 to 4.13 Å, and 3.64 to 3.70 Å".

Further, this crystal can also be described as a crystal having characteristic diffraction peaks at d-spacings of virtually 10.9 Å, 10.8 Å, 9.71 Å, 9.11 Å, 6.27 Å, 5.98 Å, 5.12 Å, 4.64 Å, 4.39 Å, 4.09 Å, 3.90 Å, and 3.67 Å in powder X-ray diffraction. It is to be noted that "having diffraction peaks at d-spacings of virtually 10.9 Å, 10.8 Å, 9.71 Å, 9.11 Å, 6.27 Å, 5.98 Å, 5.12 Å, 4.64 Å, 4.39 Å, 4.09 Å, 3.90 Å, and 3.67 Å" means "having diffraction peaks at d-spacings of 10.6 to 11.2 Å, 10.5 to 11.0 Å, 9.50 to 9.92 Å, 8.92 to 9.30 Å, 6.19 to 6.36 Å, 5.90 to 6.06 Å, 5.06 to 5.18 Å, 4.59 to 4.69 Å, 4.35 to 4.43 Å, 4.05 to 4.13 Å, 3.86 to 3.93 Å, and 3.64 to 3.70 Å".

Further, this crystal can also be described as a crystal having characteristic absorption peaks at wave numbers ($\nu_{max} \pm 18$ cm$^{-1}$) of virtually 737 cm$^{-1}$ and 3277 cm$^{-1}$ in its infrared absorption spectrum.

Further, this crystal can also be described as a crystal having characteristic absorption peaks at wave numbers ($\nu_{max} \pm 18$ cm$^{-1}$) of virtually 737 cm$^{-1}$, 797 cm$^{-1}$, 1148 cm$^{-1}$, 1460 cm$^{-1}$, and 3277 cm$^{-1}$ in its infrared absorption spectrum.

Further, this crystal can also be described as a crystal having characteristic absorption peaks at wave numbers ($\nu_{max} \pm 18$ cm$^{-1}$) of virtually 737 cm$^{-1}$, 754 cm$^{-1}$, 797 cm$^{-1}$, 1148 cm$^{-1}$, 1304 cm$^{-1}$, 1323 cm$^{-1}$, 1460 cm$^{-1}$, 3123 cm$^{-1}$, and 3277 cm$^{-1}$ in its infrared absorption spectrum.

Further, this crystal can also be described as a crystal having characteristic absorption peaks at wave numbers ($\nu_{max} \pm 18$ cm$^{-1}$) of virtually 627 cm$^{-1}$, 737 cm$^{-1}$, 754 cm$^{-1}$, 797 cm$^{-1}$, 814 cm$^{-1}$, 1001 cm$^{-1}$, 1148 cm$^{-1}$, 1304 cm$^{-1}$, 1323 cm$^{-1}$, 1460 cm$^{-1}$, 3123 cm$^{-1}$, and 3277 cm$^{-1}$ in its infrared absorption spectrum.

One embodiment of the present invention provides a crystal of N-(3-{(1R,5S,6r)-6-ethyl-3-[(2-methoxy-2,3-dihydro-1H-inden-2-yl)methyl]-3-azabicyclo[3.1.0]hexan-6-yl}phenyl)cyclopropanesulfonamide hydrochloride.

This crystal is a crystal obtained by precipitating a hydrochloride of the above-described compound using a mixed solvent of an alcohol and water.

This crystal is a crystal having a characteristic diffraction peak at a diffraction angle (2θ±0.2°) of 11.6° in powder X-ray diffraction.

Further, this crystal can also be described as a crystal having characteristic diffraction peaks at diffraction angles (2θ±0.2°) of 11.6° and 14.0° in powder X-ray diffraction.

Further, this crystal can also be described as a crystal having characteristic diffraction peaks at diffraction angles (2θ±0.2°) of 11.6° and 17.5° in powder X-ray diffraction.

Further, this crystal can also be described as a crystal having characteristic diffraction peaks at diffraction angles (2θ±0.2°) of 11.6°, 14.0°, and 17.5° in powder X-ray diffraction.

Further, this crystal can also be described as a crystal having characteristic diffraction peaks at diffraction angles (2θ±0.2°) of 11.6°, 14.0°, 17.5°, and 25.1° in powder X-ray diffraction.

Further, this crystal can also be described as a crystal having characteristic diffraction peaks at diffraction angles (2θ±0.2°) of 11.6°, 14.0°, 15.4°, 17.5°, 19.0°, and 25.1° in powder X-ray diffraction.

Further, this crystal can also be described as a crystal having characteristic diffraction peaks at diffraction angles (2θ±0.2°) of 11.6°, 12.4°, 14.0°, 15.4°, 17.5°, 18.4°, 19.0°, 23.1°, and 25.1° in powder X-ray diffraction.

Further, this crystal can also be described as a crystal having characteristic diffraction peaks at diffraction angles (2θ±0.2°) of 11.6°, 12.4°, 14.0°, 15.4°, 15.9°, 17.5°, 18.4°, 19.0°, 20.6°, 22.1°, 23.1°, and 25.1° in powder X-ray diffraction.

Further, this crystal can also be described as a crystal having a characteristic diffraction peak at a d-spacing of virtually 7.62 Å in powder X-ray diffraction. It is to be noted that "having a diffraction peak at a d-spacing of virtually 7.62 Å" means "having a diffraction peak at a d-spacing of 7.49 to 7.75 Å".

Further, this crystal can also be described as a crystal having characteristic diffraction peaks at d-spacings of virtually 7.62 Å and 6.32 Å in powder X-ray diffraction. It is to be noted that "having diffraction peaks at d-spacings of virtually 7.62 Å and 6.32 Å" means "having diffraction peaks at d-spacings of 7.49 to 7.75 Å and 6.23 to 6.41 Å".

Further, this crystal can also be described as a crystal having characteristic diffraction peaks at d-spacings of virtually 7.62 Å and 5.06 Å in powder X-ray diffraction. It is to be noted that "having diffraction peaks at d-spacings of virtually 7.62 Å and 5.06 Å" means "having diffraction peaks at d-spacings of 7.49 to 7.75 Å and 5.00 to 5.12 Å".

Further, this crystal can also be described as a crystal having characteristic diffraction peaks at d-spacings of virtually 7.62 Å, 6.32 Å, and 5.06 Å in powder X-ray diffraction. It is to be noted that "having diffraction peaks at d-spacings of virtually 7.62 Å, 6.32 Å, and 5.06 Å" means "having diffraction peaks at d-spacings of 7.49 to 7.75 Å, 6.23 to 6.41 Å, and 5.00 to 5.12 Å".

Further, this crystal can also be described as a crystal having characteristic diffraction peaks at d-spacings of virtually 7.62 Å, 6.32 Å, 5.06 Å, and 3.54 Å in powder X-ray diffraction. It is to be noted that "having diffraction peaks at d-spacings of virtually 7.62 Å, 6.32 Å, 5.06 Å, and 3.54 Å" means "having diffraction peaks at d-spacings of 7.49 to 7.75 Å, 6.23 to 6.41 Å, 5.00 to 5.12 Å, and 3.52 to 3.57 Å".

Further, this crystal can also be described as a crystal having characteristic diffraction peaks at d-spacings of virtually 7.62 Å, 6.32 Å, 5.75 Å, 5.06 Å, 4.67 Å, and 3.54 Å in powder X-ray diffraction. It is to be noted that "having diffraction peaks at d-spacings of virtually 7.62 Å, 6.32 Å, 5.75 Å, 5.06 Å, 4.67 Å, and 3.54 Å" means "having diffraction peaks at d-spacings of 7.49 to 7.75 Å, 6.23 to 6.41 Å, 5.67 to 5.82 Å, 5.00 to 5.12 Å, 4.62 to 4.71 Å, and 3.52 to 3.57 Å".

Further, this crystal can also be described as a crystal having characteristic diffraction peaks at d-spacings of virtually 7.62 Å, 7.13 Å, 6.32 Å, 5.75 Å, 5.06 Å, 4.82 Å, 4.67 Å, 3.85 Å, and 3.54 Å in powder X-ray diffraction. It is to be noted that "having diffraction peaks at d-spacings of virtually 7.62 Å, 7.13 Å, 6.32 Å, 5.75 Å, 5.06 Å, 4.82 Å, 4.67 Å, 3.85 Å, and 3.54 Å" means "having diffraction peaks at d-spacings of 7.49 to 7.75 Å, 7.02 to 7.25 Å, 6.23 to 6.41 Å, 5.67 to 5.82 Å, 5.00 to 5.12 Å, 4.76 to 4.87 Å, 4.62 to 4.71 Å, 3.81 to 3.88 Å, and 3.52 to 3.57 Å".

Further, this crystal can also be described as a crystal having characteristic diffraction peaks at d-spacings of virtually 7.62 Å, 7.13 Å, 6.32 Å, 5.75 Å, 5.57 Å, 5.06 Å, 4.82 Å, 4.67 Å, 4.31 Å, 4.02 Å, 3.85 Å, and 3.54 Å in powder X-ray diffraction. It is to be noted that "having diffraction peaks at d-spacings of virtually 7.62 Å, 7.13 Å, 6.32 Å, 5.75 Å, 5.57 Å, 5.06 Å, 4.82 Å, 4.67 Å, 4.31 Å, 4.02 Å, 3.85 Å, and 3.54 Å" means "having diffraction peaks at d-spacings of 7.49 to 7.75 Å, 7.02 to 7.25 Å, 6.23 to 6.41 Å, 5.67 to 5.82 Å, 5.50 to 5.64 Å, 5.00 to 5.12 Å, 4.76 to 4.87 Å, 4.62 to 4.71 Å, 4.27 to 4.35 Å, 3.98 to 4.05 Å, 3.81 to 3.88 Å, and 3.52 to 3.57 Å".

Further, this crystal can also be described as a crystal having absorption peaks at wave numbers ($v_{max}$±18 cm$^{-1}$) of virtually 743 cm$^{-1}$ and 3017 cm$^{-1}$ in its infrared absorption spectrum.

Further, this crystal can also be described as a crystal having absorption peaks at wave numbers ($v_{max}$±18 cm$^{-1}$) of virtually 743 cm$^{-1}$, 814 cm$^{-1}$, 1150 cm$^{-1}$, 1462 cm$^{-1}$, and 3017 cm$^{-1}$ in its infrared absorption spectrum.

Further, this crystal can also be described as a crystal having absorption peaks at wave numbers ($v_{max}$±18 cm$^{-1}$) of virtually 743 cm$^{-1}$, 814 cm$^{-1}$, 889 cm$^{-1}$, 1084 cm$^{-1}$, 1150 cm$^{-1}$, 1325 cm$^{-1}$, 1462 cm$^{-1}$, 2949 cm$^{-1}$, and 3017 cm$^{-1}$ in its infrared absorption spectrum.

Further, this crystal can also be described as a crystal having absorption peaks at wave numbers ($v_{max}$±18 cm$^{-1}$) of virtually 569 cm$^{-1}$, 743 cm$^{-1}$, 814 cm$^{-1}$, 889 cm$^{-1}$, 905 cm$^{-1}$, 1084 cm$^{-1}$, 1111 cm$^{-1}$, 1150 cm$^{-1}$, 1325 cm$^{-1}$, 1462 cm$^{-1}$, 2949 cm$^{-1}$, and 3017 cm$^{-1}$ in its infrared absorption spectrum.

One embodiment of the present invention provides a crystal of N-(3-{(1R,5S,6r)-6-ethyl-3-[(2-methoxy-2,3-dihydro-1H-inden-2-yl)methyl]-3-azabicyclo[3.1.0]hexan-6-yl}phenyl)cyclopropanesulfonamide hydrobromide.

This crystal is a crystal obtained by precipitating a hydrobromide of the above-described compound using a mixed solvent of an alcohol and water.

This crystal is a crystal having a characteristic diffraction peak at a diffraction angle (2θ±0.2°) of 9.8° in powder X-ray diffraction.

Further, this crystal can also be described as a crystal having characteristic diffraction peaks at diffraction angles (2θ±0.2°) of 9.8° and 11.4° in powder X-ray diffraction.

Further, this crystal can also be described as a crystal having characteristic diffraction peaks at diffraction angles (2θ±0.2°) of 9.8° and 18.3° in powder X-ray diffraction.

Further, this crystal can also be described as a crystal having characteristic diffraction peaks at diffraction angles (2θ±0.2°) of 9.8°, 11.4°, and 18.3° in powder X-ray diffraction.

Further, this crystal can also be described as a crystal having characteristic diffraction peaks at diffraction angles (2θ±0.2°) of 9.8°, 11.4°, 18.3°, and 24.1° in powder X-ray diffraction.

Further, this crystal can also be described as a crystal having characteristic diffraction peaks at diffraction angles (2θ±0.2°) of 9.8°, 11.4°, 15.5°, 18.3°, 19.2° and 24.1° in powder X-ray diffraction.

Further, this crystal can also be described as a crystal having characteristic diffraction peaks at diffraction angles (2θ±0.2°) of 9.1°, 9.8°, 11.4°, 12.5°, 15.5°, 18.3°, 19.2°, 20.5° and 24.1° in powder X-ray diffraction.

Further, this crystal can also be described as a crystal having characteristic diffraction peaks at diffraction angles (2θ±0.2°) of 9.1°, 9.8°, 11.4°, 12.5°, 15.5°, 15.9°, 18.3°, 19.2°, 20.5°, 21.1°, 21.9° and 24.1° in powder X-ray diffraction.

Further, this crystal can also be described as a crystal having a characteristic diffraction peak at a d-spacing of virtually 9.01 Å in powder X-ray diffraction. It is to be noted that "having a diffraction peak at a d-spacing of virtually 9.01 Å" means "having a diffraction peak at a d-spacing of 8.83 to 9.20 Å".

Further, this crystal can also be described as a crystal having characteristic diffraction peaks at d-spacings of virtually 9.01 Å and 7.75 Å in powder X-ray diffraction. It is to be noted that "having diffraction peaks at d-spacings of virtually 9.01 Å and 7.75 Å" means "having diffraction peaks at d-spacings of 8.83 to 9.20 Å and 7.62 to 7.89 Å".

Further, this crystal can also be described as a crystal having characteristic diffraction peaks at d-spacings of virtually 9.01 Å and 4.84 Å in powder X-ray diffraction. It is to be noted that "having diffraction peaks at d-spacings of virtually 9.01 Å and 4.84 Å" means "having diffraction peaks at d-spacings of 8.83 to 9.20 Å and 4.79 to 4.90 Å".

Further, this crystal can also be described as a crystal having characteristic diffraction peaks at d-spacings of virtually 9.01 Å, 7.75 Å, and 4.84 Å in powder X-ray diffraction. It is to be noted that "having diffraction peaks at d-spacings of virtually 9.01 Å, 7.75 Å, and 4.84 Å" means "having diffraction peaks at d-spacings of 8.83 to 9.20 Å, 7.62 to 7.89 Å, and 4.79 to 4.90 Å".

Further, this crystal can also be described as a crystal having characteristic diffraction peaks at d-spacings of virtually 9.01 Å, 7.75 Å, 4.84 Å, and 3.69 Å in powder X-ray diffraction. It is to be noted that "having diffraction peaks at d-spacings of virtually 9.01 Å, 7.75 Å, 4.84 Å, and 3.69 Å" means "having diffraction peaks at d-spacings of 8.83 to 9.20 Å, 7.62 to 7.89 Å, 4.79 to 4.90 Å, and 3.66 to 3.72 Å".

Further, this crystal can also be described as a crystal having characteristic diffraction peaks at d-spacings of virtually 9.01 Å, 7.75 Å, 5.71 Å, 4.84 Å, 4.62 Å, and 3.69 Å in powder X-ray diffraction. It is to be noted that "having diffraction peaks at d-spacings of virtually 9.01 Å, 7.75 Å, 5.71 Å, 4.84 Å, 4.62 Å, and 3.69 Å" means "having diffraction peaks at d-spacings of 8.83 to 9.20 Å, 7.62 to 7.89 Å, 5.64 to 5.78 Å, 4.79 to 4.90 Å, 4.57 to 4.67 Å, and 3.66 to 3.72 Å".

Further, this crystal can also be described as a crystal having characteristic diffraction peaks at d-spacings of virtually 9.71 Å, 9.01 Å, 7.75 Å, 7.07 Å, 5.71 Å, 4.84 Å, 4.62 Å, 4.33 Å, and 3.69 Å in powder X-ray diffraction. It is to be noted that "having diffraction peak at d-spacings of virtually 9.71 Å, 9.01 Å, 7.75 Å, 7.07 Å, 5.71 Å, 4.84 Å, 4.62 Å, 4.33 Å, and 3.69 Å" means "having diffraction peaks at d-spacings of 9.50 to 9.92 Å, 8.83 to 9.20 Å, 7.62 to 7.89 Å, 6.96 to 7.19 Å, 5.64 to 5.78 Å, 4.79 to 4.90 Å, 4.57 to 4.67 Å, 4.29 to 4.37 Å, and 3.66 to 3.72 Å".

Further, this crystal can also be described as a crystal having characteristic diffraction peaks at d-spacings of virtually 9.71 Å, 9.01 Å, 7.75 Å, 7.07 Å, 5.71 Å, 5.57 Å, 4.84 Å, 4.62 Å, 4.33 Å, 4.21 Å, 4.05 Å, and 3.69 Å in powder X-ray diffraction. It is to be noted that "having diffraction peaks at d-spacings of virtually 9.71 Å, 9.01 Å, 7.75 Å, 7.07 Å, 5.71 Å, 5.57 Å, 4.84 Å, 4.62 Å, 4.33 Å, 4.21 Å, 4.05 Å, and 3.69 Å" means "having diffraction peaks at d-spacings of 9.50 to 9.92 Å, 8.83 to 9.20 Å, 7.62 to 7.89 Å, 6.96 to 7.19 Å, 5.64 to 5.78 Å, 5.50 to 5.64 Å, 4.79 to 4.90 Å, 4.57 to 4.67 Å, 4.29 to 4.37 Å, 4.17 to 4.25 Å, 4.02 to 4.09 Å, and 3.66 to 3.72 Å".

Further, this crystal can also be described as a crystal having characteristic absorption peaks at wave numbers ($v_{max}$±18 cm$^{-1}$) of virtually 743 cm$^{-1}$ and 3049 cm$^{-1}$ in its infrared absorption spectrum.

Further, this crystal can also be described as a crystal having characteristic absorption peaks at wave numbers ($v_{max}$±18 cm$^{-1}$) of virtually 743 cm$^{-1}$, 781 cm$^{-1}$, 1148 cm$^{-1}$, 1458 cm$^{-1}$, and 3049 cm$^{-1}$ in its infrared absorption spectrum.

Further, this crystal can also be described as a crystal having characteristic absorption peaks at wave numbers ($v_{max}$±18 cm$^{-1}$) of virtually 743 cm$^{-1}$, 781 cm$^{-1}$, 889 cm$^{-1}$, 1084 cm$^{-1}$, 1148 cm$^{-1}$, 1325 cm$^{-1}$, 1458 cm$^{-1}$, 2965 cm$^{-1}$, and 3049 cm$^{-1}$ in its infrared absorption spectrum.

Further, this crystal can also be described as a crystal having characteristic absorption peaks at wave numbers ($v_{max}±18$ cm$^{-1}$) of virtually 569 cm$^{-1}$, 743 cm$^{-1}$, 781 cm$^{-1}$, 889 cm$^{-1}$, 903 cm$^{-1}$, 1084 cm$^{-1}$, 1113 cm$^{-1}$, 1148 cm$^{-1}$, 1325 cm$^{-1}$, 1458 cm$^{-1}$, 2965 cm$^{-1}$, and 3049 cm$^{-1}$ in its infrared absorption spectrum.

One embodiment of the present invention provides a crystal of N-(3-{(1R,5S,6r)-3-[3-(4,4-difluoro-1-methoxycyclohexyl)propyl]-6-ethyl-3-azabicyclo[3.1.0]hexan-6-yl}phenyl)cyclopropanesulfonamide hydrochloride.

This crystal is a crystal obtained by precipitating a hydrochloride of the above-described compound using a mixed solvent of an alcohol and water.

This crystal is a crystal having a characteristic diffraction peak at a diffraction angle (2θ±0.2°) of 16.2° in powder X-ray diffraction.

Further, this crystal can also be described as a crystal having characteristic diffraction peaks at diffraction angles (2θ±0.2°) of 8.6° and 16.2° in powder X-ray diffraction.

Further, this crystal can also be described as a crystal having characteristic diffraction peaks at diffraction angles (2θ±0.2°) of 16.2° and 27.4° in powder X-ray diffraction.

Further, this crystal can also be described as a crystal having characteristic diffraction peaks at diffraction angles (2θ±0.2°) of 8.6°, 16.2°, and 27.4° in powder X-ray diffraction.

Further, this crystal can also be described as a crystal having characteristic diffraction peaks at diffraction angles (2θ±0.2°) of 8.6°, 16.2°, 23.9°, and 27.4° in powder X-ray diffraction.

Further, this crystal can also be described as a crystal having characteristic diffraction peaks at diffraction angles (2θ±0.2°) of 8.6°, 9.0°, 16.2°, 19.4°, 23.9°, and 27.4° in powder X-ray diffraction.

Further, this crystal can also be described as a crystal having characteristic diffraction peaks at diffraction angles (2θ±0.2°) of 8.6°, 9.0°, 12.6°, 14.0°, 15.6°, 16.2°, 19.4°, 23.9°, and 27.4° in powder X-ray diffraction.

Further, this crystal can also be described as a crystal having characteristic diffraction peaks at diffraction angles (2θ±0.2°) of 8.6°, 9.0°, 12.6°, 14.0°, 14.6°, 15.6°, 16.2°, 17.2°, 19.4°, 20.0°, 23.9°, and 27.4° in powder X-ray diffraction.

Further, this crystal can also be described as a crystal having a characteristic diffraction peak at a d-spacing of virtually 5.46 Å in powder X-ray diffraction. It is to be noted that "having a diffraction peak at a d-spacing of virtually 5.46 Å" means "having a diffraction peak at a d-spacing of 5.40 to 5.53 Å".

Further, this crystal can also be described as a crystal having characteristic diffraction peaks at d-spacings of virtually 10.3 Å and 5.46 Å in powder X-ray diffraction. It is to be noted that "having diffraction peaks at d-spacings of virtually 10.3 Å and 5.46 Å" means "having diffraction peaks at d-spacings of 10.0 to 10.5 Å and 5.40 to 5.53 Å".

Further, this crystal can also be described as a crystal having characteristic diffraction peaks at d-spacings of virtually 5.46 Å and 3.25 Å in powder X-ray diffraction. It is to be noted that "having diffraction peaks at d-spacings of virtually 5.46 Å and 3.25 Å" means "having diffraction peaks at d-spacings of 5.40 to 5.53 Å and 3.23 to 3.27 Å".

Further, this crystal can also be described as a crystal having characteristic diffraction peaks at d-spacings of virtually 10.3 Å, 5.46 Å, and 3.25 Å in powder X-ray diffraction. It is to be noted that "having diffraction peaks at d-spacings of virtually 10.3 Å, 5.46 Å, and 3.25 Å" means "having diffraction peaks at d-spacings of 10.0 to 10.5 Å, 5.40 to 5.53 Å, and 3.23 to 3.27 Å".

Further, this crystal can also be described as a crystal having characteristic diffraction peaks at d-spacings of virtually 10.3 Å, 5.46 Å, 3.72 Å, and 3.25 Å in powder X-ray diffraction. It is to be noted that "having diffraction peaks at d-spacings of virtually 10.3 Å, 5.46 Å, 3.72 Å, and 3.25 Å" means "having diffraction peaks at d-spacings of 10.0 to 10.5 Å, 5.40 to 5.53 Å, 3.69 to 3.75 Å, and 3.23 to 3.27 Å".

Further, this crystal can also be described as a crystal having characteristic diffraction peaks at d-spacings of virtually 10.3 Å, 9.81 Å, 5.46 Å, 4.57 Å, 3.72 Å, and 3.25 Å in powder X-ray diffraction. It is to be noted that "having diffraction peaks at d-spacings of virtually 10.3 Å, 9.81 Å, 5.46 Å, 4.57 Å, 3.72 Å, and 3.25 Å" means "having diffraction peaks at d-spacings of 10.0 to 10.5 Å, 9.60 to 10.0 Å, 5.40 to 5.53 Å, 4.52 to 4.62 Å, 3.69 to 3.75 Å, and 3.23 to 3.27 Å".

Further, this crystal can also be described as a crystal having characteristic diffraction peaks at d-spacings of virtually 10.3 Å, 9.81 Å, 7.02 Å, 6.32 Å, 5.67 Å, 5.46 Å, 4.57 Å, 3.72 Å, and 3.25 Å in powder X-ray diffraction. It is to be noted that "having diffraction peaks at d-spacings of virtually 10.3 Å, 9.81 Å, 7.02 Å, 6.32 Å, 5.67 Å, 5.46 Å, 4.57 Å, 3.72 Å, and 3.25 Å" means "having diffraction peaks at d-spacings of 10.0 to 10.5 Å, 9.60 to 10.0 Å, 6.91 to 7.13 Å, 6.23 to 6.41 Å, 5.60 to 5.75 Å, 5.40 to 5.53 Å, 4.52 to 4.62 Å, 3.69 to 3.75 Å, and 3.23 to 3.27 Å".

Further, this crystal can also be described as a crystal having characteristic diffraction peaks at d-spacings of virtually 10.3 Å, 9.81 Å, 7.02 Å, 6.32 Å, 6.06 Å, 5.67 Å, 5.46 Å, 5.15 Å, 4.57 Å, 4.43 Å, 3.72 Å, and 3.25 Å in powder X-ray diffraction. It is to be noted that "having diffraction peaks at d-spacings of virtually 10.3 Å, 9.81 Å, 7.02 Å, 6.32 Å, 6.06 Å, 5.67 Å, 5.46 Å, 5.15 Å, 4.57 Å, 4.43 Å, 3.72 Å, and 3.25 Å" means "having diffraction peaks at d-spacings of 10.0 to 10.5 Å, 9.60 to 10.0 Å, 6.91 to 7.13 Å, 6.23 to 6.41 Å, 5.98 to 6.14 Å, 5.60 to 5.75 Å, 5.40 to 5.53 Å, 5.09 to 5.21 Å, 4.52 to 4.62 Å, 4.39 to 4.48 Å, 3.69 to 3.75 Å, and 3.23 to 3.27 Å".

Further, this crystal can also be described as a crystal having characteristic absorption peaks at wave numbers ($v_{max}±18$ cm$^{-1}$) of virtually 706 cm$^{-1}$ and 2941 cm$^{-1}$ in its infrared absorption spectrum.

Further, this crystal can also be described as a crystal having characteristic absorption peaks at wave numbers ($v_{max}±18$ cm$^{-1}$) of virtually 706 cm$^{-1}$, 1148 cm$^{-1}$, 1477 cm$^{-1}$, 1607 cm$^{-1}$, and 2941 cm$^{-1}$ in its infrared absorption spectrum.

Further, this crystal can also be described as a crystal having characteristic absorption peaks at wave numbers ($v_{max}±18$ cm$^{-1}$) of virtually 706 cm$^{-1}$, 746 cm$^{-1}$, 1076 cm$^{-1}$, 1148 cm$^{-1}$, 1331 cm$^{-1}$, 1477 cm$^{-1}$, 1607 cm$^{-1}$, 2453 cm$^{-1}$, and 2941 cm$^{-1}$ in its infrared absorption spectrum.

Further, this crystal can also be described as a crystal having characteristic absorption peaks at wave numbers ($v_{max}±18$ cm$^{-1}$) of virtually 567 cm$^{-1}$, 706 cm$^{-1}$, 746 cm$^{-1}$, 891 cm$^{-1}$, 1040 cm$^{-1}$, 1076 cm$^{-1}$, 1148 cm$^{-1}$, 1331 cm$^{-1}$, 1477 cm$^{-1}$, 1607 cm$^{-1}$, 2453 cm$^{-1}$, and 2941 cm$^{-1}$ in its infrared absorption spectrum.

One embodiment of the present invention provides a crystal of N-(3-{(1R,5S,6r)-3-[3-(4,4-difluoro-1-methoxycyclohexyl)propyl]-6-ethyl-3-azabicyclo[3.1.0]hexan-6-yl}phenyl)cyclopropanesulfonamide oxalate.

This crystal is a crystal obtained by precipitating an oxalate of the above-described compound using a mixed solvent of an alcohol and water.

This crystal is a crystal having a characteristic diffraction peak at a diffraction angle (2θ±0.2°) of 9.5° in powder X-ray diffraction.

Further, this crystal can also be described as a crystal having characteristic diffraction peaks at diffraction angles (2θ±0.2°) of 9.5° and 10.3° in powder X-ray diffraction.

Further, this crystal can also be described as a crystal having characteristic diffraction peaks at diffraction angles (2θ±0.2°) of 9.5° and 23.8° in powder X-ray diffraction.

Further, this crystal can also be described as a crystal having characteristic diffraction peaks at diffraction angles (2θ±0.2°) of 9.5°, 10.3°, and 23.8° in powder X-ray diffraction.

Further, this crystal can also be described as a crystal having characteristic diffraction peaks at diffraction angles (2θ±0.2°) of 9.5°, 10.3°, 23.8°, and 25.1° in powder X-ray diffraction.

Further, this crystal can also be described as a crystal having characteristic diffraction peaks at diffraction angles (2θ±0.2°) of 9.5°, 10.3°, 10.7°, 19.0°, 23.8°, and 25.1° in powder X-ray diffraction.

Further, this crystal can also be described as a crystal having characteristic diffraction peaks at diffraction angles (2θ±0.2°) of 9.5°, 10.3°, 10.7°, 17.6°, 18.4°, 19.0°, 20.6°, 23.8° and 25.1° in powder X-ray diffraction.

Further, this crystal can also be described as a crystal having characteristic diffraction peaks at diffraction angles (2θ±0.2°) of 9.5°, 10.3°, 10.7°, 13.9°, 16.7°, 16.9°, 17.6°, 18.4°, 19.0°, 20.6°, 23.8°, and 25.1° in powder X-ray diffraction.

Further, this crystal can also be described as a crystal having a characteristic diffraction peak at a d-spacing of virtually 9.30 Å in powder X-ray diffraction. It is to be noted that "having a diffraction peak at a d-spacing of virtually 9.30 Å" means "having a diffraction peak at a d-spacing of 9.11 to 9.50 Å".

Further, this crystal can also be described as a crystal having characteristic diffraction peaks at d-spacings of virtually 9.30 Å and 8.58 Å in powder X-ray diffraction. It is to be noted that "having diffraction peaks at d-spacings of virtually 9.30 Å and 8.58 Å" means "having diffraction peaks at d-spacings of 9.11 to 9.50 Å and 8.42 to 8.75 Å".

Further, this crystal can also be described as a crystal having characteristic diffraction peaks at d-spacings of virtually 9.30 Å and 3.73 Å in powder X-ray diffraction. It is to be noted that "having diffraction peaks at d-spacings of virtually 9.30 Å and 3.73 Å" means "having diffraction peaks at d-spacings of 9.11 to 9.50 Å and 3.70 to 3.77 Å".

Further, this crystal can also be described as a crystal having characteristic diffraction peaks at d-spacings of virtually 9.30 Å, 8.58 Å, and 3.73 Å in powder X-ray diffraction. It is to be noted that "having diffraction peaks at d-spacings of virtually 9.30 Å, 8.58 Å, and 3.73 Å" means "having diffraction peaks at d-spacings of 9.11 to 9.50 Å, 8.42 to 8.75 Å, and 3.70 to 3.77 Å".

Further, this crystal can also be described as a crystal having characteristic diffraction peaks at d-spacings of virtually 9.30 Å, 8.58 Å, 3.73 Å, and 3.54 Å in powder X-ray diffraction. It is to be noted that "having diffraction peaks at d-spacings of virtually 9.30 Å, 8.58 Å, 3.73 Å, and 3.54 Å" means "having diffraction peaks at d-spacings of 9.11 to 9.50 Å, 8.42 to 8.75 Å, 3.70 to 3.77 Å, and 3.52 to 3.57 Å".

Further, this crystal can also be described as a crystal having characteristic diffraction peaks at d-spacings of virtually 9.30 Å, 8.58 Å, 8.26 Å, 4.67 Å, 3.73 Å, and 3.54 Å in powder X-ray diffraction. It is to be noted that "having diffraction peaks at d-spacings of virtually 9.30 Å, 8.58 Å, 8.26 Å, 4.67 Å, 3.73 Å, and 3.54 Å" means "having diffraction peaks at d-spacings of 9.11 to 9.50 Å, 8.42 to 8.75 Å, 8.11 to 8.42 Å, 4.62 to 4.71 Å, 3.70 to 3.77 Å, and 3.52 to 3.57 Å".

Further, this crystal can also be described as a crystal having characteristic diffraction peaks at d-spacings of virtually 9.30 Å, 8.58 Å, 8.26 Å, 5.03 Å, 4.82 Å, 4.67 Å, 4.31 Å, 3.73 Å, and 3.54 Å in powder X-ray diffraction. It is to be noted that "having diffraction peaks at d-spacings of virtually 9.30 Å, 8.58 Å, 8.26 Å, 5.03 Å, 4.82 Å, 4.67 Å, 4.31 Å, 3.73 Å, and 3.54 Å" means "having diffraction peaks at d-spacings of 9.11 to 9.50 Å, 8.42 to 8.75 Å, 8.11 to 8.42 Å, 4.98 to 5.09 Å, 4.76 to 4.87 Å, 4.62 to 4.71 Å, 4.27 to 4.35 Å, 3.70 to 3.77 Å, and 3.52 to 3.57 Å".

Further, this crystal can also be described as a crystal having characteristic diffraction peaks at d-spacings of virtually 9.30 Å, 8.58 Å, 8.26 Å, 6.36 Å, 5.30 Å, 5.24 Å, 5.03 Å, 4.82 Å, 4.67 Å, 4.31 Å, 3.73 Å, and 3.54 Å in powder X-ray diffraction. It is to be noted that "having diffraction peaks at d-spacings of virtually 9.30 Å, 8.58 Å, 8.26 Å, 6.36 Å, 5.30 Å, 5.24 Å, 5.03 Å, 4.82 Å, 4.67 Å, 4.31 Å, 3.73 Å, and 3.54 Å" means "having diffraction peaks at d-spacings of 9.11 to 9.50 Å, 8.42 to 8.75 Å, 8.11 to 8.42 Å, 6.27 to 6.46 Å, 5.24 to 5.37 Å, 5.18 to 5.30 Å, 4.98 to 5.09 Å, 4.76 to 4.87 Å, 4.62 to 4.71 Å, 4.27 to 4.35 Å, 3.70 to 3.77 Å, and 3.52 to 3.57 Å.

Further, this crystal can also be described as a crystal having characteristic absorption peaks at wave numbers ($\nu_{max}\pm18$ cm$^{-1}$) of virtually 712 cm$^{-1}$ and 3254 cm$^{-1}$ in its infrared absorption spectrum.

Further, this crystal can also be described as a crystal having characteristic absorption peaks at wave numbers ($\nu_{max}\pm18$ cm$^{-1}$) of virtually 712 cm$^{-1}$, 1157 cm$^{-1}$, 1458 cm$^{-1}$, 1607 cm$^{-1}$, and 3254 cm$^{-1}$ in its infrared absorption spectrum.

Further, this crystal can also be described as a crystal having characteristic absorption peaks at wave numbers ($\nu_{max}\pm18$ cm$^{-1}$) of virtually 712 cm$^{-1}$, 772 cm$^{-1}$, 1078 cm$^{-1}$, 1157 cm$^{-1}$, 1331 cm$^{-1}$, 1458 cm$^{-1}$, 1607 cm$^{-1}$, 2938 cm$^{-1}$, and 3254 cm$^{-1}$ in its infrared absorption spectrum.

Further, this crystal can also be described as a crystal having characteristic absorption peaks at wave numbers ($\nu_{max}\pm18$ cm$^{-1}$) of virtually 567 cm$^{-1}$, 712 cm$^{-1}$, 772 cm$^{-1}$, 889 cm$^{-1}$, 1038 cm$^{-1}$, 1078 cm$^{-1}$, 1157 cm$^{-1}$, 1331 cm$^{-1}$, 1458 cm$^{-1}$, 1607 cm$^{-1}$, 2938 cm$^{-1}$, and 3254 cm$^{-1}$ in its infrared absorption spectrum.

One embodiment of the present invention provides a crystal of N-(3-{(1R,5S,6r)-3-[3-(4,4-difluorocyclohexyl)propyl]-6-ethyl-3-azabicyclo[3.1.0]hexan-6-yl}phenyl)cyclopropanesulfonamide hydrobromide.

This crystal is a crystal obtained by precipitating a hydrobromide of the above-described compound using a mixed solvent of an alcohol and water.

This crystal is a crystal having a characteristic diffraction peak at a diffraction angle (2θ±0.2°) of 9.1° in powder X-ray diffraction.

Further, this crystal can also be described as a crystal having characteristic diffraction peaks at diffraction angles (2θ±0.2°) of 9.1° and 14.5° in powder X-ray diffraction.

Further, this crystal can also be described as a crystal having characteristic diffraction peaks at diffraction angles (2θ±0.2°) of 9.1° and 17.1° in powder X-ray diffraction.

Further, this crystal can also be described as a crystal having characteristic diffraction peaks at diffraction angles (2θ±0.2°) of 9.1°, 14.5° and 17.1° in powder X-ray diffraction.

Further, this crystal can also be described as a crystal having characteristic diffraction peaks at diffraction angles (2θ±0.2°) of 9.1°, 14.5°, 17.1°, and 25.2° in powder X-ray diffraction.

Further, this crystal can also be described as a crystal having characteristic diffraction peaks at diffraction angles (2θ±0.2°) of 9.1°, 14.5°, 16.9°, 17.1°, 19.6°, and 25.2° in powder X-ray diffraction.

Further, this crystal can also be described as a crystal having characteristic diffraction peaks at diffraction angles (2θ±0.2°) of 9.1°, 9.8°, 14.5°, 16.2°, 16.9°, 17.1°, 19.6°, 20.2° and 25.2° in powder X-ray diffraction.

Further, this crystal can also be described as a crystal having characteristic diffraction peaks at diffraction angles (2θ±0.2°) of 7.2°, 9.1°, 9.8°, 14.5°, 16.2°, 16.9°, 17.1°, 18.6°, 19.6°, 20.2°, 23.3°, and 25.2° in powder X-ray diffraction.

Further, this crystal can also be described as a crystal having a characteristic diffraction peak at a d-spacing of virtually 9.71 Å in powder X-ray diffraction. It is to be noted that "having a diffraction peak at a d-spacing of virtually 9.71 Å" means "having a diffraction peak at a d-spacing of 9.50 to 9.92 Å".

Further, this crystal can also be described as a crystal having characteristic diffraction peaks at d-spacings of virtually 9.71 Å and 6.10 Å in powder X-ray diffraction. It is to be noted that "having diffraction peaks at d-spacings of virtually 9.71 Å and 6.10 Å" means "having diffraction peaks at d-spacings of 9.50 to 9.92 Å and 6.02 to 6.19 Å".

Further, this crystal can also be described as a crystal having characteristic diffraction peaks at d-spacings of virtually 9.71 Å and 5.18 Å in powder X-ray diffraction. It is to be noted that "having diffraction peaks at d-spacings of virtually 9.71 Å and 5.18 Å" means "having diffraction peaks at d-spacings of 9.50 to 9.92 Å and 5.12 to 5.24 Å".

Further, this crystal can also be described as a crystal having characteristic diffraction peaks at d-spacings of virtually 9.71 Å, 6.10 Å, and 5.18 Å in powder X-ray diffraction. It is to be noted that "having diffraction peaks at d-spacings of virtually 9.71 Å, 6.10 Å, and 5.18 Å" means "having diffraction peaks at d-spacings of 9.50 to 9.92 Å, 6.02 to 6.19 Å, and 5.12 to 5.24 Å".

Further, this crystal can also be described as a crystal having characteristic diffraction peaks at d-spacings of virtually 9.71 Å, 6.10 Å, 5.18 Å, and 3.53 Å in powder X-ray diffraction. It is to be noted that "having diffraction peaks at d-spacings of virtually 9.71 Å, 6.10 Å, 5.18 Å, and 3.53 Å" means "having diffraction peaks at d-spacings of 9.50 to 9.92 Å, 6.02 to 6.19 Å, 5.12 to 5.24 Å and 3.50 to 3.56 Å".

Further, this crystal can also be described as a crystal having characteristic diffraction peaks at d-spacings of virtually 9.71 Å, 6.10 Å, 5.24 Å, 5.18 Å, 4.52 Å, and 3.53 Å in powder X-ray diffraction. It is to be noted that "having diffraction peaks at d-spacings of virtually 9.71 Å, 6.10 Å, 5.24 Å, 5.18 Å, 4.52 Å, and 3.53 Å" means "having diffraction peaks at d-spacings of 9.50 to 9.92 Å, 6.02 to 6.19 Å, 5.18 to 5.30 Å, 5.12 to 5.24 Å, 4.48 to 4.57 Å, and 3.50 to 3.56 Å".

Further, this crystal can also be described as a crystal having characteristic diffraction peaks at d-spacings of virtually 9.71 Å, 9.01 Å, 6.10 Å, 5.46 Å, 5.24 Å, 5.18 Å, 4.52 Å, 4.39 Å, and 3.53 Å in powder X-ray diffraction. It is to be noted that "having diffraction peaks at d-spacings of virtually 9.71 Å, 9.01 Å, 6.10 Å, 5.46 Å, 5.24 Å, 5.18 Å, 4.52 Å, 4.39 Å, and 3.53 Å" means "having diffraction peaks at d-spacings of 9.50 to 9.92 Å, 8.83 to 9.20 Å, 6.02 to 6.19 Å, 5.40 to 5.53 Å, 5.18 to 5.30 Å, 5.12 to 5.24 Å, 4.48 to 4.57 Å, 4.35 to 4.43 Å, and 3.50 to 3.56 Å".

Further, this crystal can also be described as a crystal having characteristic diffraction peaks at d-spacings of virtually 12.3 Å, 9.71 Å, 9.01 Å, 6.10 Å, 5.46 Å, 5.24 Å, 5.18 Å, 4.76 Å, 4.52 Å, 4.39 Å, 3.81 Å, and 3.53 Å in powder X-ray diffraction. It is to be noted that "having diffraction peaks at d-spacings of virtually 12.3 Å, 9.71 Å, 9.01 Å, 6.10 Å, 5.46 Å, 5.24 Å, 5.18 Å, 4.76 Å, 4.52 Å, 4.39 Å, 3.81 Å, and 3.53 Å" means "having diffraction peaks at d-spacings of 11.9 to 12.6 Å, 9.50 to 9.92 Å, 8.83 to 9.20 Å, 6.02 to 6.19 Å, 5.40 to 5.53 Å, 5.18 to 5.30 Å, 5.12 to 5.24 Å, 4.71 to 4.82 Å, 4.48 to 4.57 Å, 4.35 to 4.43 Å, 3.78 to 3.85 Å, and 3.50 to 3.56 Å".

Further, this crystal can also be described as a crystal having characteristic absorption peaks at wave numbers ($v_{max}$±18 cm$^{-1}$) of virtually 733 cm$^{-1}$ and 3071 cm$^{-1}$ in its infrared absorption spectrum.

Further, this crystal can also be described as a crystal having characteristic absorption peaks at wave numbers ($v_{max}$±18 cm$^{-1}$) of 733 cm$^{-1}$, 889 cm$^{-1}$, 1152 cm$^{-1}$, 1605 cm$^{-1}$, and 3071 cm$^{-1}$ in its infrared absorption spectrum.

Further, this crystal can also be described as a crystal having characteristic absorption peaks at wave numbers ($v_{max}$±18 cm$^{-1}$) of virtually 733 cm$^{-1}$, 810 cm$^{-1}$, 889 cm$^{-1}$, 1152 cm$^{-1}$, 1331 cm$^{-1}$, 1464 cm$^{-1}$, 1605 cm$^{-1}$, 2936 cm$^{-1}$, and 3071 cm$^{-1}$ in its infrared absorption spectrum.

Further, this crystal can also be described as a crystal having characteristic absorption peaks at wave numbers ($v_{max}$±18 cm$^{-1}$) of virtually 567 cm$^{-1}$, 733 cm$^{-1}$, 810 cm$^{-1}$, 889 cm$^{-1}$, 970 cm$^{-1}$, 1043 cm$^{-1}$, 1152 cm$^{-1}$, 1331 cm$^{-1}$, 1464 cm$^{-1}$, 1605 cm$^{-1}$, 2936 cm$^{-1}$, and 3071 cm$^{-1}$ in its infrared absorption spectrum.

One embodiment of the present invention provides a crystal of N-(3-{(1R,5S,6r)-3-[3-(4,4-difluorocyclohexyl)propyl]-6-ethyl-3-azabicyclo[3.1.0]hexan-6-yl}phenyl)cyclopropanesulfonamide oxalate.

This crystal is a crystal obtained by precipitating an oxalate of the above-described compound using a ketone as a solvent.

This crystal is a crystal having a characteristic diffraction peak at a diffraction angle (2θ±0.2°) of 9.7° in powder X-ray diffraction.

Further, this crystal can also be described as a crystal having characteristic diffraction peaks at diffraction angles (2θ±0.2°) of 9.7° and 14.5° in powder X-ray diffraction.

Further, this crystal can also be described as a crystal having characteristic diffraction peaks at diffraction angles (2θ±0.2°) of 9.7° and 17.3° in powder X-ray diffraction.

Further, this crystal can also be described as a crystal having characteristic diffraction peaks at diffraction angles (2θ±0.2°) of 9.7°, 14.5°, and 17.3° in powder X-ray diffraction.

Further, this crystal can also be described as a crystal having characteristic diffraction peaks at diffraction angles (2θ±0.2°) of 9.7°, 14.5°, 17.3°, and 26.0° in powder X-ray diffraction.

Further, this crystal can also be described as a crystal having characteristic diffraction peaks at diffraction angles (2θ±0.2°) of 9.7°, 11.6°, 14.5°, 16.5°, 17.3°, and 26.0° in powder X-ray diffraction.

Further, this crystal can also be described as a crystal having characteristic diffraction peaks at diffraction angles (2θ±0.2°) of 4.8°, 9.7°, 10.3°, 11.6°, 14.5°, 15.5°, 16.5°, 17.3°, and 26.0° in powder X-ray diffraction.

Further, this crystal can also be described as a crystal having characteristic diffraction peaks at diffraction angles (2θ±0.2°) of 4.8°, 9.7°, 10.3°, 10.8°, 11.6°, 14.5°, 15.5°, 16.5°, 17.3°, 17.7°, 18.4°, and 26.0° in powder X-ray diffraction.

Further, this crystal can also be described as a crystal having a characteristic diffraction peak at a d-spacing of virtually 9.11 Å in powder X-ray diffraction. It is to be noted that "having a diffraction peak at a d-spacing of virtually 9.11 Å" means "having a diffraction peak at a d-spacing of 8.92 to 9.30 Å".

Further, this crystal can also be described as a crystal having characteristic diffraction peaks at d-spacings of virtually 9.11 Å and 6.10 Å in powder X-ray diffraction. It is to be noted that "having diffraction peaks at d-spacings of virtually 9.11 Å and 6.10 Å" means "having diffraction peaks at d-spacings of 8.92 to 9.30 Å and 6.02 to 6.19 Å".

Further, this crystal can also be described as a crystal having characteristic diffraction peaks at d-spacings of virtually 9.11 Å and 5.12 Å in powder X-ray diffraction. It is to be noted that "having diffraction peaks at d-spacings of virtually 9.11 Å and 5.12 Å" means "having diffraction peaks at d-spacings of 8.92 to 9.30 Å and 5.06 to 5.18 Å".

Further, this crystal can also be described as a crystal having characteristic diffraction peaks at d-spacings of virtually 9.11 Å, 6.10 Å, and 5.12 Å in powder X-ray diffraction. It is to be noted that "having diffraction peaks at d-spacings of virtually 9.11 Å, 6.10 Å, and 5.12 Å" means "having diffraction peaks at d-spacings of 8.92 to 9.30 Å, 6.02 to 6.19 Å, and 5.06 to 5.18 Å".

Further, this crystal can also be described as a crystal having characteristic diffraction peaks at d-spacings of virtually 9.11 Å, 6.10 Å, 5.12 Å, and 3.42 Å in powder X-ray diffraction. It is to be noted that "having diffraction peaks at d-spacings of virtually 9.11 Å, 6.10 Å, 5.12 Å, and 3.42 Å" means "having diffraction peaks at d-spacings of 8.92 to 9.30 Å, 6.02 to 6.19 Å, 5.06 to 5.18 Å and 3.40 to 3.45 Å".

Further, this crystal can also be described as a crystal having characteristic diffraction peaks at d-spacings of virtually 9.11 Å, 7.62 Å, 6.10 Å, 5.37 Å, 5.12 Å, and 3.42 Å in powder X-ray diffraction. It is to be noted that "having diffraction peaks at d-spacings of virtually 9.11 Å, 7.62 Å, 6.10 Å, 5.37 Å, 5.12 Å, and 3.42 Å" means "having diffraction peaks at d-spacings of 8.92 to 9.30 Å, 7.49 to 7.75 Å, 6.02 to 6.19 Å, 5.30 to 5.43 Å, 5.06 to 5.18 Å, and 3.40 to 3.45 Å".

Further, this crystal can also be described as a crystal having characteristic diffraction peaks at d-spacings of virtually 18.4 Å, 9.11 Å, 8.58 Å, 7.62 Å, 6.10 Å, 5.71 Å, 5.37 Å, 5.12 Å, and 3.42 Å in powder X-ray diffraction. It is to be noted that "having diffraction peaks at d-spacings of virtually 18.4 Å, 9.11 Å, 8.58 Å, 7.62 Å, 6.10 Å, 5.71 Å, 5.37 Å, 5.12 Å, and 3.42 Å" means "having diffraction peaks at d-spacings of 17.7 to 19.2 Å, 8.92 to 9.30 Å, 8.42 to 8.75 Å, 7.49 to 7.75 Å, 6.02 to 6.19 Å, 5.64 to 5.78 Å, 5.30 to 5.43 Å, 5.06 to 5.18 Å, and 3.40 to 3.45 Å".

Further, this crystal can also be described as a crystal having characteristic diffraction peaks at d-spacings of virtually 18.4 Å, 9.11 Å, 8.58 Å, 8.18 Å, 7.62 Å, 6.10 Å, 5.71 Å, 5.37 Å, 5.12 Å, 5.00 Å, 4.82 Å, and 3.42 Å in powder X-ray diffraction. It is to be noted that "having diffraction peaks at d-spacings of virtually 18.4 Å, 9.11 Å, 8.58 Å, 8.18 Å, 7.62 Å, 6.10 Å, 5.71 Å, 5.37 Å, 5.12 Å, 5.00 Å, 4.82 Å, and 3.42 Å" means "having diffraction peaks at d-spacings of 17.7 to 19.2 Å, 8.92 to 9.30 Å, 8.42 to 8.75 Å, 8.03 to 8.34 Å, 7.49 to 7.75 Å, 6.02 to 6.19 Å, 5.64 to 5.78 Å, 5.30 to 5.43 Å, 5.06 to 5.18 Å, 4.95 to 5.06 Å, 4.76 to 4.87 Å, and 3.40 to 3.45 Å".

Further, this crystal can also be described as a crystal having characteristic absorption peaks at wave numbers ($v_{max} \pm 18 \text{ cm}^{-1}$) of virtually 704 cm$^{-1}$ and 3244 cm$^{-1}$ in its infrared absorption spectrum.

Further, this crystal can also be described as a crystal having characteristic absorption peaks at wave numbers ($v_{max} \pm 18 \text{ cm}^{-1}$) of virtually 704 cm$^{-1}$, 889 cm$^{-1}$, 1152 cm$^{-1}$, 1609 cm$^{-1}$, and 3244 cm$^{-1}$ in its infrared absorption spectrum.

Further, this crystal can also be described as a crystal having characteristic absorption peaks at wave numbers ($v_{max} \pm 18 \text{ cm}^{-1}$) of virtually 704 cm$^{-1}$, 793 cm$^{-1}$, 889 cm$^{-1}$, 1152 cm$^{-1}$, 1333 cm$^{-1}$, 1464 cm$^{-1}$, 1609 cm$^{-1}$, 2936 cm$^{-1}$, and 3244 cm$^{-1}$ in its infrared absorption spectrum.

Further, this crystal can also be described as a crystal having characteristic absorption peaks at wave numbers ($v_{max} \pm 18 \text{ cm}^{-1}$) of virtually 569 cm$^{-1}$, 704 cm$^{-1}$, 793 cm$^{-1}$, 889 cm$^{-1}$, 962 cm$^{-1}$, 1040 cm$^{-1}$, 1152 cm$^{-1}$, 1333 cm$^{-1}$, 1464 cm$^{-1}$, 1609 cm$^{-1}$, 2936 cm$^{-1}$, and 3244 cm$^{-1}$ in its infrared absorption spectrum.

One embodiment of the present invention provides a pharmaceutical composition comprising the crystal according to any one of the above embodiments as an active ingredient.

The pharmaceutical composition according to the one embodiment of the present invention is intended to be used for prevention or treatment of pruritus as a disease to be treated.

Method for Producing the Compound (I)

The compound (I) can be produced by those skilled in the art by appropriately combining reactions well known in the field of organic chemistry. The present inventors have already filed a patent for the compound (I) (Application No. PCT/JP2014/80681). That is, the compound (I) can be produced on the basis of a method disclosed in the description of the patent application. More specifically, the compound (I) can be produced by the following method. Alternatively, the compound (I) may also be produced on the basis of a method disclosed in WO 2000/039089 or WO 2003/035622.

The compound (I) can be produced by, for example, the following production method.

[Production Method 1]

"Production Method 1" is a method for producing the compound (I).

[Chemical Formula 5]
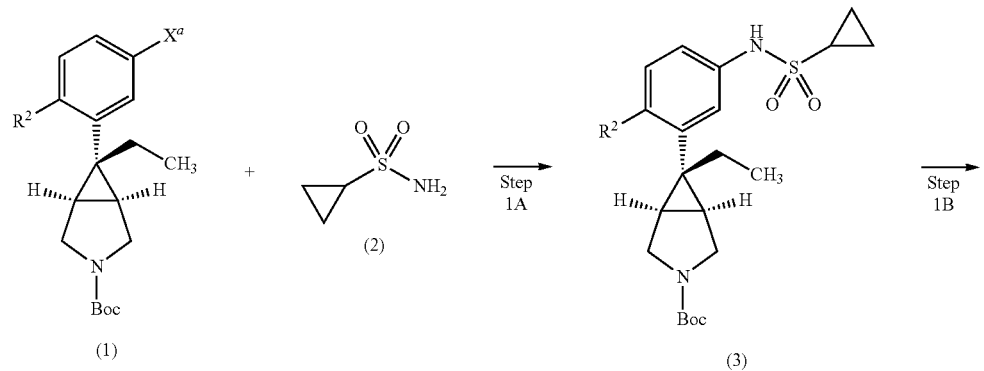
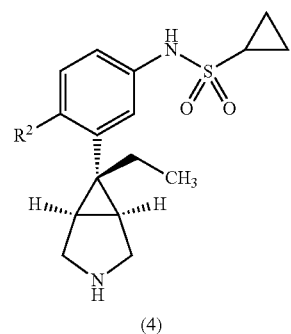
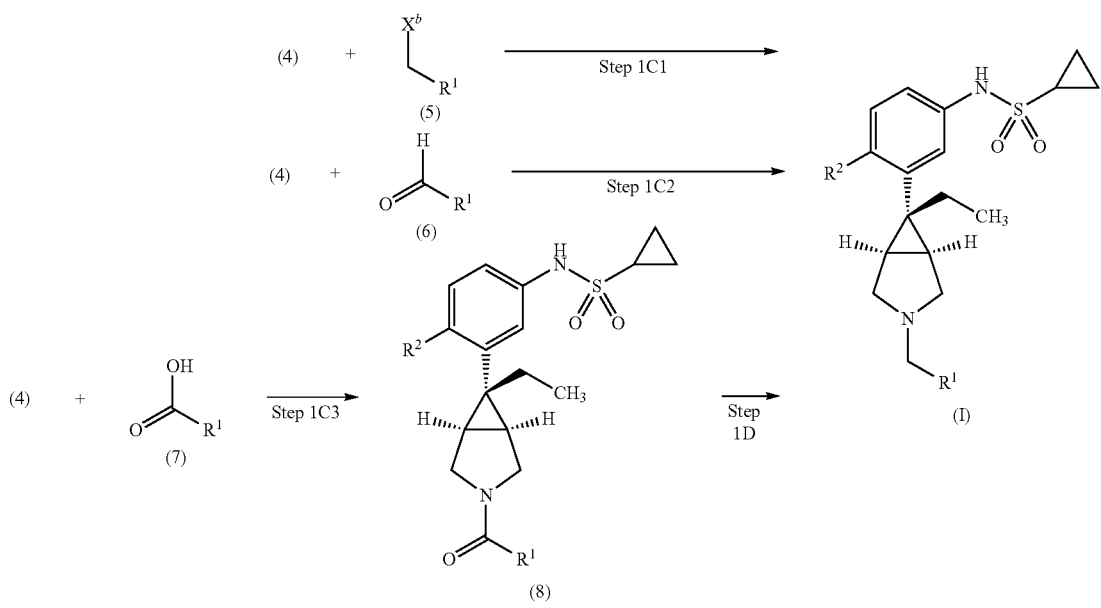

(wherein, $R^1$ is a group selected from the group consisting of:

[Chemical Formula 6]

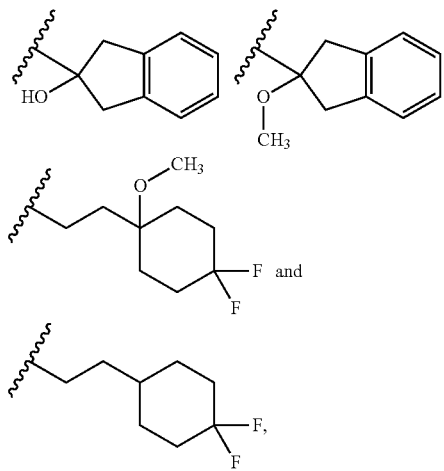

and $R^2$ is a hydrogen atom or a halogen atom, and $X^a$ is a chlorine atom, a bromine atom, an iodine atom, or a trifluoromethanesulfonyloxy group, $X^b$ is a chlorine atom, a bromine atom, an iodine atom, a methanesulfonyloxy group, a benzenesulfonyloxy group, a p-toluenesulfonyloxy group, or a trifluoromethanesulfonyloxy group, and Boc is a tert-butoxycarbonyl group).

"Step 1A" is a step in which a compound (1) and a compound (2) are reacted under an inert gas atmosphere in an inert solvent in the presence of a palladium catalyst, an organic phosphine compound, and a base to produce a compound (3). The compound (1) and the compound (2) are known, or can be produced from known compounds in accordance with known methods (the compound (1) can be produced on the basis of a method disclosed in, for example, Patent Literature 1, Patent Literature 5, WO 2009/027293, Journal of Medicinal Chemistry, 53 (2010), 2534 to 2551).

Examples of the inert gas to be used include helium, nitrogen, and argon. The inert solvent to be used is not particularly limited as long as the inert solvent does not inhibit the reaction and dissolves the raw materials to some extent. Examples of the inert solvent include: aromatic hydrocarbons such as benzene, toluene, and xylene; ethers such as 1,2-dimethoxyethane, tetrahydrofuran, 2-methyltetrahydrofuran, and 1,4-dioxane; amides such as N,N-dimethylformamide, N,N-dimethylacetamide, and N-methylpyrrolidone; sulfoxides such as dimethylsulfoxide; and mixed solvents of any two or more of them, and toluene, 2-methyltetrahydrofuran, 1,4-dioxane, or mixed solvents of any two or more of them is preferred.

Examples of the palladium catalyst to be used include: organic palladium complexes such as tetrakis(triphenylphosphine)palladium, tris(dibenzylideneacetone)dipalladium, dichlorobis(triphenylphosphine)palladium, and bis(η3-allyl-μ-chloropalladium); and palladium salts such as dichloropalladium and diacetoxypalladium, and bis(η3-allyl-μ-chloropalladium) is preferred. The amount of the palladium catalyst to be used is usually 0.0001- to 1-fold molar amount, preferably 0.005- to 0.3-fold molar amount per mole of the compound (1).

Examples of the organic phosphine compound to be used include tri-n-butylphosphine, tri-tert-butylphosphine, tricyclohexylphosphine, butyldi-1-adamantylphosphine, triphenylphosphine, tri(o-tolyl)phosphine, 1,3-bis(diphenylphosphino)propane, 2-(di-tert-butylphosphino)biphenyl, 2-(dicyclohexylphosphino)-2',6'-dimethoxy-1,1'-biphenyl (hereinafter abbreviated as SPhos), 2-(dicyclohexylphosphino)-2',4',6'-triisopropyl-1,1'-biphenyl (hereinafter abbreviated as XPhos), 2-(di-tert-butylphosphino)-2',4',6'-triisopropyl-1,1'-biphenyl (hereinafter abbreviated as tert-butyl XPhos), 2-(di-tert-butylphosphino)-3,4,5,6-tetramethyl-2',4',6'-triisopropyl-1,1'-biphenyl, 1,1'-bis(diphenylphosphino)ferrocene, 1,2,3,4,5-pentaphenyl-1'-(di-tert-butylphosphino)ferrocene, and 9,9-dimethyl-4,5-bis(diphenylphosphino)xanthene, and tert-butyl XPhos or 2-(di-tert-butylphosphino)-3,4,5,6-tetramethyl-2',4',6'-triisopropyl-1,1'-biphenyl is preferred. The amount of the organic phosphine compound to be used is usually 0.5- to 5-fold molar amount, preferably 1- to 3-fold molar amount per mole of palladium.

Examples of the base to be used include: alkali metal acetates such as sodium acetate and potassium acetate; alkali metal carbonates such as sodium carbonate, potassium carbonate and cesium carbonate; alkali metal phosphates such as trisodium phosphate and tripotassium phosphate; alkali metal alkoxides such as sodium tert-butoxide and potassium tert-butoxide; and alkali metal hydrides such as sodium hydride and potassium hydride, and potassium carbonate or cesium carbonate is preferred. The amount of the base to be used is usually 0.5- to 10-fold molar amount, preferably 1- to 5-fold molar amount per mole of the compound (1).

In this step, a fluoride may be added to promote the reaction. Examples of the fluoride to be used include potassium fluoride, cesium fluoride, tetramethylammonium fluoride, tetraethylammonium fluoride, and tetrabutylammonium fluoride. The amount of the fluoride to be used is usually 0.5- to 10-fold molar amount, preferably 1- to 5-fold molar amount per mole of the compound (1).

The amount of the compound (2) to be used is usually 0.5- to 10-fold molar amount, preferably 1- to 5-fold molar amount per mole of the compound (1).

The reaction temperature varies depending on the kinds, amounts, etc. of the raw materials and solvent used, etc., but is usually 0° C. to 150° C., preferably 50° C. to 120° C.

The reaction time varies depending on the reaction temperature, etc., but is usually 10 minutes to 120 hours, preferably 30 minutes to 48 hours.

"Step 1B" is a step in which the Boc group of the compound (3) is removed to produce a compound (4). This step can be performed on the basis of a publication (see T. W. Greene & P. G. M. Wuts, Protective Groups in Organic Synthesis 4th Ed., John Wiley & Sons, Inc., pages 582 and 725). This step is performed by, for example, treating the compound (3) with an acid in an inert solvent, but is not limited thereto.

The inert solvent to be used is not particularly limited as long as the inert solvent does not inhibit the reaction and dissolves the raw material to some extent. Examples of the inert solvent include: ethers such as diethyl ether, 1,2-dimethoxyethane, tetrahydrofuran, and 1,4-dioxane; halogenated aliphatic hydrocarbons such as methylene chloride, chloroform, and 1,2-dichloroethane; water; and mixed solvents of any two or more of them, and tetrahydrofuran, 1,4-dioxane, methylene chloride, water, or mixed solvents of any two or more of them is preferred.

Examples of the acid to be used include hydrogen chloride, hydrochloric acid, hydrobromic acid, hydroiodic acid, sulfuric acid, phosphoric acid, methanesulfonic acid, p-toluenesulfonic acid, and trifluoroacetic acid, and hydrogen chloride, hydrochloric acid, or trifluoroacetic acid is preferred. The amount of the acid to be used is usually 1- to 200-fold molar amount, preferably 5- to 100-fold molar amount per mole of the compound (3), but the acid may be used in a large excess amount as a solvent.

In this step, an anisole compound such as anisole or thioanisole may be added to promote the reaction. The amount of the anisole compound to be used is usually 1- to 200-fold molar amount, preferably 2- to 100-fold molar amount per mole of the compound (3).

The reaction temperature varies depending on the kinds, amounts, etc. of the raw material and solvent used etc., but is usually −30° C. to 150° C., preferably 0° C. to 100° C.

The reaction time varies depending on the reaction temperature etc., but is usually 10 minutes to 48 hours, preferably 30 minutes to 24 hours.

"Step 1C1" is a step in which the compound (4) and a compound (5) are reacted in an inert solvent in the presence of a base to produce the compound (I). The compound (5) is known, or can be produced from known compounds in accordance with a known method.

The inert solvent to be used is not particularly limited as long as the inert solvent does not inhibit the reaction and dissolves the raw materials to some extent. Examples of the inert solvent include: aromatic hydrocarbons such as benzene, toluene, and xylene; ethers such as diethyl ether, 1,2-dimethoxyethane, tetrahydrofuran, and 1,4-dioxane; halogenated aliphatic hydrocarbons such as methylene chloride, chloroform, and 1,2-dichloroethane; amides such as N,N-dimethylformamide, N,N-dimethylacetamide, and N-methylpyrrolidone; nitriles such as acetonitrile and propionitrile; alcohols such as methanol, ethanol, propanol, and isopropanol; and mixed solvents of any two or more of them, and ethanol is preferred.

Examples of the base to be used include: organic bases such as triethylamine, diisopropylethylamine, and pyridine; and inorganic bases such as sodium hydrogen carbonate, potassium hydrogen carbonate, sodium carbonate, and potassium carbonate, and triethylamine or diisopropylethylamine is preferred. The amount of the base to be used is usually 0.5- to 20-fold molar amount, preferably 1- to 10-fold molar amount per mole of the compound (4).

The amount of the compound (5) to be used is usually 0.2- to 10-fold molar amount, preferably 0.5- to 3-fold molar amount per mole of the compound (4).

The reaction temperature varies depending on the kinds, amounts, etc. of the raw materials and solvent used etc., but is usually −30° C. to 200° C., preferably 0° C. to 150° C.

The reaction time varies depending on the reaction temperature etc., but is usually 10 minutes to 120 hours, preferably 30 minutes to 48 hours.

"Step 1C2" is a step in which the compound (4) and a compound (6) are reacted in an inert solvent in the presence or absence of a dehydrating agent to form an imine form, and then the imine form is reduced using a boron hydride compound to produce the compound (I). The compound (6) is known, or can be produced from known compounds in accordance with a known method.

The inert solvent to be used is not particularly limited as long as the inert solvent does not inhibit the reaction and dissolves the raw materials to some extent. Examples of the inert solvent include: halogenated aliphatic saturated hydrocarbons such as methylene chloride, chloroform, and 1,2-dichloroethane; and alcohols such as methanol, ethanol, propanol, and isopropanol, and methylene chloride or 1,2-dichloroethane is preferred.

Examples of the dehydrating agent to be used include a molecular sieve (trade name) and anhydrous magnesium sulfate. The amount of the dehydrating agent to be used is usually 50 g to 2000 g, preferably 100 g to 1000 g per mole of the compound (4).

The amount of the compound (6) to be used is usually 0.2- to 10-fold molar amount, preferably 0.5- to 3-fold molar amount per mole of the compound (4). It is to be noted that when the compound (4) is an acid addition salt (e.g., a hydrochloride), a base may be added, in which case, examples of the base to be used include triethylamine and diisopropylethylamine. The amount of the base to be used is usually 0.2- to 10-fold molar amount, preferably 0.5- to 3-fold molar amount per mole of the compound (4).

The reaction temperature varies depending on the kinds, amounts, etc. of the raw materials and solvent used etc., but is usually −30° C. to 150° C., preferably 0° C. to 100° C.

The reaction time varies depending on the reaction temperature etc., but is usually 10 minutes to 48 hours, preferably 30 minutes to 24 hours.

The obtained imine form is reduced using a boron hydride compound after isolated or without being isolated. Examples of the boron hydride compound to be used include sodium borohydride, sodium cyanoborohydride, and sodium triacetoxyborohydride, and sodium triacetoxyborohydride is preferred. The amount of the boron hydride compound to be used is usually 0.5- to 10-fold molar amount, preferably 1- to 5-fold molar amount per mole of the compound (4).

In this step, the reaction for the synthesis of the imine form and the subsequent reduction reaction can be performed continuously in the same system without isolating the imine form. However, when the obtained imine form is isolated, the inert solvent to be used in the reduction reaction is not particularly limited as long as the inert solvent does not inhibit the reaction and dissolves the raw material to some extent. Examples of the inert solvent include: halogenated aliphatic hydrocarbons such as methylene chloride, chloroform, and 1,2-dichloroethane; and alcohols such as methanol, ethanol, propanol, and isopropanol, and methylene chloride or 1,2-dichloroethane is preferred.

The reaction temperature varies depending on the kinds, amounts, etc. of the raw material and solvent used etc., but is usually −30° C. to 150° C., preferably 0° C. to 100° C.

The reaction time varies depending on the reaction temperature etc., but is usually 10 minutes to 48 hours, preferably 30 minutes to 24 hours.

"Step 1C3" is a step in which the carboxy group of a compound (7) is converted to an "active form of a carboxyl group" such as an acid chloride, a mixed acid anhydride, or imidazolide in an inert solvent with the use of an agent for activating a carboxy group, and then the active form is reacted with the compound (4) in the presence of a base to produce a compound (8). It is to be noted that the "active form of a carboxy group" can be used for the reaction with the compound (4) without being isolated. The compound (7) is known, or can be produced from known compounds in accordance with a known method.

The inert solvent to be used is not particularly limited as long as the inert solvent does not inhibit the reaction and dissolves the raw materials to some extent. Examples of the inert solvent include: aromatic hydrocarbons such as benzene, toluene, and xylene; ethers such as diethyl ether, 1,2-dimethoxyethane, tetrahydrofuran, and 1,4-dioxane; halogenated aliphatic hydrocarbons such as methylene chloride, chloroform, and 1,2-dichloroethane; amides such as N,N-dimethylformamide, N,N-dimethylacetamide, and N-methylpyrrolidone; nitriles such as acetonitrile and propionitrile; and mixed solvents of any two or more of them, and methylene chloride, tetrahydrofuran, N,N-dimethylformamide, acetonitrile, or mixed solvents of any two or more of them is preferred.

Examples of the agent for activating a carboxy group to be used include: chlorides such as thionyl chloride, oxalyl chloride, phosphorus oxychloride, and phosphorus pentachloride; condensing agents such as dicyclohexylcarbodiimide (hereinafter abbreviated as DCC), 1-ethyl-3-(3-diemthylaminopropyl)carbodiimide (hereinafter abbreviated as EDC), O-(benzotriazol-1-yl)-N,N,N',N'-tetramethyluronium hexafluorophosphate (hereinafter abbreviated as HBTU), O-(benzotriazol-1-yl)-N,N,N',N'-tetramethyluronium tetrafluoroborate (hereinafter abbreviated as TBTU), O-(7-azabenzotriazole-1-yl)-N,N,N',N'-tetramethyluronium hexafluorophosphate (hereinafter abbreviated as HATU), (1-cyano-2-ethoxy-2-oxoethylideneaminooxy)dimethylaminomorpholinocarbenium hexafluorophosphate (hereinafter abbreviated as COMU), and 1,1-carbonyldiimidazole (hereinafter abbreviated as CDI); and chloroformates such as methyl chloroformate and ethyl chloroformate, and thionyl chloride or a condensing agent is preferred. The amount of the activating agent to be used is usually 0.5- to 10-fold molar amount, preferably 1- to 5-fold molar amount per mole of the compound (7).

Examples of the base to be used include: organic bases such as triethylamine, diisopropylethylamine and N,N-dimethylaminopyridine; and inorganic bases such as sodium hydrogen carbonate, potassium hydrogen carbonate, sodium carbonate, and potassium carbonate, and triethylamine, diisopropylethylamine, or N,N-dimethylaminopyridine is preferred. The amount of the base to be used is usually 0.5- to 10-fold molar amount, preferably 1- to 5-fold molar amount per mole of the compound (4).

The amount of the compound (7) to be used is usually 0.2- to 10-fold molar amount, preferably 0.5- to 3-fold molar amount per mole of the compound (4).

The reaction temperature varies depending on the kinds, amounts, etc. of the raw materials and solvent used etc., but is usually −30° C. to 200° C., preferably 0° C. to 150° C.

The reaction time varies depending on the reaction temperature etc., but is usually 10 minutes to 48 hours, preferably 30 minutes to 24 hours.

"Step 1D" is a step in which the compound (8) is reduced in an inert solvent to produce the compound (I).

The inert solvent to be used is not particularly limited as long as the inert solvent does not inhibit the reaction and dissolves the raw material to some extent. Examples of the inert solvent include: aromatic hydrocarbons such as benzene, toluene, and xylene; ethers such as diethyl ether, 1,2-dimethoxyethane, tetrahydrofuran, and 1,4-dioxane; halogenated aliphatic hydrocarbons such as methylene chloride, chloroform, and 1,2-dichloroethane; and mixed solvents of any two or more of them, and tetrahydrofuran is preferred.

Examples of a reducing agent to be used include: alkali metal borohydride compounds such as lithium borohydride and sodium borohydride; boranes such as borane-tetrahydrofuran complex, N,N-dimethylaniline borane, and dimethylsulfideborane; and lithium aluminum hydride, and sodium borohydride, borane-tetrahydrofuran complex, or lithium aluminum hydride is preferred. The amount of the reducing agent to be used is usually 0.5- to 20-fold molar amount, preferably 1- to 10-fold molar amount per mole of the compound (8).

When sodium borohydride is used as the reducing agent, adding of boron trifluoride-diethyl ether complex is preferred. The amount of boron trifluoride-diethyl ether complex to be used is usually 0.2- to 10-fold molar amount, preferably 0.5- to 3-fold molar amount per mole of sodium borohydride.

The reaction temperature varies depending on the kinds, amounts, etc. of the raw material and solvent used etc., but is usually −30° C. to 150° C., preferably 0° C. to 100° C.

The reaction time varies depending on the reaction temperature etc., but is usually 10 minutes to 48 hours, preferably 30 minutes to 24 hours.

Method for Producing Crystal of Salt of Compound (I)

A crystal of a salt of the compound (I) can be produced by mixing the compound (I) and an acid selected from the group consisting of hydrochloric acid, hydrobromic acid, and oxalic acid in a solvent and crystallizing the resulting salt.

The crystal of a salt of the compound (I) can be produced by, for example, the following procedure:
 (i) adding a solvent to the compound (I);
 (ii) adding an acid to a solution obtained in (i) and stirring a reaction mixture;
 (iii) optionally heating or cooling the reaction mixture obtained in (ii), distilling away the solvent, adding a poor solvent, or adding a desired crystal (seed crystal) of the salt; and
 (iv) collecting a precipitated solid by filtration and then drying the solid.

Examples of the solvent to be used for producing a salt and a crystal include: alcohols such as methanol, ethanol, 1-propanol, and 2-propanol; ethers such as diethyl ether, tetrahydrofuran, and 1,4-dioxane; ketones such as acetone, diethyl ketone, and methyl ethyl ketone; acetonitrile; dimethylsulfoxide; amides such as N,N-dimethylformamide and N,N-dimethylacetamide; and water. These solvents may be used singly or in combination of two or more of them. A mixed solvent of an alcohol and water is preferably used for producing the crystal according to the present invention.

The mixing ratio (volume ratio) between an alcohol and water is, for example, 1:20 to 20:1, preferably 1:10 to 10:1.

The amount of the solvent to be used is, for example, 50 mL to 50 L, preferably 100 mL to 20 L per mole of the compound (I).

The hydrochloric acid used for producing a hydrochloride may be hydrogen chloride gas or a solution prepared by dissolving hydrogen chloride gas in water or an organic solvent. The hydrobromic acid used for producing a hydrobromide may be hydrogen bromide gas or a solution prepared by dissolving hydrogen bromide gas in water or an organic solvent. Here, the organic solvent for dissolving the acid may be an alcohol such as methanol, ethanol, 1-propanol, or 2-propanol, or an ether such as diethyl ether, tetrahydrofuran, or 1,4-dioxane. As the oxalic acid used for producing an oxalate, solid oxalic acid may be used as it is, oxalic acid powder prepared by grinding solid oxalic acid may be used, or a solution prepared by dissolving oxalic acid in a solvent may be used. When oxalic acid is used as the acid, a solution prepared by dissolving it in a solvent is preferably used.

The amount of the acid to be used is, for example, 0.5 to 20 moles per mole of the compound (I). It is to be noted that since oxalic acid is a dibasic acid, there is a case where two molecules of the compound (I) and one molecule of oxalic acid form a salt, in which case the required amount of oxalic acid is half of that of hydrochloric acid or the like.

The temperature at which the acid is added to the reaction solution is, for example, −20 to 150° C., preferably 0 to 100° C.

When the crystal of a salt of the compound (I) is produced, crystallization may be performed after a produced salt of the compound (I) is once isolated. A solvent or the like used in this case is the same as that described above with reference to the solvent used for producing a salt and a crystal, but the same solvent or different solvents may be used before and after isolation of the salt.

When the crystal is produced, for example, the reaction mixture may be heated or cooled, the solvent may be distilled away, or a poor solvent may be added after the production of a salt.

The salt may be once completely dissolved or may be partially dissolved. When the salt is once completely dissolved, impurities may be removed by filtration after dissolution.

When the reaction mixture is heated, the temperature of the reaction mixture is, for example, room temperature to 150° C., preferably room temperature to 100° C.

When the reaction mixture is cooled, the temperature of the reaction mixture is, for example, −20 to 80° C., preferably 0 to 60° C.

The reaction mixture may be slowly cooled by allowing it to stand at room temperature, and the cooling rate is not particularly limited, but is, for example, −0.1 to −10° C./min.

When the crystal is produced, a poor solvent may be added. The poor solvent only needs to be a solvent having a low ability to dissolve a desired crystal. Examples of such a poor solvent include an alcohol, water, and a mixed solvent of an alcohol and water, and water is preferred.

When the crystal is produced, part of a desired crystal separately prepared as a seed crystal may be added. The amount of the seed crystal to be added is, for example, 0.00001 to 0.1 moles, preferably 0.00005 to 0.05 moles per mole of the compound (I).

When the crystal is produced, repetition of heating and cooling cycles (temperature swing) may be performed to precipitate a larger amount of the crystal or to grow the precipitated crystal.

The crystal precipitated in the solution is collected by filtration and dried in accordance with a conventional method. In this way, a desired crystal is obtained.

Hereinbelow, more preferred methods for producing crystals (A) to (H) of salts of the compound (I) will be supplementarily described, respectively. The crystals of salts of the compound (I) are indicated by (A) to (H), respectively.

(A) Method for producing crystal of N-(3-{(1R,5S,6r)-6-ethyl-3-[(2-hydroxy-2,3-dihydro-1H-inden-2-yl)methyl]-3-azabicyclo[3.1.0]hexan-6-yl}-4-fluorophenyl)cyclopropanesulfonamide (hereinafter, referred to as a compound (I)-1) hydrochloride This crystal can be produced in accordance with the above-described method for producing a crystal of a salt of the compound (I).

The solvent to be used for producing a salt and a crystal is not particularly limited as long as the solvent can dissolve or suspend the compound (I)-1, and preferred examples of such a solvent include: alcohols such as methanol, ethanol, 1-propanol, and 2-propanol; water; and mixed solvents of two or more of them. The solvent is more preferably a mixed solvent of an alcohol and water, particularly preferably a mixed solvent of ethanol and water. The mixing ratio (volume ratio) between an alcohol and water is preferably 1:10 to 10:1, more preferably 1:5 to 6:1. The amount of the solvent to be used is preferably 100 mL to 20 L, more preferably 500 mL to 10 L per mole of the compound (I)-1.

Hydrochloric acid to be added is preferably one prepared by dissolving hydrogen chloride gas in water. The amount of hydrochloric acid to be used is preferably 0.7 to 2 moles, more preferably 0.9 to 1.3 moles per mole of the compound (I)-1. When hydrochloric acid is added, the compound (I)-1 may be either dissolved or suspended, but is preferably dissolved. The reaction mixture may be heated to dissolve the compound (I)-1, in which case the heating temperature is preferably room temperature to 100° C., more preferably room temperature to 80° C. The temperature at which hydrochloric acid is added is preferably 0 to 100° C., more preferably 5 to 80° C.

The compound (I)-1 hydrochloride is preferably dissolved once before the crystal is produced. When the compound (I)-1 hydrochloride is dissolved by heating, the temperature of the reaction mixture is preferably room temperature to 100° C., more preferably room temperature to 80° C.

When the crystal is produced, the reaction mixture may be cooled. In this case, the temperature of the reaction mixture is preferably 0 to 60° C., more preferably 5 to 50° C.

When the crystal is produced, a crystal (A) separately prepared as a seed crystal can be added. The amount of the seed crystal to be added is preferably 0.00005 to 0.05 moles, more preferably 0.0001 to 0.02 moles per mole of the compound (I)-1 hydrochloride.

(B) Method for producing crystal of N-(3-{(1R,5S,6r)-6-ethyl-3-[(2-hydroxy-2,3-dihydro-1H-inden-2-yl)methyl]-3-azabicyclo[3.1.0]hexan-6-yl}-4-fluorophenyl)cyclopropanesulfonamide (compound (I)-1) hydrobromide This crystal can be produced in accordance with the above-described method for producing a crystal of a salt of the compound (I).

The solvent to be used for producing a salt and a crystal is not particularly limited as long as the solvent can dissolve or suspend the compound (I)-1, and preferred examples of such a solvent include: alcohols such as methanol, ethanol, 1-propanol, and 2-propanol; water; and mixed solvents of two or more of them. The solvent is more preferably a mixed solvent of an alcohol and water, particularly preferably a mixed solvent of ethanol and water. The mixing ratio (volume ratio) between an alcohol and water is preferably 1:10 to 10:1, more preferably 1:5 to 6:1. The amount of the solvent to be used is preferably 100 mL to 20 L, more preferably 500 mL to 10 L per mole of the compound (I)-1.

Hydrobromic acid to be added is preferably one prepared by dissolving hydrogen bromide gas in water. The amount of hydrobromic acid to be used is preferably 0.7 to 2 moles, more preferably 0.9 to 1.3 moles per mole of the compound (I)-1. When hydrobromic acid is added, the compound (I)-1 may be either dissolved or suspended, but is preferably dissolved. The reaction mixture may be heated to dissolve the compound (I)-1, in which case the heating temperature is preferably room temperature to 100° C., more preferably room temperature to 80° C. The temperature at which hydrobromic acid is added is preferably 0 to 100° C., more preferably 5 to 80° C.

The compound (I)-1 hydrobromide is preferably dissolved once before its crystal is produced. When the compound (I)-1 hydrobromide is dissolved by heating, the temperature of the reaction mixture is preferably room temperature to 100° C., more preferably room temperature to 80° C.

When the crystal is produced, the reaction mixture may be cooled. In this case, the temperature of the reaction mixture is preferably 0 to 60° C., more preferably 5 to 50° C.

When the crystal is produced, a crystal (B) separately prepared as a seed crystal can be added. The amount of the seed crystal to be added is preferably 0.00005 to 0.05 moles, more preferably 0.0001 to 0.02 moles per mole of the compound (I)-1 hydrobromide.

(C) Method for producing crystal of N-(3-{(1R,5S, 6r)-6-ethyl-3-[(2-methoxy-2,3-dihydro-1H-inden-2-yl)methyl]-3-azabicyclo[3.1.0]hexan-6-yl}phenyl) cyclopropanesulfonamide (hereinafter, referred to as a compound (I)-2) hydrochloride This crystal can be produced in accordance with the above-described method for producing a crystal of a salt of the compound (I).

The solvent to be used for producing a salt and a crystal is not particularly limited as long as the solvent can dissolve or suspend the compound (I)-2, and preferred examples of such a solvent include: alcohols such as methanol, ethanol, 1-propanol, and 2-propanol; water; and mixed solvents of two or more of them. The solvent is more preferably a mixed solvent of an alcohol and water, particularly preferably a mixed solvent of ethanol and water. The mixing ratio (volume ratio) between an alcohol and water is preferably 1:10 to 10:1, more preferably 1:5 to 6:1. The amount of the solvent to be used is preferably 100 mL to 20 L, more preferably 500 mL to 10 L per mole of the compound (I)-2.

Hydrochloric acid to be added is preferably one prepared by dissolving hydrogen chloride gas in water. The amount of hydrochloric acid to be used is preferably 0.7 to 2 moles, more preferably 0.9 to 1.3 moles per mole of the compound (I)-2. When hydrochloric acid is added, the compound (I)-2 may be either dissolved or suspended, but is preferably dissolved. The reaction mixture may be heated to dissolve the compound (I)-2, in which case the heating temperature is preferably room temperature to 100° C., more preferably room temperature to 80° C. The temperature at which hydrochloric acid is added is preferably 0 to 100° C., more preferably 5 to 80° C.

The compound (I)-2 hydrochloride is preferably dissolved once before the crystal is produced. When the compound (I)-2 hydrochloride is dissolved by heating, the temperature of the reaction mixture is preferably room temperature to 100° C., more preferably room temperature to 80° C.

When the crystal is produced, the reaction mixture may be cooled. In this case, the temperature of the reaction mixture is preferably 0 to 60° C., more preferably 5 to 50° C.

When the crystal is produced, a crystal (C) separately prepared as a seed crystal can be added. The amount of the seed crystal to be added is preferably 0.00005 to 0.05 moles, more preferably 0.0001 to 0.02 moles per mole of the compound (I)-2 hydrochloride.

(D) Method for producing crystal of N-(3-{(1R,5S, 6r)-6-ethyl-3-[(2-methoxy-2,3-dihydro-1H-inden-2-yl)methyl]-3-azabicyclo[3.1.0]hexan-6-yl}phenyl) cyclopropanesulfonamide (compound (I)-2) hydrobromide This crystal can be produced in accordance with the above-described method for producing a crystal of a salt of the compound (I).

The solvent to be used for producing a salt and a crystal is not particularly limited as long as the solvent can dissolve or suspend the compound (I)-2, and preferred examples of such a solvent include: alcohols such as methanol, ethanol, 1-propanol, and 2-propanol; water; and mixed solvents of two or more of them. The solvent is more preferably a mixed solvent of an alcohol and water, particularly preferably a mixed solvent of ethanol and water. The mixing ratio (volume ratio) between an alcohol and water is preferably 1:10 to 10:1, more preferably 1:5 to 6:1. The amount of the solvent to be used is preferably 100 mL to 20 L, more preferably 500 mL to 10 L per mole of the compound (I)-2.

Hydrobromic acid to be added is preferably one prepared by dissolving hydrogen bromide gas in water. The amount of hydrobromic acid to be used is preferably 0.7 to 10 moles, more preferably 0.9 to 5 moles per mole of the compound (I)-2. When hydrobromic acid is added, the compound (I)-2 may be either dissolved or suspended, but is preferably dissolved. The reaction mixture may be heated to dissolve the compound (I)-2, in which case the heating temperature is preferably room temperature to 100° C., more preferably room temperature to 80° C. The temperature at which hydrobromic acid is added is preferably 0 to 100° C., more preferably 5 to 80° C.

The compound (I)-2 hydrobromide is preferably dissolved once before the crystal is produced. When the compound (I)-2 hydrobromide is dissolved by heating, the temperature of the reaction mixture is preferably room temperature to 100° C., more preferably room temperature to 80° C.

When the crystal is produced, the reaction mixture may be cooled. In this case, the temperature of the reaction mixture is preferably 0 to 60° C., more preferably 5 to 50° C.

When the crystal is produced, a crystal (D) separately prepared as a seed crystal can be added. The amount of the seed crystal to be added is preferably 0.00005 to 0.05 moles, more preferably 0.0001 to 0.02 moles per mole of the compound (I)-2 hydrobromide.

(E) Method for Producing Crystal of N-(3-{(1R,5S, 6r)-3-[3-(4,4-difluoro-1-methoxycyclohexyl)propyl]-6-ethyl-3-azabicyclo[3.1.0]hexan-6-yl}phenyl)cyclopropanesulfonamide (Hereinafter, Referred to as a Compound (I)-3) hydrochloride This crystal can be produced in accordance with the above-described method for producing a crystal of a salt of the compound (I).

The solvent to be used for producing a salt and a crystal is not particularly limited as long as the solvent can dissolve or suspend the compound (I)-3, and preferred examples of such a solvent include: alcohols such as methanol, ethanol, 1-propanol, and 2-propanol; water; and mixed solvents of two or more of them. The solvent is more preferably a mixed solvent of an alcohol and water, particularly preferably a mixed solvent of ethanol and water. The mixing ratio (volume ratio) between an alcohol and water is preferably 1:10 to 10:1, more preferably 1:5 to 6:1. The amount of the solvent to be used is preferably 100 mL to 20 L, more preferably 500 mL to 10 L per mole of the compound (I)-3.

Hydrochloric acid to be added is preferably one prepared by dissolving hydrogen chloride gas in water. The amount of hydrochloric acid to be used is preferably 0.7 to 2 moles, more preferably 0.9 to 1.3 moles per mole of the compound (I)-3. When hydrochloric acid is added, the compound (I)-3 may be either dissolved or suspended, but is preferably dissolved. The reaction mixture may be heated to dissolve the compound (I)-3, in which case the heating temperature is preferably room temperature to 100° C., more preferably room temperature to 80° C. The temperature at which hydrochloric acid is added is preferably 0 to 100° C., more preferably 5 to 80° C.

The compound (I)-3 hydrochloride is preferably dissolved once before the crystal is produced. When the compound (I)-3 hydrochloride is dissolved by heating, the temperature of the reaction mixture is preferably room temperature to 100° C., more preferably room temperature to 80° C.

When the crystal is produced, the reaction mixture may be cooled. In this case, the temperature of the reaction mixture is preferably 0 to 60° C., more preferably 5 to 50° C.

When the crystal is produced, a crystal (E) separately prepared as a seed crystal can be added. The amount of the seed crystal to be added is preferably 0.00005 to 0.05 moles, more preferably 0.0001 to 0.02 moles per mole of the compound (I)-3 hydrochloride.

(F) Method for Producing Crystal of N-(3-{(1R,5S, 6r)-3-[3-(4,4-difluoro-1-methoxycyclohexyl)propyl]-6-ethyl-3-azabicyclo[3.1.0]hexan-6-yl}phenyl) cyclopropanesulfonamide (compound (I)-3) oxalate This crystal can be produced in accordance with the above-described method for producing a crystal of a salt of the compound (I).

The solvent to be used for producing a salt and a crystal is not particularly limited as long as the solvent can dissolve or suspend the compound (I)-3, and preferred examples of such a solvent include: alcohols such as methanol, ethanol, 1-propanol, and 2-propanol; water; and mixed solvents of two or more of them. The solvent is more preferably a mixed solvent of an alcohol and water, particularly preferably a mixed solvent of ethanol and water. The mixing ratio (volume ratio) between an alcohol and water is preferably 1:10 to 10:1, more preferably 1:5 to 6:1. The amount of the solvent to be used is preferably 100 mL to 20 L, more preferably 500 mL to 10 L per mole of the compound (I)-3.

As oxalic acid to be added, solid oxalic acid is preferably used as it is. The amount of oxalic acid to be used is preferably 0.7 to 2 moles, more preferably 0.9 to 1.3 moles per mole of the compound (I)-3. When oxalic acid is added, the compound (I)-3 may be either dissolved or suspended, but is preferably dissolved. The reaction mixture may be heated to dissolve the compound (I)-3, in which case the heating temperature is preferably room temperature to 100° C., more preferably room temperature to 80° C. The temperature at which oxalic acid is added is preferably 0 to 100° C., more preferably 5 to 80° C. It is to be noted that a solution of the compound may be added to a solution of oxalic acid.

The compound (I)-3 oxalate is preferably dissolved once before the crystal is produced. When the compound (I)-3 oxalate is dissolved by heating, the temperature of the reaction mixture is preferably room temperature to 100° C., more preferably room temperature to 80° C.

When the crystal is produced, the reaction mixture may be cooled. In this case, the temperature of the reaction mixture is preferably 0 to 60° C., more preferably 5 to 50° C.

When the crystal is produced, a crystal (F) separately prepared as a seed crystal can be added. The amount of the seed crystal to be added is preferably 0.00005 to 0.05 moles, more preferably 0.0001 to 0.02 moles per mole of the compound (I)-3 oxalate.

(G) Method for Producing Crystal of N-(3-{(1R,5S, 6r)-3-[3-(4,4-difluorocyclohexyl)propyl]-6-ethyl-3-azabicyclo[3.1.0]hexan-6-yl}phenyl)cyclopropanesulfonamide (Hereinafter, Referred to as a Compound (I)-4) hydrobromide This crystal can be produced in accordance with the above-described method for producing a crystal of a salt of the compound (I).

The solvent to be used for producing a salt and a crystal is not particularly limited as long as the solvent can dissolve or suspend the compound (I)-4, and preferred examples of such a solvent include: alcohols such as methanol, ethanol, 1-propanol, and 2-propanol; water; mixed solvents of two or more of them. The solvent is more preferably a mixed solvent of an alcohol and water, particularly preferably a mixed solvent of ethanol and water. The mixing ratio (volume ratio) between an alcohol and water is preferably 1:10 to 10:1, more preferably 1:5 to 6:1. The amount of the solvent to be used is preferably 100 mL to 20 L, more preferably 500 mL to 10 L per mole of the compound (I)-4.

Hydrobromic acid to be added is preferably one prepared by dissolving hydrogen bromide gas in water. The amount of hydrobromic acid to be used is preferably 0.7 to 2 moles, more preferably 0.9 to 1.3 moles per mole of the compound (I)-4. When hydrobromic acid is added, the compound (I)-4 may be either dissolved or suspended, but is preferably dissolved. The reaction mixture may be heated to dissolve the compound (I)-4, in which case the heating temperature is preferably room temperature to 100° C., more preferably room temperature to 80° C. The temperature at which hydrobromic acid is added is preferably 0 to 100° C., more preferably 5 to 80° C.

The compound (I)-4 hydrobromide is preferably dissolved once before the crystal is produced. When the compound (I)-4 hydrobromide is dissolved by heating, the temperature of the reaction mixture is preferably room temperature to 100° C., more preferably room temperature to 80° C.

When the crystal is produced, the reaction mixture may be cooled. In this case, the temperature of the reaction mixture is preferably 0 to 60° C., more preferably 5 to 50° C.

When the crystal is produced, a crystal (G) separately prepared as a seed crystal can be added. The amount of the seed crystal to be added is preferably 0.00005 to 0.05 moles, more preferably 0.0001 to 0.02 moles per mole of the compound (I)-4 hydrobromide.

(H) Method for producing crystal of N-(3-{(1R,5S, 6r)-3-[3-(4,4-difluorocyclohexyl)propyl]-6-ethyl-3-azabicyclo[3.1.0]hexan-6-yl}phenyl)cyclopropanesulfonamide (compound (I)-4) oxalate This crystal can be produced in accordance with the above-described method for producing a crystal of a salt of the compound (I).

The solvent to be used for producing a salt and a crystal is not particularly limited as long as the solvent can dissolve or suspend the compound (I)-4, and preferred examples of such a solvent include: ketones such as acetone, diethyl ketone, and methyl ethyl ketone; water; and mixed solvents of two or more of them. The solvent is more preferably a ketone, particularly preferably acetone. The amount of the solvent to be used is preferably 100 mL to 20 L, more preferably 500 mL to 10 L per mole of the compound (I)-4.

As oxalic acid to be added, solid oxalic acid is preferably used as it is. The amount of oxalic acid to be used is preferably 0.7 to 2 moles, more preferably 0.9 to 1.3 moles per mole of the compound (I)-4. When oxalic acid is added, the compound (I)-4 may be either dissolved or suspended, but is preferably dissolved. The reaction mixture may be heated to dissolve the compound (I)-4, in which case the heating temperature is preferably room temperature to 100° C., more preferably room temperature to 80° C. The temperature at which oxalic acid is added is preferably 0 to 100° C., more preferably 5 to 80° C. It is to be noted that a solution of the compound may be added to a solution of oxalic acid.

The compound (I)-4 oxalate is preferably dissolved once before the crystal is produced. When the compound (I)-4 oxalate is dissolved by heating, the temperature of the reaction mixture is preferably room temperature to 100° C., more preferably room temperature to 80° C.

When the crystal is produced, the reaction mixture may be cooled. In this case, the temperature of the reaction mixture is preferably 0 to 60° C., more preferably 5 to 50° C.

When the crystal is produced, a crystal (H) separately prepared as a seed crystal can be added. The amount of the seed crystal to be added is preferably 0.00005 to 0.05 moles, more preferably 0.0001 to 0.02 moles per mole of the compound (I)-4 oxalate.

Hereinbelow, the use of the crystal according to the present invention as a drug will be described.

Since the compound (I) acts as a µ-opioid receptor antagonist, the crystal according to the present invention can be used as a drug for the prevention or treatment of pruritus. It is to be noted that the compound (I) selectively acts on a µ-opioid receptor, and the gap between the non-protein-bound drug concentration in plasma, which represents anti-pruritic action, and the $IC_{50}$ value of hERG inhibitory activity is wide, and therefore the crystal according to the present invention is also advantageous from the viewpoint of side effects.

Specific examples of diseases accompanied by pruritus to be treated include heat rash, hives, scabies, body ringworm, atopic dermatitis, contact dermatitis, nummular dermatitis, asteatotic dermatitis, bullous pemphigoid, lichen planus, drug-induced hepatic disorder, hand eczema, tinea pedis, pustulosis palmoplantaris, condyloma acuminatum, dermal pruritus, primary biliary cirrhosis, cholestasis, hepatitis, diabetes mellitus, chronic renal failure, renal dialysis, chronic conjunctivitis, allergic conjunctivitis, blepharospasm, external otitis, allergic rhinitis, vulvar candidiasis, senile vulvitis, vaginal trichomonasis, anal pruritus, hyperthyroidism, hypothyroidism, malignancy, mental disorder, xeroderma, psoriasis, itchiness during HIV infection, and itchiness associated with the use of antibody drugs. Similar effects are expected also in mammals other than humans.

Further, the crystal according to the present invention has µ-opioid receptor antagonistic action, and therefore can be expected to be effective as an agent for preventing or treating side effects of µ-opioid receptor agonists, such as constipation, nausea, and vomiting, and idiopathic constipation, postoperative ileus, paralytic ileus, and irritable bowel syndrome. Further, the compound has µ-opioid receptor antagonistic action, and therefore can be expected to be useful for treatment of drug dependency, substance dependency, depression, opiate overdose, schizophrenia, and obesity.

When the crystal according to the present invention is used as a drug, various dosage forms described in General Rules for Preparations of "The Japanese Pharmacopoeia" can be selected depending on its purpose. For example, when the crystal according to the present invention is formed into tablets, orally-ingestible components usually used in this field may be selected. Examples of such components include excipients such as lactose, crystalline cellulose, white sugar, and potassium phosphate. Further, if necessary, various additives usually used in the field of drug formulation, such as binders, disintegrators, lubricants, and anti-aggregation agents may be added.

The amount of the crystal according to the present invention contained as an active ingredient in a preparation is not particularly limited, and is appropriately selected from a wide range. The dose of the crystal according to the present invention is appropriately determined depending on its administration, the age, sex, and other conditions of a patient, and the severity of disease. In the case of oral administration, the daily dose of the crystal according to the present invention is 1 µg to 20 mg, preferably 10 µg to 2 mg per kilogram of body weight, which can be appropriately administered daily in 1 to 4 divided doses. However, since the dose and frequency are determined in consideration of relevant circumstances including the degree of a symptom to be treated, the selection of a compound to be administered, and the selected route of administration, the above-described range of dose and frequency do not limit the scope of the present invention.

EXAMPLES

Hereinafter, the present invention will be described in detail with reference to Reference Examples and Examples, but the present invention is not limited to these Reference Examples and Examples.

Abbreviations described in Examples and Reference Examples are generally used in the same sense as those commonly used in the fields of organic chemistry and pharmacy. More specifically, the following abbreviations are understood by those skilled in the art as follows.
CI: Chemical ionization
EI: Electron ionization
DMSO: dimethylsulfoxide
DAMGO: (2S)-2-({2-[((2R)-2-{[(2S)-2-amino-3-(4-hydroxyphenyl)propanoyl]amino}propanoyeamino]acetyl}-methylamino)-N-(2-hydroxyethyl)-3-phenylpropanamide Powder X-ray crystal diffraction of an obtained crystal was performed under the following conditions. In Examples, pulverization treatment was not performed before the powder X-ray crystal diffraction of a crystal was performed.

It is to be noted that, the horizontal axis and vertical axis of each powder X-ray diffraction pattern shown in the drawing represent diffraction angle (2θ) and peak intensity (cps(count/sec)), respectively. The values of d-spacings described in each powder X-ray diffraction pattern shown in the drawing are calculated using a value of λ=1.54059 Å.
(Measurement Conditions)
Powder X-ray diffractometer: RINT-TTR III (Rigaku Corporation)
Sample holder: Made of glass
Target: Cu-Kα rays (rotating anticathode, 18 kW)
Detector: Scintillation counter
Monochromator: Curved crystal
Tube voltage: 50 kV
Tube current: 300 mA
Scattering slit: 0.5°
Receiving slit: 0.15 mm
Scanning speed: 5°/min
Sampling interval: 0.02°
Scanning range: 1° to 70°
Goniometer: Horizontal sample-type The infrared absorption spectrum of an obtained crystal was measured under the following conditions.

(Measurement Conditions)

Device used: IRPrestaige-21 (Shimadzu Corporation)

Measurement temperature: Room temperature

Measurement method: When a sample was a hydrobromide or an oxalate, measurement was performed in accordance with the KBr method (under a nitrogen atmosphere), and when a sample was a hydrochloride, measurement was performed in accordance with the KCl method (under a nitrogen atmosphere).

Resolution: 4 cm$^{-1}$

Measurement range: 4000 cm$^{-1}$ to 400 cm$^{-1}$

Example 1: N-(3-{(1R,5S,6r)-6-ethyl-3-[(2-hydroxy-2,3-dihydro-1H-inden-2-yl)methyl]-3-azabicyclo[3.1.0]hexan-6-yl}-4-fluorophenyl)cyclopropanesulfonamide hydrochloride

[Chemical Formula 7]

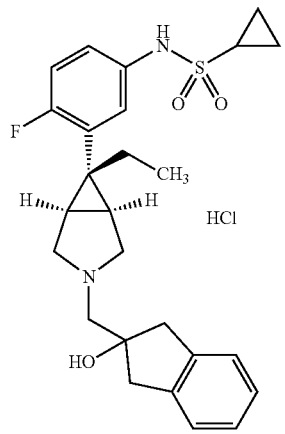

A mixed solution of 0.62 mL (7.0 mmol) of 35 wt % hydrochloric acid and 0.81 ml of water was added to a mixed solution of 3.00 g (6.37 mmol) of N-(3-{(1R,5S,6r)-6-ethyl-3-[(2-hydroxy-2,3-dihydro-1H-inden-2-yl))methyl]-3-azabicyclo[3.1.0]hexan-6-yl}-4-fluorophenyl)cyclopropanesulfonamide, which was obtained in Reference Example 2-(c), in 7.8 mL of ethanol and 2.4 mL of water with stirring at room temperature. The obtained reaction solution was stirred at 60° C. for 1 hour, and then 4.5 mL of ethanol and 2.3 mL of water were added to form a homogeneous solution. The homogeneous solution was stirred at 60° C. for 1 hour. The homogeneous solution was filtered at the unchanged temperature, and then the obtained filtrate was cooled to room temperature with stirring and stirred at the same temperature for 18 hours. Then, the obtained reaction liquid was again heated to 60° C., 31 mL of water was added, and the mixture was stirred at the same temperature for 1 hour, then cooled to 20° C., and stirred at the same temperature for 1 hour. The precipitated solid was collected by filtration, washed with a mixed solvent of ethanol and water (3:1 (V/V)), and then dried at 40° C. under a reduced pressure for 3 hours to obtain 2.71 g of the titled compound as a white solid (crystal). (Yield 84%, calculated as a monohydrochloride)

Mass spectrum (CI, m/z): 471[M$^+$+1]

$^1$H-NMR spectrum (400 MHz, CD$_3$OD) δppm: 7.27-7.14 (m, 6H), 7.08 (dd, J=8.8, 9.9 Hz, 1H), 4.34-3.92 (m, 2H), 3.56 (s, 2H), 3.26-3.12 (m, 2H), 3.21 (d, J=16.2 Hz, 2H), 3.07 (d, J=16.2 Hz, 2H), 2.49 (tt, J=5.0, 7.7 Hz, 1H), 2.40-2.29 (m, 2H), 1.81 (q, J=7.2 Hz, 2H), 1.01-0.93 (m, 4H), 0.91 (t, J=7.2 Hz, 3H)

The powder X-ray diffraction pattern and infrared absorption spectrum of the crystal obtained in Example 1 are shown in FIGS. 1 and 2, respectively.

Example 2: N-(3-{(1R,5S,6r)-6-ethyl-3-[(2-hydroxy-2,3-dihydro-1H-inden-2-yl)methyl]-3-azabicyclo[3.1.0]hexan-6-yl}-4-fluorophenyl)cyclopropanesulfonamide hydrobromide

[Chemical Formula 8]

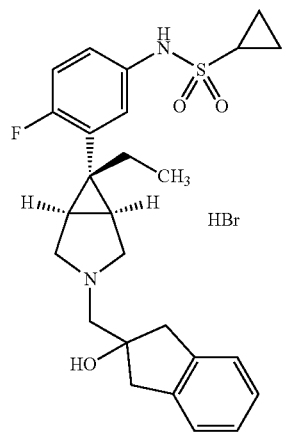

0.87 mL (7.7 mmol) of a 48 wt % aqueous hydrobromic acid solution was added to a mixed solution of 3.00 g (6.37 mmol) of N-(3-{(1R,5S,6r)-6-ethyl-3-[(2-hydroxy-2,3-dihydro-1H-inden-2-yl))methyl]-3-azabicyclo[3.1.0]hexan-6-yl}-4-fluorophenyl)cyclopropanesulfonamide, which was obtained in Reference Example 2-(c), in 12 mL of ethanol and 6.0 mL of water with stirring at room temperature. The obtained reaction solution was heated to 50° C. with stirring, then cooled to room temperature, and further stirred at the same temperature for 1 hour. Then, the reaction solution was again heated to 50° C., 6 mL of water was added, and the mixture was stirred at the same temperature for 1 hour. The obtained reaction solution was cooled to room temperature and stirred at the same temperature for 15 hours. The precipitated solid was collected by filtration and dried at 40° C. under a reduced pressure for 3 hours to obtain 3.34 g of the titled compound as a white solid (crystal). (Yield 95%, calculated as a monohydrobromide)

Mass spectrum (CI, m/z): 471[M$^+$+1]

$^1$H-NMR spectrum (400 MHz, CD$_3$OD) δppm: 7.29-7.14 (m, 6H), 7.08 (dd, J=8.8, 9.9 Hz, 1H), 4.35-4.04 (m, 2H), 3.63-3.49 (m, 2H), 3.26-3.11 (m, 2H), 3.21 (d, J=16.3 Hz, 2H), 3.07 (d, J=16.3 Hz, 2H), 2.49 (tt, J=5.5, 7.7 Hz, 1H), 2.41-2.27 (m, 2H), 1.81 (q, J=7.2 Hz, 2H), 1.02-0.92 (m, 4H), 0.91 (t, J=7.3 Hz, 3H)

The powder X-ray diffraction pattern and infrared absorption spectrum of the crystal obtained in Example 2 are shown in FIGS. 3 and 4, respectively. Example 3: N-(3-{(1R,5S,6r)-6-ethyl-3-[(2-methoxy-2,3-dihydro-1H-inden-2-yl)methyl]-3-azabicyclo[3.1.0]hexan-6-yl}phenyl)cyclopropanesulfonamide hydrochloride

[Chemical Formula 9]

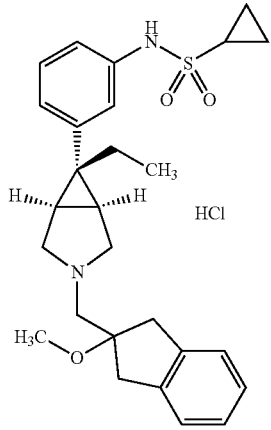

6.0 mL of water was added to a solution of 3.00 g (6.43 mmol) of N-(3-{(1R,5S,6r)-6-ethyl-3-[(2-methoxy-2,3-dihydro-1H-inden-2-yl)methyl]-3-azabicyclo[3.1.0]hexan-6-yl}phenyl)cyclopropanesulfonamide, which was obtained in Reference Example 4-(c), in 16 mL of ethanol with stirring at room temperature, and 0.98 mL (5.9 mmol) of 6 N hydrochloric acid was further added. The obtained reaction solution was stirred at 45° C. for 10 minutes, then cooled to room temperature, and further stirred at the same temperature for 1 hour. Then, the reaction solution was again heated to 50° C. and stirred at the same temperature for 30 minutes, then cooled to room temperature, and further stirred at the same temperature for 1 hour. The precipitated solid was collected by filtration, washed with a mixed solvent of ethanol and water (1:1 (V/V)) cooled with ice, and then dried at 50° C. under a reduced pressure for 3 hours to obtain 2.72 g of the titled compound as a white solid (crystal). (Yield 92%, calculated as a monohydrochloride)

Mass spectrum (CI, m/z): 467[M$^+$+1]

$^1$H-NMR spectrum (400 MHz, CD$_3$OD) δppm: 7.29 (dd, J=7.8, 7.9 Hz, 1H), 7.27-7.17 (m, 5H), 7.13 (ddd, J=1.1, 2.2, 8.0 Hz, 1H), 7.11-7.08 (m, 1H), 4.51-3.78 (m, 2H), 3.75-3.48 (m, 2H), 3.33-3.02 (m, 6H), 3.13 (s, 3H), 2.52 (tt, J=4.9, 7.9 Hz, 1H), 2.41-2.28 (m, 2H), 1.83 (q, J=7.3 Hz, 2H), 1.06-0.90 (m, 4H), 0.88 (t, J=7.3 Hz, 3H)

The powder X-ray diffraction pattern and infrared absorption spectrum of the crystal obtained in Example 3 are shown in FIGS. 5 and 6, respectively.

Example 4: N-(3-{(1R,5S,6r)-6-ethyl-3-[(2-methoxy-2,3-dihydro-1H-inden-2-yl)methyl]-3-azabicyclo[3.1.0]hexan-6-yl}phenyl)cyclopropanesulfonamide hydrobromide

[Chemical Formula 10]

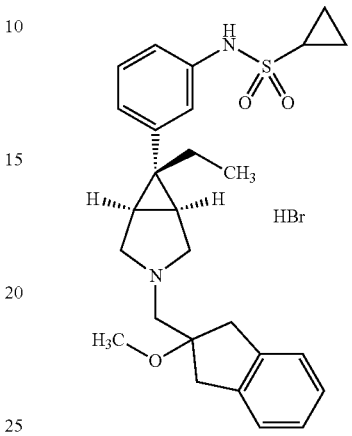

4.5 ml of water was added to a solution of 3.00 g (6.43 mmol) of N-(3-{(1R,5S,6r)-6-ethyl-3-[(2-methoxy-2,3-dihydro-1H-inden-2-yl)methyl]-3-azabicyclo[3.1.0]hexan-6-yl}phenyl)cyclopropanesulfonamide, which was obtained in Reference Example 4-(c), in 16 mL of ethanol with stirring at room temperature, and 2.71 g (16.1 mmol) of a 48 wt % aqueous hydrobromic acid solution was further added. The obtained reaction solution was stirred at room temperature for 15 hours, then heated to 50° C., stirred at the same temperature for 30 minutes, then cooled to room temperature, and further stirred at the same temperature for 1 hour. The precipitated solid was collected by filtration, washed with a mixed solvent of ethanol and water (1:1 (V/V)) cooled with ice, and then dried at 50° C. under a reduced pressure for 3 hours to obtain 3.25 g of the titled compound as a white solid (crystal). (Yield 92%, calculated as a monohydrobromide)

Mass spectrum (CI, m/z): 467[M$^+$+1]

$^1$H-NMR spectrum (400 MHz, DMSO-d$_6$) δppm: 10.12 (br. s, 0.9H), 9.73 (br. s, 1H), 9.55 (br. s, 0.1H), 7.34-7.14 (m, 6H), 7.12-7.06 (m, 1H), 7.05-6.99 (m, 1H), 4.21-3.84 (m, 2H), 3.77-3.64 (m, 2H), 3.19 (d, J=16.8 Hz, 2H), 3.14-2.94 (m, 4H), 3.08 (s, 3H), 2.60 (tt, J=5.1, 7.8 Hz, 1H), 2.17 (m, 2H), 1.76 (q, J=7.2 Hz, 2H), 0.98-0.86 (m, 4H), 0.77 (t, J=7.2 Hz, 3H)

The powder X-ray diffraction pattern and infrared absorption spectrum of the crystal obtained in Example 4 are shown in FIGS. 7 and 8, respectively. Example 5: N-(3-{(1R,5S,6r)-3-[3-(4,4-difluoro-1-methoxycyclohexyl)propyl]-6-ethyl-3-azabicyclo[3.1.0]hexan-6-yl}phenyl)cyclopropanesulfonamide hydrochloride

[Chemical Formula 11]

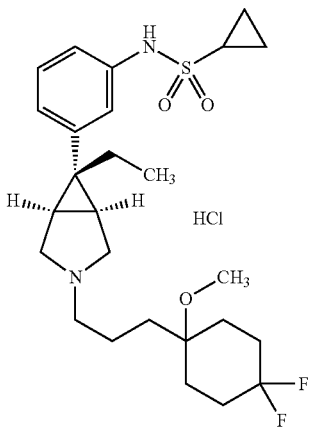

Example 5-(a)

A mixed solution of 40 μL (0.24 mmol) of 6 N hydrochloric acid and 60 μL of water was added to a solution of 100 mg (0.201 mmol) of N-(3-{(1R,5S,6r)-3-[3-(4,4-difluoro-1-methoxycyclohexyl)propyl]-6-ethyl-3-azabicyclo[3.1.0]hexan-6-yl}phenyl)cyclopropanesulfonamide, which was obtained in the same manner as in Reference Example 5-(e), in 50 μL of ethanol at room temperature, and the mixture was stirred at 50° C. for 30 minutes, then cooled to room temperature, and further stirred at the same temperature for 18 hours. Then, the reaction solution was again heated to 50° C., 50 μL of water was added, and the mixture was stirred at the same temperature for 1 hour, then cooled to room temperature, and further stirred at the same temperature for 1 hour. The precipitated solid was collected by filtration and dried under a reduced pressure to obtain 60 mg of the titled compound as a white solid.

Example 5-(b)

1.2 mL (7.2 mmol) of 6 N hydrochloric acid was added to a mixed solution of 3.00 g (6.04 mmol) of N-(3-{(1R,5S,6r)-3-[3-(4,4-difluoro-1-methoxycyclohexyl)propyl]-6-ethyl-3(azabicyclo[3.1.0]hexan-6-yl}phenyl)cyclopropanesulfonamide, which was obtained in Reference Example 5-(e), in 1.5 mL of ethanol and 1.8 mL of water with stirring at room temperature. The obtained reaction solution was stirred at 50° C. and then cooled to room temperature. The solid obtained in Example 5-(a) was added as a seed crystal to the reaction solution, and the mixture was stirred at room temperature for 15 hours. Then, the reaction solution was again heated to 50° C. and stirred at the same temperature for 1 hour, 1.5 mL of water was further added, and then the mixture was cooled to room temperature and stirred at the same temperature for 1 hour. The precipitated solid was collected by filtration and dried at 40° C. under a reduced pressure for 3 hours to obtain 2.60 g of the titled compound as a white solid (crystal). (Yield 81%, calculated as a monohydrochloride)

Mass spectrum (CI, m/z): 497[M$^+$+1]

$^1$H-NMR spectrum (400 MHz, CD$_3$OD) δppm: 7.28 (dd, J=7.7, 7.9 Hz, 1H), 7.24 (dd, J=1.7, 2.0 Hz, 1H), 7.12 (ddd, J=1.1, 2.0, 7.9 Hz, 1H), 7.08 (ddd, J=1.1, 1.7, 7.7 Hz, 1H), 4.20-3.75 (m, 2H), 3.25-3.01 (m, 4H), 3.18 (s, 3H), 2.51 (tt, J=4.9, 7.8 Hz, 1H), 2.39-2.27 (m, 2H), 2.06-1.63 (m, 10H), 1.59-1.44 (m, 4H), 1.04-0.90 (m, 4H), 0.87 (t, J=7.3 Hz, 3H)

The powder X-ray diffraction pattern and infrared absorption spectrum of the crystal obtained in Example 5 are shown in FIGS. 9 and 10, respectively.

Example 6: N-(3-{(1R,5S,6r)-3-[3-(4,4-difluoro-1-methoxycyclohexyl)propyl]-6-ethyl-3-azabicyclo[3.1.0]hexan-6-yl}phenyl)cyclopropanesulfonamide oxalate

[Chemical Formula 12]

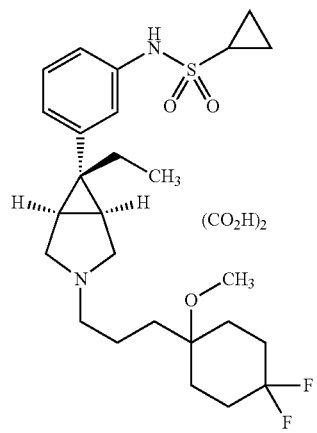

0.650 g (7.22 mmol) of oxalic acid was added to a mixed solution of 3.00 g (6.04 mmol) of N-(3-{(1R,5S,6r)-3-[3-4,4-difluoro-1-methoxycyclohexyl)propyl]-6-ethyl-3-azabicyclo[3.1.0]hexan-6-yl}phenyl)cyclopropanesulfonamide, which was obtained in Reference Example 5-(e), in 4.5 mL of ethanol and 4.5 mL of water with stirring at room temperature, and the mixture was stirred at 50° C. for 1 hour. The obtained reaction solution was cooled to room temperature and stirred at the same temperature for 12 hours. Then, the reaction solution was again heated to 50° C., 4.5 mL of water was added, and the mixture was stirred at the same temperature for 1 hour, then cooled to room temperature, and stirred at the same temperature for 3 hours. The precipitated solid was collected by filtration and dried at 40° C. under a reduced pressure for 3 hours to obtain 2.95 g of the titled compound as a white solid (crystal). (Yield 83%, calculated as a monooxalate)

Mass spectrum (CI, m/z): 497[M$^+$+1]

$^1$H-NMR spectrum (400 MHz, CD$_3$OD) δppm: 7.28 (dd, J=7.8, 7.9 Hz, 1H), 7.23 (dd, J=1.7, 2.0 Hz, 1H), 7.12 (ddd, J=1.0, 2.0, 7.9 Hz, 1H), 7.08 (ddd, J=1.0, 1.7, 7.8 Hz, 1H), 4.30-3.76 (m, 2H), 3.26-2.99 (m, 4H), 3.17 (s, 3H), 2.51 (tt, J=4.9, 7.9 Hz, 1H), 2.40-2.26 (m, 2H), 2.08-1.62 (m, 10H), 1.60-1.44 (m, 4H), 1.04-0.89 (m, 4H), 0.87 (t, J=7.3 Hz, 3H)

The powder X-ray diffraction pattern and infrared absorption spectrum of the crystal obtained in Example 6 are shown in FIGS. 11 and 12, respectively.

Example 7: N-(3-{(1R,5S,6r)-3-[3-(4,4-difluorocyclohexyl)propyl]-6-ethyl-3-azabicyclo[3.1.0]hexan-6-yl}phenyl)cyclopropanesulfonamide hydrobromide

[Chemical Formula 13]

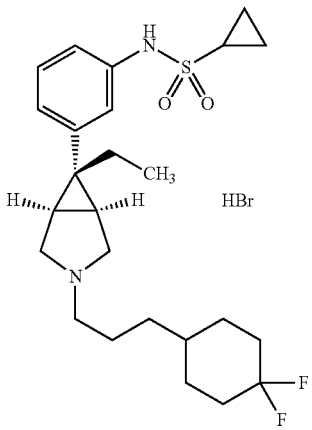

0.87 mL (7.7 mmol) of a 48 wt % aqueous hydrobromic acid solution was added to a mixed solution of 3.00 g (6.43 mmol) of N-(3-{(1R,5S,6r)-3-[3-(4,4-difluorocyclohexyl)propyl]-6-ethyl-3-azabicyclo[3.1.0]hexan-6-yl}phenyl)cyclopropanesulfonamide, which was obtained in Reference Example 6-(d), in 3.0 mL of ethanol and 3.0 mL of water with stirring at room temperature, and the mixture was stirred at room temperature for 12 hours. The obtained reaction solution was heated to 50° C., 6 mL of water was added, and the mixture was stirred at the same temperature for 1 hour, then cooled to room temperature, and stirred at the same temperature for 1 hour. The precipitated solid was collected by filtration, washed with water, and then dried at 40° C. under a reduced pressure for 3 hours to obtain 2.97 g of the titled compound as a white solid (crystal). (Yield 84%, calculated as a monohydrobromide)

Mass spectrum (CI, m/z): 467[M$^+$+1]

$^1$H-NMR spectrum (400 MHz, CD$_3$OD) δppm: 7.28 (dd, J=7.4, 8.0 Hz, 1H), 7.24 (dd, J=1.8, 2.0 Hz, 1H), 7.12 (ddd, J=0.9, 2.0, 7.9 Hz, 1H), 7.10-7.06 (m, 1H), 4.24-3.72 (m, 2H), 3.26-2.89 (m, 4H), 2.51 (tt, J=4.9, 7.9 Hz, 1H), 2.38-2.26 (m, 2H), 2.10-1.96 (m, 2H), 1.91-1.62 (m, 8H), 1.52-1.14 (m, 5H), 1.05-0.90 (m, 4H), 0.87 (t, J=7.3 Hz, 3H)

The powder X-ray diffraction pattern and infrared absorption spectrum of the crystal obtained in Example 7 are shown in FIGS. 13 and 14, respectively.

Example 8: N-(3-{(1R,5S,6r)-3-[3-(4,4-difluorocyclohexyl)propyl]-6-ethyl-3-azabicyclo[3.1.0]hexan-6-yl}phenyl)cyclopropanesulfonamide oxalate

[Chemical Formula 14]

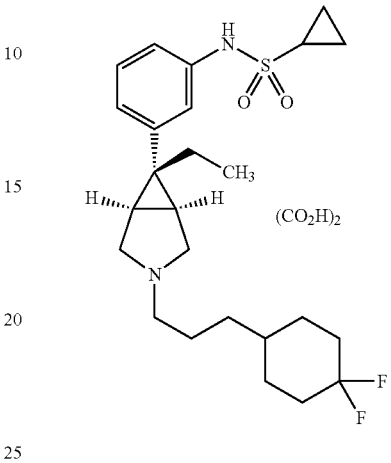

695 mg (7.72 mmol) of oxalic acid was added to a solution of 3.00 g (6.43 mmol) of N-(3-{(1R,5S,6r)-3-[3-(4,4-difluorocyclohexyl)propyl]-6-ethyl-3-azabicyclo[3.1.0]hexan-6-yl}phenyl)cyclopropanesulfonamide, which was obtained in Reference Example 6-(d), in 6.0 mL of acetone with stirring at room temperature. The obtained reaction solution was stirred at 50° C., then cooled to room temperature, and stirred at the same temperature for 1 hour. The reaction solution was again heated to 50° C. and stirred at the same temperature for 1 hour, 1.5 ml of acetone was added, and then the mixture was cooled to room temperature and stirred at the same temperature for 1 hour. The precipitated solid was collected by filtration and dried at 40° C. under a reduced pressure for 3 hours to obtain 2.51 g of the titled compound as a white solid (crystal). (Yield 70%, calculated as a monooxalate)

Mass spectrum (CI, m/z): 467[M$^+$+1]

$^1$H-NMR spectrum (400 MHz, CD$_3$OD) δppm: 7.28 (dd, J=7.8, 7.9 Hz, 1H), 7.23 (dd, J=1.8, 2.0 Hz, 1H), 7.12 (ddd, J=1.0, 2.1, 7.9 Hz, 1H), 7.10-7.04 (m, 1H), 4.22-3.72 (m, 2H), 3.26-2.75 (m, 4H), 2.51 (tt, J=4.9, 7.9 Hz, 1H), 2.39-2.26 (m, 2H), 2.09-1.94 (m, 2H), 1.89-1.61 (m, 8H), 1.52-1.16 (m, 5H), 1.07-0.89 (m, 4H), 0.87 (t, J=7.3 Hz, 3H)

The powder X-ray diffraction pattern and infrared absorption spectrum of the crystal obtained in Example 8 are shown in FIGS. 15 and 16, respectively.

Reference Example 1-(a): (1R,5S,6r)-6-(5-bromo-2-fluorophenyl)-6-ethyl-3-azabicyclo[3.1.0]hexane-2,4-dione 50 mL (1030 mmol) of hydrazine monohydrate was added dropwise to a solution of 57.0 g (247 mmol) of 1-(5-bromo-2-fluorophenyl)propan-1-one (see WO 2009/144554) in 500 mL of methanol at 24 to 28° C., and the mixture was stirred at 60° C. for 2.5 hours. After the completion of reaction, the reaction mixture was cooled to room temperature, and poured into a mixed solvent of 1000 mL of methylene chloride and 500 mL of water to obtain an organic layer by liquid separation. The organic layer was washed with 500 mL of water twice and dried with anhydrous sodium sulfate, 500 g of 1,4-dioxane was then added, and part of the solvent was distilled away by vacuum concentration to obtain about 480 g of a solution. Then, 65 g of manganese dioxide was added to the obtained solution under a nitrogen stream with ice cooling, and the mixture was stirred at 0 to 10° C. for 3 hours. Further, 35 g of manganese dioxide was added, and the mixture was stirred at 0 to 10° C. for 3 hours, and this operation was repeated twice. The reaction solution was filtered through Celite, and the Celite was washed with 300 mL of 1,4-dioxane. Then, the obtained filtrate was added dropwise to a solution of 24.0 g (247 mmol) of maleimide in 100 mL of 1,4-dioxane at 14° C. under a nitrogen stream, and the mixture was stirred at room temperature for 15 hours. The obtained reaction solution was added dropwise to 200 mL of 1,4-dioxane heated to 95 to 105° C. over 2 hours, and the mixture was stirred at the same temperature for 2 hours. After the completion of reaction, the reaction solution was cooled to room temperature and concentrated to about 83 g under a reduced pressure. Then, 180 ml of ethanol was added, and the mixture was concentrated to 73 g under a reduced pressure. Then, 30 mL of heptane and 30 mL of ethanol were added, and the mixture was stirred at 50° C. and then stirred with ice cooling. The precipitated solid was collected by filtration, washed with 60 mL of a mixed solvent of heptane and ethanol (1:1 (V/V)), and dried under reduced pressure to obtain 26.8 g of the titled compound as a white solid. (Yield 35%)

The steric configuration was determined by measuring the $^1$H-NMR difference NOE spectrum of Reference Example 1-(a).

Mass spectrum (CI, m/z): 312, 314[M$^+$+1]

$^1$H-NMR spectrum (400 MHz, DMSO-d$_6$) δ ppm: 11.00 (br. s, 1H), 7.61-7.55 (m, 2H), 7.31-7.20 (m, 1H), 2.92 (s, 2H), 1.74 (q, J=7.4 Hz, 2H), 0.80 (t, J=7.4 Hz, 3H)

Reference Example 1-(b): (1R,5S,6r)-tert-butyl 6-(5-bromo-2-fluorophenyl)-6-ethyl-3-azabicyclo[3.1.0]hexane-3-carboxylate 600 mL (540 mmol) of a 0.9 M borane-tetrahydrofuran complex/tetrahydrofuran solution was added dropwise to a solution of 28.0 g (90.0 mmol) of (1R,5S,6r)-6-(5-bromo-2-fluorophenyl)-6-ethyl-3-azabicyclo[3.1.0]hexane-2,4-dione, which was obtained in the same manner as in Reference Example 1-(a), in 100 mL of tetrahydrofuran under an argon stream at room temperature, and the mixture was stirred at 60° C. for 8.5 hours. The reaction solution was cooled with ice, 90 mL of methanol was added dropwise, and the mixture was stirred for 15 hours. Then, 150 mL of 6 N hydrochloric acid was added, and the mixture was stirred at 65° C. for 1.5 hours. The obtained reaction solution was cooled to room temperature, 300 mL of a 5 N aqueous sodium hydroxide solution and 20.0 g (91.6 mmol) of di-tert-butyl dicarbonate were added, and the mixture was stirred at room temperature for 2 hours. Then, 200 mL of tert-butyl methyl ether was added to the reaction solution to obtain an organic layer by liquid separation. Then, the obtained organic layer was washed with 300 mL of 1 N hydrochloric acid, then with 300 mL of a saturated aqueous sodium hydrogen carbonate solution, and then with a saturated aqueous sodium chloride solution, dried with anhydrous magnesium sulfate, and concentrated under a reduced pressure. The obtained residue was subjected to silica gel column chromatography (elution solvent: hexane:ethyl acetate=67:33 (V/V)), and a fraction containing a desired product was concentrated under a reduced pressure to obtain 24.2 g of the titled compound as a colorless oil. (Yield 70%)

$^1$H-NMR spectrum (400 MHz, CDCl$_3$) δppm: 7.35 (dd, J=2.5, 6.4 Hz, 1H), 7.31 (ddd, J=2.5, 4.5, 8.7 Hz, 1H), 6.89 (dd, J=8.7, 9.8 Hz, 1H), 3.65 (dd, J=5.3, 11.3 Hz, 1H), 3.60 (dd, J=5.3, 11.5 Hz, 1H), 3.56 (d, J=11.3 Hz, 1H), 3.50 (d, J=11.5 Hz, 1H), 1.90 (dd, J=5.3, 8.1 Hz, 1H), 1.86 (dd, J=5.3, 8.1 Hz, 1H), 1.61-1.42 (m, 2H), 1.47 (s, 9H), 0.88-0.80 (m, 3H)

Reference Example 1-(c): (1R,5S,6r)-tert-butyl 6-[5 (cyclopropanesulfonamido)-2-fluorophenyl]-6-ethyl-3-azabicyclo[3.1.0]hexane-3-carboxylate 9.90 g (81.7 mmol) of cyclopropanesulfonamide and 12.2 g (88.3 mmol) of potassium carbonate were added to a solution of 24.2 g (63.0 mmol) of (1R,5S,6r)-tert-butyl 6-(5-bromo-2-fluorophenyl)-6-ethyl-3-azabicyclo[3.1.0] hexane-3-carboxylate, which was obtained in Reference Example 1-(b), in 100 mL of toluene. Air in a reaction vessel was replaced with nitrogen, and then 476 mg (1.30 mmol) of bis (η3-allyl-µ-chloropalladium) and 1.66 g (3.91 mmol) of tert-butyl XPhos were added, and the mixture was stirred at 110° C. for 2 hours. Then, 300 mL of tetrahydrofuran, 12.4 g of ammonium chloride, and 100 mL of water were added to the reaction solution to obtain an organic layer by liquid separation. The obtained organic layer was washed with a saturated aqueous sodium chloride solution, dried with anhydrous magnesium sulfate, and concentrated under a reduced pressure. Then, 50 mL of heptane and 50 mL of toluene were added to the obtained residue, and the mixture was heated to 55° C. This solution was cooled with ice and further stirred. The precipitated solid was collected by filtration, washed with 30 mL of a mixed solvent of heptane and toluene (1:1 (V/V)) and dried to obtain 21.5 g of the titled compound as a white solid. (Yield 80%)

Reference Example 1-(d): N-{3-[(1R,5S,6r)-6-ethyl-3-azabicyclo[3.1.0]hexan-6-yl]-4-fluorophenyl}cyclopropanesulfonamide hydrochloride 150 mL (600 mmol) of a 4 N hydrogen chloride/1,4-dioxane solution was added to a solution of 21.5 g (50.6 mmol) of (1R,5S,6r)-tert-butyl 6-[5-(cyclopropanesulfonamido)-2-fluorophenyl]-6-ethyl-3-azabicyclo[3.1.0]hexane-3-carboxylate, which was obtained in Reference Example 1-(c), in 28.0 mL of 1,4-dioxane with stirring at room temperature under an argon stream, and the mixture was stirred at 24 to 28° C. for 5 hours. The reaction solution was filtered, and the obtained solid was dried under a reduced pressure for 1 hour. Then, 50 mL of ethyl acetate was added, and the mixture was stirred for 18 hours. The precipitated solid was filtered and dried under a reduced pressure for 3 hours to obtain 16.4 g of the titled compound as a white solid. (Yield: 90%, calculated as a monohydrochloride)

Mass spectrum (CI, m/z): 325[M$^+$+1]

$^1$H-NMR spectrum (400 MHz, DMSO-d$_6$) δppm: 9.93-8.77 (m, 2.8H), 7.19-7.09 (m, 3H), 3.69-3.60 (m, 2H), 3.21 (d, J=12.9 Hz, 2H), 2.59-2.49 (m, 1H), 2.20-2.13 (m, 2H), 1.53 (q, J=7.3 Hz, 2H), 0.94-0.81 (m, 4H), 0.78 (t, J=7.3 Hz, 3H)

Reference Example 2-(a): 2-(hydroxymethyl)-2,3-dihydro-1H-inden-2-ol 7.13 g (40.0 mmol) of 2-hydroxy-2,3-dihydro-1H-indene-2-carboxylic acid (see Journal of Organic Chemistry, 56 (1991) 4129-4134) was added to a mixed liquid of 40 mL (80 mmol) of a 2.0 M lithium aluminum hydride/tetrahydrofuran solution and 60 mL of tetrahydrofuran with ice cooling, and the mixture was stirred at room temperature for 1 hour. After the completion of reaction, 3.0 mL of water and 120 mL of 2 N hydrochloric acid were added to the reaction solution, and the mixture was subjected to extraction with 100 mL of ethyl acetate. The obtained organic layer was washed with 50 mL of 1 N hydrochloric acid and then with a saturated aqueous sodium chloride solution, dried with anhydrous magnesium sulfate, and concentrated under a reduced pressure. Diisopropyl ether and ethyl acetate were added to the obtained residue, and the mixture was stirred at room temperature for 15 hours. The precipitated solid was collected by filtration to obtain 5.23 g of the titled compound as a white solid. (Yield 80%)

Mass spectrum (EI, m/z): 164[M+]

$^1$H-NMR spectrum (400 MHz, CDCl$_3$) δppm: 7.24-7.14 (m, 4H), 3.70 (s, 2H), 3.11 (d, J=16.4 Hz, 2H), 2.99 (d, J=16.4 Hz, 2H), 2.70-1.50 (m, 2H)

Reference Example 2-(b): (2-hydroxy-2,3-dihydro-1H-inden-2-yl)methyl methanesulfonate 7.6 mL (55 mmol) of triethylamine was added to a solution of 6.00 g (36.5 mmol) of 2-(hydroxymethyl)-2,3-dihydro-1H-inden-2-ol, which was obtained in the same manner as in Reference Example 2-(a), in 60.0 mL of methylene chloride with stirring under an argon stream, and then 3.0 mL (39 mmol) of methanesulfonyl chloride was added dropwise at 0 to 15° C., and the mixture was stirred at 0° C. for 30 minutes. The reaction solution was added to a mixed solvent of 140 mL of water and 420 mL of ethyl acetate to obtain an organic layer by liquid separation. The organic layer was washed with 140 mL of a saturated aqueous sodium chloride solution, dried with anhydrous magnesium sulfate, and concentrated under a reduced pressure. The obtained residue was subjected to silica gel column chromatography (elution solvent: hexane:ethyl acetate=70:30→40:60 (V/V)), and a fraction containing a desired product was concentrated under a reduced pressure to obtain 7.8 g of a yellow oily product. Then, 30 mL of diisopropyl ether was added to the obtained yellow oily product, and the mixture was stirred for 18 hours, then filtered, and dried under a reduced pressure for 3 hours to obtain 6.86 g of the titled compound as a white solid. (Yield: 77%)

Mass spectrum (CI, m/z): 243[M$^+$+1]

$^1$H-NMR spectrum (400 MHz, CDCl$_3$) δppm: 7.24-7.17 (m, 4H), 4.34 (s, 2H), 3.17 (d, J=16.6 Hz, 2H), 3.11 (s, 3H), 3.07 (d, J=16.6 Hz, 2H)

Reference Example 2-(c): N-(3-{(1R,5S,6r)-6-ethyl-3-[(2-hydroxy-2,3-dihydro-1H-inden-2-yl)methyl]-3-azabicyclo[3.1.0]hexan-6-yl}-4-fluorophenyl)cyclopropanesulfonamide 8.44 g (23.4 mmol) of N-{3-[(1R,5S,6r)-6-ethyl-3-azabicyclo[3.1.0]hexan-6-yl]-4-fluorophenyl} cyclopropanesulfonamide hydrochloride, which was obtained in Reference Example 1-(d), and 7.8 mL (56 mmol) of triethylamine were added to a solution of 6.80 g (28.1 mmol) of (2-hydroxy-2,3-dihydro-1H-inden-2-yl)methyl methanesulfonate, which was obtained in Reference Example 2-(b), in 170 mL of ethanol with stirring under an argon stream, and the mixture was stirred at 100° C. for 14 hours. The reaction solution was concentrated under a reduced pressure, 150 mL of a saturated aqueous sodium hydrogen carbonate solution was added to the obtained residue, and the mixture was subjected to extraction with 150 mL of ethyl acetate. The obtained organic layer was washed with 150 mL of a saturated aqueous sodium chloride solution, dried with anhydrous magnesium sulfate, and concentrated under a reduced pressure. Then, 10 mL of methanol and 20 mL of ethyl acetate were added to the obtained residue, and the mixture was stirred for 1 hour. The precipitated solid was filtered and dried at 50° C. under a reduced pressure for 3 hours to obtain 7.95 g of the titled compound as a colorless oil. (Yield 72%)

Mass spectrum (CI, m/z): 471[M$^+$+1]

$^1$H-NMR spectrum (400 MHz, CDCl$_3$) δppm: 7.24-7.12 (m, 5H), 7.08 (ddd, J=2.8, 4.3, 8.9 Hz, 1H), 6.98 (dd, J=8.9, 9.1 Hz, 1H), 6.17 (br. s, 1H), 3.44 (br. s, 1H), 3.27 (d, J=9.7 Hz, 2H), 3.14-3.05 (m, 2H), 3.00 (d, J=16.8 Hz, 2H), 3.00 (d, J=16.8 Hz, 2H), 2.83 (s, 2H), 2.42 (tt, J=4.8, 8.0 Hz, 1H), 1.88 (q, J=7.3 Hz, 2H), 1.87-1.81 (m, 2H), 1.20-1.09 (m, 2H), 1.00-0.91 (m, 2H), 0.85 (t, J=7.3 Hz, 3H)

Reference Example 2-(d): N-(3-{(1R,5S,6r)-6-ethyl-3-[(2-hydroxy-2,3-dihydro-1H-inden-2-yl)methyl]-3-azabicyclo[3.1.0]hexan-6-yl}-4-fluorophenyl)cyclopropanesulfonamide hydrochloride 1.37 mL (5.48 mmol) of a 4 N hydrogen chloride/ethyl acetate solution was added to a solution of 1.29 g (2.74 mmol) of N-(3-{(1R,5S,6r)-6-ethyl-3-[(2-hydroxy-2,3-dihydro-1H-inden-2-yl)methyl]-3-azabicyclo[3.1.0]hexan-6-yl}-4-fluorophenyl)cyclopropanesulfonamide, which was obtained in the same manner as in Reference Example 2-(c), in 20 mL of ethyl acetate, and the mixture was stirred at room temperature for 10 minutes. After the completion of reaction, the reaction solution was concentrated under a reduced pressure. Then, 10 mL of acetone was added to the residue, and the mixture was stirred at 50° C. and then stirred at room temperature for 1 hour. The precipitated solid was collected by filtration. The obtained solid was dried at 50° C. under a reduced pressure to obtain 1.32 g of the titled compound as a white solid. (Yield 95%, calculated as a monohydrochloride)

Mass spectrum (CI, m/z): 471[M$^+$+1]

$^1$H-NMR spectrum (400 MHz, CD$_3$OD) δppm: 7.27-7.15 (m, 6H), 7.07 (dd, J=9.9, 8.8 Hz, 1H), 4.70-3.95 (m, 2H), 3.56 (s, 2H), 3.26-3.01 (m, 2H), 3.21 (d, J=16.2 Hz, 2H), 3.07 (d, J=16.2 Hz, 2H), 2.49 (tt, J=7.7, 5.0 Hz, 1H), 2.42-2.28 (m, 2H), 1.81 (q, J=7.3 Hz, 2H), 1.02-0.87 (m, 4H), 0.91 (t, J=7.3 Hz, 3H)

Reference Example 3-(a): (1R,5S,6r)-6-(3-bromophenyl)-6-ethyl-3-azabicyclo[3.1.0]hexan-2,4-dione Under a nitrogen stream, 800 mL of methanol was added to 80.0 g (0.375 mol) of 3-bromopropiophenone, and then 75.1 g (1.50 mol) of hydrazine monohydrate was added dropwise at 18 to 22° C. over 5 minutes. The reaction solution was stirred at 60° C. for 3 hours, then cooled to room temperature, and added to a mixed solution of 1600 mL of methylene chloride and 800 mL of water to obtain an organic layer by liquid separation. The organic layer was washed with 800 mL of water twice and dried with anhydrous sodium sulfate. Then, 800 mL of 1,4-dioxane was added to the organic layer, and the mixture was partially concentrated at 40° C. under a reduced pressure to obtain 704 g of a yellow solution. Manganese dioxide was added separately in three parts (112.0 g, 112.0 g, 80.0 g) to 704 g of the above yellow solution at 7 to 9° C. under a nitrogen stream. After stirred at 9 to 14° C. for 2 hours, the reaction solution was filtered through Celite. The Celite was washed with 560 mL of 1,4-dioxane to obtain a reddish-purple solution. Under a nitrogen stream, a solution of 36.4 g (0.375 mol) of maleimide in 320 mL of 1,4-dioxane was added dropwise at 9 to 12° C. to the obtained reddish-purple solution over 8 minutes. The mixture was stirred at 12 to 22° C. for 1 hour to obtain a yellow solution. The obtained yellow solution was added dropwise to 1120 mL of 1,4-dioxane heated to 96° C. over 94 minutes under a nitrogen stream. The mixture was stirred at the same temperature for 1 hour and then cooled to room temperature. The obtained reaction solution was concentrated to 160 g at 50° C. under a reduced pressure, 240 mL of ethanol was added to the residue, and the mixture was further concentrated to 200 g at 50° C. under a reduced pressure. The precipitated solid was collected by filtration, washed with 80 mL of ethanol, and dried at 50° C. under a reduced pressure to obtain 53.9 g of the titled compound as a white solid. (Yield 49%)

Mass spectrum (CI, m/z): 294, 296[M$^+$+1]

$^1$H-NMR spectrum (400 MHz, DMSO-d$_6$) δppm: 10.97 (br. s, 1H), 7.54 (dd, J=1.6, 1.7 Hz, 1H), 7.50 (ddd, J=1.6, 1.7, 7.6 Hz, 1H), 7.37 (ddd, J=1.6, 1.6, 7.7 Hz, 1H), 7.33 (dd, J=7.6, 7.7 Hz, 1H), 2.91 (s, 2H), 1.82 (q, J=7.4 Hz, 2H), 0.78 (t, J=7.4 Hz, 3H)

Reference Example 3-(b): (1R,5S,6r)-tert-butyl 6-(3-bromophenyl)-6-ethyl-3-azabicyclo[3.1.0]hexane-3-carboxylate 700 mL (630 mmol) of a 0.9 M borane-tetrahydrofuran complex/tetrahydrofuran solution was added dropwise to a solution of 30.9 g (105 mmol) of (1R,5S,6r)-6-(3-bromophenyl)-6-ethyl-3-azabicyclo[3.1.0]hexane-2,4-dione, which was obtained in Reference Example 3-(a), in 150 mL of tetrahydrofuran with stirring at 0° C. under an argon stream. The obtained reaction solution was heated under reflux at a bath temperature of 75° C. for 3 hours. The reaction solution was cooled with ice, and 231 mL (1390 mmol) of 6 N hydrochloric acid was added dropwise. Then, the mixture was heated under reflux at a bath temperature of 75° C. The obtained reaction solution was cooled with ice, 600 mL of water and 600 mL of tert-butyl methyl ether were added, and the mixture was stirred at room temperature. The obtained reaction solution was separated to obtain an aqueous layer, and the aqueous layer was washed with 600 mL of tert-butyl methyl ether. Then, 305 mL (1530 mmol) of a 5 N aqueous sodium hydroxide solution was added to the obtained aqueous layer, 350 mL of tetrahydrofuran and 23 mL (100 mmol) of di-tert-butyl dicarbonate were then added, and the mixture was stirred at room temperature for 2 hours. Then, 300 mL of tert-butyl methyl ether was added to the reaction solution to obtain an organic layer by liquid separation. The organic layer was washed with 200 mL of 1 N hydrochloric acid, then with 200 mL of a 1 N aqueous sodium hydroxide solution, and then with a saturated aqueous sodium chloride solution. The organic layer was dried with anhydrous magnesium sulfate, filtered, and then concentrated under a reduced pressure.

The above-mentioned synthesis reaction and post-treatment operation were performed twice, the obtained two residues were mixed and subjected to silica gel column chromatography (600 g) (elution solvent: hexane:ethyl acetate=50:50 (V/V)), and a fraction containing a desired product was concentrated under a reduced pressure to obtain 69.4 g of the titled compound as a white solid. (Yield 90%)

Mass spectrum (CI, m/z): 366, 368[M$^+$+1]

$^1$H-NMR spectrum (400 MHz, CDCl$_3$) δppm: 7.40 (dd, J=1.6, 1.7 Hz, 1H), 7.33 (ddd, J=1.7, 1.8, 7.4 Hz, 1H), 7.18 (ddd, J=1.6, 1.8, 7.6 Hz, 1H), 7.15 (dd, J=7.4, 7.6 Hz, 1H), 3.64 (dd, J=5.3, 11.7 Hz, 1H), 3.59 (dd, J=5.2, 11.4 Hz, 1H), 3.54 (d, J=11.7 Hz, 1H), 3.47 (d, J=11.4 Hz, 1H), 1.91 (dd, J=5.3, 7.9 Hz, 1H), 1.87 (dd, J=5.2, 7.9 Hz, 1H), 1.60-1.53 (m, 2H), 1.47 (s, 9H), 0.82 (t, J=7.4 Hz, 3H)

Reference Example 3-(c): (1R,5S,6r)-tert-butyl 6-[3-(cyclopropanesulfonamido)phenyl]-6-ethyl-3-azabicyclo[3.1.0]hexane-3-carboxylate 29.8 g (246 mmol) of cyclopropanesulfonamide, 4.82 g (11.4 mmol) of tert-butyl XPhos, 1.38 g (3.77 mmol) of bis(η3-allyl-μ-chloropalladium), and 36.6 g (265 mmol) of potassium carbonate were added sequentially to a solution of 69.3 g (189 mmol) of (1R,5S,6r)-tert-butyl 6-(3-bromophenyl)-6-ethyl-3-azabicyclo[3.1.0]hexane-3-carboxylate, which was obtained in Reference Example 3-(b), in 400 mL of toluene with stirring under an argon stream, and the mixture was stirred at room temperature for 10 minutes, and was then stirred for 1.5 hours while heated at 110° C. The obtained reaction solution was filtered through Celite, the Celite was washed with toluene, and the filtrate was concentrated under a reduced pressure. Then, 300 mL of tert-butyl methyl ether and 300 mL of a 1 N aqueous sodium hydroxide solution were added to the obtained residue to obtain an aqueous layer by liquid separation. Then, 160 mL of 2 N hydrochloric acid and 300 mL of tert-butyl methyl ether were added to the obtained aqueous layer to obtain an organic layer by liquid separation. The organic layer was washed with a saturated aqueous sodium chloride solution, dried with anhydrous magnesium sulfate, and concentrated under a reduced pressure. Then, 200 mL of hexane and 22 mL of ethyl acetate were added to the obtained residue, and the mixture was stirred at room temperature for 30 minutes and then stirred with ice cooling for 10 minutes. The precipitated solid was collected by filtration and dried at 50° C. under a reduced pressure to obtain 54.4 g of the titled compound as a white solid. (Yield 70%)

Mass spectrum (CI, m/z): 407[M$^+$+1]

$^1$H-NMR spectrum (400 MHz, CDCl$_3$) δppm: 7.26 (dd, J=7.8, 7.8 Hz, 1H), 7.16 (dd, J=1.9, 1.9 Hz, 1H), 7.11-7.05 (m, 2H), 6.34 (s, 1H), 3.65 (dd, J=5.3, 11.4 Hz, 1H), 3.60 (dd, J=5.3, 11.5 Hz, 1H), 3.54 (d, J=11.4 Hz, 1H), 3.48 (d, J=11.5 Hz, 1H), 2.46 (tt, J=4.8, 8.0 Hz, 1H), 1.90 (dd, J=8.0, 5.2 Hz, 1H), 1.89 (dd, J=8.0, 5.2 Hz, 1H), 1.64-1.53 (m, 2H), 1.47 (s, 9H), 1.20-1.12 (m, 2H), 1.00-0.93 (m, 2H), 0.82 (t, J=7.4 Hz, 3H)

Reference Example 3-(d): N-{3-[(1R,5S,6r)-6-ethyl-3-azabicyclo[3.1.0]hexan-6-yl]phenyl}cyclopropanesulfonamide hydrochloride 434 mL (1740 mmol) of a 4 N hydrogen chloride/1,4-dioxane solution was added to a solution of 54.3 g (134 mmol) of (1R,5S,6r)-tert-butyl 6-[3-(cyclopropanesulfonamido)phenyl]-6-ethyl-3-azabicyclo[3.1.0]hexane-3-carboxylate, which was obtained in Reference Example 3-(c), in 70.6 mL of 1,4-dioxane with stirring under an argon stream, and the mixture was stirred at room temperature for 4 hours. The obtained reaction mixture was filtered and washed with 1,4-dioxane. The obtained solid was dried at 50° C. under a reduced pressure for 1 hour, and 80 mL of ethyl acetate was added. The mixture was stirred for 1 hour, filtered, and dried at 50° C. under a reduced pressure to obtain 42.1 g of the titled compound as a white solid. (Yield 92%)

Mass spectrum (CI, m/z): 307[M$^+$+1]

$^1$H-NMR spectrum (400 MHz, DMSO-d$_6$) δppm: 10.12 (br. s, 1H), 9.71 (s, 1H), 9.41 (br. s, 1H), 7.26 (dd, J=7.8, 7.9 Hz, 1H), 7.15 (dd, J=1.5, 2.0 Hz, 1H), 7.08 (ddd, J=1.0, 2.0, 7.9 Hz, 1H), 7.00 (ddd, J=1.0, 1.5, 7.8 Hz, 1H), 3.75-3.52 (m, 2H), 3.27-3.09 (m, 2H), 2.58 (tt, J=5.1, 7.7 Hz, 1H), 2.21-2.08 (m, 2H), 1.61 (q, J=7.2 Hz, 2H), 1.00-0.83 (m, 4H), 0.76 (t, J=7.2 Hz, 3H)

Reference Example 4-(a): 2-methoxy-2,3-dihydro-1H-indene-2-carbonitrile 47.5 g (149 mmol) of zinc iodide was added to a solution of 53.0 g (297 mmol) of 2,2-dimethoxy-2,3-dihydro-1H-indene (see Bioorganic and Medicinal Chemistry Letters, 19 (2009) 5927-5930)) and 44.5 mL (357 mmol) of trimethylsilyl cyanide in 150 ml of methylene chloride with stirring at 0° C. under an argon stream, and the mixture was stirred at the same temperature for 10 minutes and then further stirred at room temperature for 1 hour. Water was added to the obtained reaction solution, and the mixture was subjected to extraction with ethyl acetate. The organic layer was washed with a saturated aqueous sodium hydrogen carbonate solution, dried with anhydrous magnesium sulfate, and concentrated under a reduced pressure. The obtained residue was subjected to silica gel column chromatography (elution solvent: hexane:ethyl acetate=100:0→92:8 (V/V)), and a fraction containing a desired product was concentrated under a reduced pressure to obtain 24.7 g of the titled compound as a colorless oil. (Yield 48%)

Mass spectrum (EI, m/z): 173[M+]

$^1$H-NMR spectrum (400 MHz, CDCl$_3$) δppm: 7.25-7.21 (m, 4H), 3.51 (s, 3H), 3.50 (d, J=16.2 Hz, 2H), 3.39 (d, J=16.2 Hz, 2H)

Reference Example 4-(b): 2-methoxy-2,3-dihydro-1H-indene-2-carbaldehyde 98 mL (98 mmol) of a 1.0 M diisobutylaluminum hydride/toluene solution was added to a solution of 13.0 g (75.1 mmol) of 2-methoxy-2,3-dihydro-1H-indene-2-carbonitrile, which was obtained in Reference Example 4-(a), in 42 mL of toluene with stirring at −78° C. under an argon stream, and the mixture was stirred at room temperature for 0.5 hours. Then, 91 mL of 2 N hydrochloric acid was added to the obtained reaction solution with ice cooling, and the mixture was subjected to extraction with ethyl acetate. The organic layer was washed with a saturated aqueous sodium chloride solution, dried with anhydrous magnesium sulfate, filtered, and concentrated under a reduced pressure to obtain 6.5 g of the titled compound as a pale yellow oil. (Yield 49%)

Mass spectrum (CI, m/z): 177[M$^+$+1]

$^1$H-NMR spectrum (400 MHz, CDCl$_3$) δppm: 9.77 (s, 1H), 7.23-7.16 (m, 4H), 3.34 (d, J=16.7 Hz, 2H), 3.33 (s, 3H), 3.17 (d, J=16.7 Hz, 2H)

Reference Example 4-(c): N-(3-{(1R,5S,6r)-6-ethyl-3-[(2-methoxy-2,3-dihydro-1H-inden-2-yl)methyl]-3-azabicyclo[3.1.0]hexan-6-yl}phenyl)cyclopropanesulfonamide 8.50 g (24.8 mmol) of N-{3-[(1R,5S,6r)-6-ethyl-3-azabicyclo[3.1.0]hexan-6-yl]phenyl}cyclopropanesulfonamide hydrochloride, which was obtained in Reference Example 3-(d), and 3.63 mL (26.0 mmol) of triethylamine were added to a solution of 4.81 g (27.3 mmol) of 2-methoxy-2,3-dihydro-1H-indene-2-carbaldehyde, which was obtained in Reference Example 4-(b), in 29 mL of methylene chloride with stirring under an argon stream, and the mixture was stirred at room temperature for 10 minutes. Then, 13.1 g (61.8 mmol) of sodium triacetoxyborohydride was added to the reaction solution, and the mixture was stirred at room temperature for 2.5 hours. Water was added to the obtained reaction solution, and the mixture was subjected to extraction with ethyl acetate. The organic layer was washed with a saturated aqueous sodium hydrogen carbonate solution, then dried with anhydrous magnesium sulfate, and concentrated under a reduced pressure. The obtained residue was subjected to silica gel column chromatography (135 g of silica gel, elution solvent: hexane:ethyl acetate=52:48→31:69 (V/V)), and a fraction containing a desired product was concentrated under a reduced pressure to obtain 10.6 g of the titled compound as a slightly yellow oil. (Yield 83%)

Mass spectrum (CI, m/z): 467[M$^+$+1]

$^1$H NMR spectrum (400 MHz, CDCl$_3$) δppm: 7.23 (dd, J=7.9, 7.8 Hz, 1H), 7.20-7.12 (m, 5H), 7.12-7.08 (m, 1H), 7.04 (ddd, J=1.0, 2.3, 7.9 Hz, 1H), 6.20 (br. s, 0.9H), 3.24 (s, 3H), 3.17 (d, J=9.5 Hz, 2H), 3.11 (d, J=16.5 Hz, 2H), 3.00 (d, J=16.5 Hz, 2H), 2.97-2.93 (m, 2H), 2.73 (s, 2H), 2.45 (tt, J=4.8, 8.0 Hz, 1H), 1.95 (q, J=7.4 Hz, 2H), 1.78-1.69 (m, 2H), 1.20-1.12 (m, 2H), 0.99-0.91 (m, 2H), 0.82 (t, J=7.4 Hz, 3H)

Reference Example 4-(d): N-(3-{(1R,5S,6r)-6-ethyl-3-[(2-methoxy-2,3-dihydro-1H-inden-2-yl)methyl]-3-azabicyclo[3.1.0]hexan-6-yl}phenyl)cyclopropanesulfonamide hydrochloride 68 μL (0.27 mmol) of a 4 N hydrogen chloride/1,4-dioxane solution was added to a solution of 85 mg (0.18 mmol) of N-(3-{(1R,5S,6r)-6-ethyl-3-[(2-methoxy-2,3-dihydro-1H-inden-2-yl)methyl]-3-azabicyclo[3.1.0]hexan-6-yl}phenyl)cyclopropanesulfonamide, which was obtained in the same manner as in Reference Example 4-(c), in 1.0 mL of 1,4-dioxane, and the mixture was stirred at room temperature for 10 minutes. After the completion of reaction, the reaction solution was concentrated under a reduced pressure. Then, 1.0 mL of ethanol was added to the residue, and the precipitated solid was collected by filtration and dried at 50° C. under a reduced pressure to quantitatively obtain 97 mg of the titled compound as a white solid.

(Calculated as a Monohydrochloride)

Mass spectrum (FAB, m/z): 467[M$^+$+1]

$^1$H-NMR spectrum (400 MHz, CD$_3$OD) δppm: 7.29 (dd, J=8.0, 7.9 Hz, 1H), 7.28-7.16 (m, 5H), 7.13 (ddd, J=8.0, 2.2, 0.9 Hz, 1H), 7.12-7.06 (m, 1H), 4.67-3.90 (m, 2H), 3.67-3.54 (m, 2H), 3.28-3.04 (m, 6H), 3.14 (s, 3H), 2.52 (tt, J=7.9, 4.9 Hz, 1H), 2.43-2.24 (m, 2H), 1.84 (q, J=7.3 Hz, 2H), 1.05-0.85 (m, 4H), 0.88 (t, J=7.3 Hz, 3H)

Reference Example 5-(a): 1-allyl-4,4-difluorocyclohexanol

A solution of 41.2 g (307 mmol) of 4,4-difluorocyclohexanone in 50 mL of tetrahydrofuran was added dropwise to 230 mL (460 mmol) of a 2.0 M allylmagnesium chloride/tetrahydrofuran solution with stirring at 0° C. under an argon atmosphere, and the mixture was stirred at the same temperature for 1 hour. Then, the obtained reaction solution was adjusted to pH 2.5 by adding 1 N hydrochloric acid, and was subjected to extraction with hexane. The organic layer was dried with anhydrous magnesium sulfate and concentrated under a reduced pressure. The obtained residue was distilled (24 hPa, 73.5-79.5° C.) to obtain 44.4 g of the titled compound as a colorless oil. (Yield 82%)

$^1$H-NMR spectrum (400 MHz, CDCl$_3$) δppm: 5.86 (tdd, J=7.4, 10.0, 17.2 Hz, 1H), 5.26-5.20 (m, 1H), 5.20-5.11 (m, 1H), 2.29-2.22 (m, 2H), 2.21-1.86 (m, 4H), 1.76-1.61 (m, 4H)

Reference Example 5-(b): 1-allyl-4,4-difluoro-1-methoxycyclohexane 25.0 g (142 mmol) of 1-allyl-4,4-difluorocyclohexanol, which was obtained in Reference Example 5-(a), was added dropwise to a solution of 18.6 g (426 mmol) of sodium hydride (55% dispersion in mineral oil) in 250 mL of tetrahydrofuran at 27° C. under an argon stream. The reaction solution was heated to 37° C., and then 27 mL (430 mmol) of methyl iodide was added dropwise so that the temperature of the mixture did not exceed 55° C., and the mixture was stirred at a bath temperature of 45° C. for 1 hour. The reaction solution was cooled to room temperature, 300 mL of a saturated aqueous ammonium chloride solution was added dropwise, and the mixture was subjected to extraction by adding 200 mL of ethyl acetate. The organic layer was washed with 300 mL of a saturated aqueous sodium chloride solution, then dried with anhydrous magnesium sulfate, and concentrated under a reduced pressure. The obtained residue was subjected to silica gel column chromatography (silica gel 300 g, elution solvent: hexane:ethyl acetate=100:0→80:20 (V/V)), and a fraction containing a desired product was concentrated under a reduced pressure to obtain 25.3 g of the titled compound as a slightly yellow oil. (Yield 94%)

Mass spectrum (CI, m/z): 191[M$^+$+1]

$^1$H-NMR spectrum (400 MHz, CDCl$_3$) δppm: 5.79 (tdd, J=7.2, 10.1, 17.1 Hz, 1H), 5.15-5.04 (m, 2H), 3.20 (s, 3H), 2.25 (ddd, J=1.2, 1.2, 7.2 Hz, 2H), 2.11-1.81 (m, 6H), 1.59-1.46 (m, 2H)

Reference Example 5-(c): 3-(4,4-difluoro-1-methoxycyclohexyl)propan-1-ol

A solution of 25.0 g (131 mmol) of 1-allyl-4,4-difluoro-1-methoxycyclohexane, which was obtained in Reference Example 5-(b), in tetrahydrofuran (125 ml) was added dropwise to 800 mL (400 mmol) of a 0.5 M 9-borabicyclo[3.3.1]nonane/tetrahydrofuran solution at 0° C. under an argon stream, and the mixture was stirred at room temperature for 3 hours. Then, 240 mL (1200 mmol) of a 5 N aqueous sodium hydroxide solution and 120 mL (1170 mmol) of 30% hydrogen peroxide water were added dropwise at 0° C., and the mixture was stirred at room temperature for 2 hours. Then, 600 mL of water was added to the reaction solution, and the mixture was subjected to extraction with 300 mL of ethyl acetate. The aqueous layer was subjected to extraction with 300 mL of ethyl acetate twice. The organic layers were mixed, washed with 500 mL of a saturated aqueous sodium chloride solution twice, then dried with anhydrous magnesium sulfate, and concentrated under a reduced pressure. The obtained residue was subjected to silica gel column chromatography (silica gel 300 g, elution solvent: hexane:ethyl acetate=40:60→20:80 (V/V)), and a fraction containing a desired product was concentrated under a reduced pressure to obtain 25.9 g of the titled compound as a colorless oil. (Yield 95%)

Mass spectrum (CI, m/z): 209[M$^+$+1]

$^1$H-NMR spectrum (400 MHz, DMSO-d$_6$) δppm: 4.40 (t, J=5.2 Hz, 1H), 3.42-3.34 (m, 2H), 3.05 (s, 3H), 1.97-1.30 (m, 12H)

Reference Example 5-(d): 3-(4,4-difluoro-1-methoxycyclohexyl)propanal 12 mL of an aqueous solution containing 4.10 g (34.5 mmol) of potassium bromide and 53.0 mg (0.339 mmol) of 2,2,6,6-tetramethylpiperidine-1-oxylradical were added to a solution of 7.00 g (33.6 mmol) of 3-(4,4-difluoro-1-methoxycyclohexyl)propan-1-ol, which was obtained in Reference Example 5-(c), in 60 mL of methylene chloride with stirring at 0° C. under an argon stream, and the mixture was stirred at the same temperature for 5 minutes. Then, 25 mL (48.6 mmol) of a 12 wt % aqueous sodium hypochlorite solution and 60 ml of an aqueous solution containing 2.82 g (33.6 mmmol) of sodium hydrogen carbonate were added dropwise to the reaction solution at 0° C., and the mixture was stirred at the same temperature for 30 minutes. Then, 12 mL of an aqueous solution containing 6.90 g (43.6 mmol) of sodium thiosulfate was added to the reaction solution. The organic layer was separated, washed with 60 mL of a saturated aqueous sodium hydrogen carbonate solution and then with 60 mL of a saturated aqueous sodium chloride solution, dried with anhydrous magnesium sulfate, and then concentrated under a reduced pressure to obtain 6.0 g of the titled compound as a pale yellow oil. (Yield 87%)

Mass spectrum (CI, m/z): 207[M$^+$+1]

$^1$H-NMR spectrum (400 MHz, CDCl$_3$) δppm: 9.83 (t, J=1.3 Hz, 1H), 3.12 (s, 3H), 2.53-2.47 (m, 2H), 2.04-1.75 (m, 8H), 1.54-1.43 (m, 2H)

Reference Example 5-(e): N-(3-{(1R,5S,6r)-3-[3-(4,4-difluoro-1-methoxycyclohexyl)propyl]-6-ethyl-3-azabicyclo[3.1.0]hexan-6-yl}phenyl)cyclopropanesulfonamide 8.40 g (24.5 mmol) of N-{3-[(1R,5S,6r)-6-ethyl-3-azabicyclo[3.1.0]hexan-6-yl]phenyl}cyclopropanesulfonamide hydrochloride, which was obtained in Reference Example 3-(d), and 3.2 mL (23 mmol) of triethylamine were added to a solution of 6.00 g (29.1 mmol) of 3-(4,4-difluoro-1-methoxycyclohexyl)propanal, which was obtained in Reference Example 5-(d), in 110 mL of methylene chloride, and the mixture was stirred at 0° C. for 10 minutes. Then, 12.2 g (57.6 mmol) of sodium triacetoxyborohydride was added to the reaction solution, and the mixture was stirred at room temperature for 30 minutes. Then, 120 mL of a saturated aqueous sodium hydrogen carbonate solution was added to the obtained reaction solution, and the mixture was subjected to extraction with 120 mL of methylene chloride. The organic layer was washed with 120 mL of a saturated aqueous sodium chloride solution, dried with anhydrous magnesium sulfate, and then concentrated under a reduced pressure. The residue was subjected to silica gel column chromatography (elution solvent: hexane:ethyl acetate=50:50→30:70 (V/V)), and a fraction containing a desired compound was concentrated under a reduced pressure to obtain 12 g of the titled compound as a pale yellow oil. (Yield 99%)

Mass spectrum (CI, m/z): 497[M$^+$+1]

$^1$H-NMR spectrum (400 MHz, CDCl$_3$) δppm: 7.23 (dd, J=7.8, 7.9 Hz, 1H), 7.16 (dd, J=1.8, 2.0 Hz, 1H), 7.12-7.07 (m, 1H), 7.04 (ddd, J=1.0, 2.0, 7.9 Hz, 1H), 6.28 (br. s, 1H), 3.15 (s, 3H), 3.00 (d, J=9.5 Hz, 2H), 2.87-2.69 (m, 2H), 2.53-2.38 (m, 3H), 2.10-1.39 (m, 16H), 1.20-1.12 (m, 2H), 1.00-0.90 (m, 2H), 0.81 (t, J=7.4 Hz, 3H)

Reference Example 5-(f): N-(3-{(1R,5S,6r)-3-[3-(4,4-difluoro-1-methoxycyclohexyl)propyl]-6-ethyl-3-azabicyclo[3.1.0]hexan-6-yl}phenyl)cyclopropanesulfonamide hydrochloride 861 µL (3.44 mmol) of a 4 N hydrogen chloride/ethyl acetate solution was added to a solution of 570 mg (1.15 mmol) of N-(3-{(1R,5S,6r)-3-[3-(4,4-difluoro-1-methoxycyclohexyl)propyl]-6-ethyl-3-azabicyclo[3.1.0]hexan-6-yl}phenyl)cyclopropanesulfonamide, which was obtained in the same manner as in Reference Example 5-(e), in 3.0 mL ethyl acetate, and the mixture was stirred at room temperature for 30 minutes. After the completion of reaction, the reaction solution was concentrated under a reduced pressure. Then, 1.0 mL of acetone was added to the residue, and the mixture was stirred for 1 hour. The precipitated solid was collected by filtration and dried under a reduced pressure to obtain 475 mg of the titled compound as a white solid. (Yield 78%, calculated as a monohydrochloride)

Mass spectrum (CI, m/z): 497[M$^+$+1]

$^1$H-NMR spectrum (400 MHz, CD$_3$OD) δppm: 7.28 (dd, J=8.0, 7.8 Hz, 1H), 7.25 (dd, J=2.0, 1.9 Hz, 1H), 7.12 (ddd, J=8.0, 2.0, 1.1 Hz, 1H), 7.1 (ddd, J=7.8, 1.9, 1.1 Hz, 1H), 4.10-3.75 (m, 2H), 3.30-2.97 (m, 4H), 3.18 (s, 3H), 2.51 (tt, J=7.9, 4.9 Hz, 1H), 2.36-2.27 (m, 2H), 2.06-1.45 (m, 14H), 1.05-0.85 (m, 4H), 0.88 (t, J=7.3 Hz, 3H)

Reference Example 6-(a): 3-(4,4-difluorocyclohexyl)propionic acid 207 mL (1490 mmol) of triethylamine was added dropwise to 140 mL (3650 mmol) of formic acid with stirring and ice cooling under an argon stream at 30° C. or less. Then, 20.7 g (140 mmol) of 4,4-difluorocyclohexanecarbaldehyde and 20.5 g (142 mmol) of 2,2-dimethyl-1,3-dioxane-4,6-dione were added at 10° C. or less, and the mixture was stirred at 100° C. for 5 hours. The reaction solution was cooled to room temperature and added to a mixed solution of 1000 mL of a 5 N aqueous sodium hydroxide solution and 1000 mL of diethyl ether to obtain an aqueous layer by liquid separation. Then, 400 mL of 6 N hydrochloric acid was added to the obtained aqueous layer, and the mixture was subjected to extraction with 600 mL of methylene chloride twice. The obtained organic layer was washed with 600 mL of a saturated aqueous sodium chloride solution, then dried with anhydrous magnesium sulfate, and concentrated under a reduced pressure to obtain 24.3 g of the titled compound as a white solid. (Yield: 91%)

Mass spectrum (CI, m/z): 193[$M^+$+1]

$^1$H-NMR spectrum (400 MHz, DMSO-$d_6$) δppm: 12.04 (br. s, 1H), 2.23 (t, J=7.6 Hz, 2H), 2.05-1.89 (m, 2H), 1.86-1.63 (m, 4H), 1.50-1.42 (m, 2H), 1.41-1.29 (m, 1H), 1.21-1.03 (m, 2H)

Reference Example 6-(b):
3-(4,4-difluorocyclohexyl)propan-1-ol 420 mL (378 mmol) of a 0.9 M borane-tetrahydrofuran complex/tetrahydrofuran solution was added dropwise to a solution of 24.3 g (126 mmol) of 3-(4,4-difluorocyclohexyl) propionic acid, which was obtained in Reference Example 6-(a), in 243 mL of tetrahydrofuran with stirring under an argon stream so that the temperature of the mixture did not exceed 10° C., and the mixture was heated with stirring under reflux for 1.5 hours. The reaction solution was cooled to room temperature, and 120 mL of methanol and 10 mL of water were added. The reaction solution was concentrated under a reduced pressure and mixed with 500 mL of tert-butyl methyl ether and 500 mL of 1 N hydrochloric acid to obtain an organic layer by liquid separation. The organic layer was washed with 500 mL of a 1 N aqueous sodium hydroxide solution and 500 mL of a saturated aqueous sodium chloride solution, then dried with anhydrous magnesium sulfate, and concentrated under a reduced pressure to quantitatively obtain 24.3 g of the titled compound as a colorless oil.

$^1$H-NMR spectrum (400 MHz, DMSO-$d_6$) δppm: 4.34 (t, J=5.4 Hz, 1H), 3.41-3.33 (m, 2H), 2.04-1.90 (m, 2H), 1.86-1.62 (m, 4H), 1.50-1.03 (m, 7H)

Reference Example 6-(c):
3-(4,4-difluorocyclohexyl)propanal 13.6 mL of an aqueous solution containing 5.50 g (46.2 mmol) of potassium bromide and 70.0 mg (0.448 mmol) of 2,2,6,6-tetramethylpiperidine-1-oxylradical were added to a solution of 8.00 g (44.9 mmol) of 3-(4,4-difluorocyclohexyl) propan-1-ol, which was obtained in Reference Example 6-(b), in 67 ml of methylene chloride with stirring under an argon stream, and the mixture was stirred at room temperature for 5 minutes. Then, 30 mL of a 12 wt % aqueous sodium hypochlorite solution and 70 mL of an aqueous solution containing 3.77 g (44.9 mmol) of sodium hydrogen carbonate were added dropwise to the reaction solution at 0° C., and the mixture was stirred at the same temperature for 30 minutes. Then, 14 mL of an aqueous solution containing 10 g (63.2 mmol) of sodium thiosulfate was added to the reaction solution to obtain an organic layer by liquid separation. The organic layer was washed with 70 mL of a saturated aqueous sodium hydrogen carbonate solution and 70 mL of a saturated aqueous sodium chloride solution, dried with anhydrous magnesium sulfate, and then concentrated under a reduced pressure to obtain 7.2 g of the titled compound as a pale yellow oil. (Yield 91%)

$^1$H-NMR spectrum (400 MHz, CDCl$_3$) δppm: 9.78 (t, J=1.6 Hz, 1H), 2.48 (dt, J=1.6, 7.5 Hz, 2H), 2.16-2.01 (m, 2H), 1.83-1.57 (m, 6H), 1.44-1.20 (m, 3H)

Reference Example 6-(d): N-(3-{(1R,5S,6r)-3-[3-(4,4-difluorocyclohexyl)propyl]-6-ethyl-3-azabicyclo[3.1.0]hexan-6-yl}phenyl)cyclopropanesulfonamide 8.40 g (24.5 mmol) of N-3-[(1R,5S,6r)-6-ethyl-3-azabicyclo[3.1.0]hexan-6-yl]phenyl}cyclopropanesulfonamide hydrochloride, which was obtained in Reference Example 3-(d), and 3.4 mL (24 mmol) of triethylamine were added to a solution of 6.60 g (37.5 mmol) of 3-(4,4-difluorocyclohexyl)propanal, which was obtained in Reference Example 6-(c), in 120 mL of methylene chloride, and the mixture was stirred at 0° C. for 10 minutes. Then, 13.0 g (61.3 mmol) of sodium triacetoxyborohydride was added to the reaction solution, and the mixture was stirred at room temperature for 0.5 hours. Then, 120 mL of a saturated aqueous sodium hydrogen carbonate solution was added to the obtained reaction solution, and the mixture was subjected to extraction with methylene chloride. The organic layer was washed with a saturated aqueous sodium chloride solution, dried with anhydrous magnesium sulfate, and then concentrated under a reduced pressure. The residue was subjected to silica gel column chromatography (elution solvent: hexane:ethyl acetate=45:55→20:80 (V/V)), and a fraction containing a desired product was concentrated under a reduced pressure to obtain 11.3 g of the titled compound as a pale yellow oil. (Yield 99%)

Mass spectrum (CI, m/z): 467[$M^+$+1]

$^1$H-NMR spectrum (400 MHz, CDCl$_3$) δppm: 7.23 (d, J=7.8, 7.8 Hz, 1H), 7.16 (dd, J=2.1, 1.9 Hz, 1H), 7.12-7.07 (m, 1H), 7.04 (ddd, J=1.1, 2.1, 7.8 Hz, 1H), 6.33 (br. s, 1H), 2.97 (d, J=9.5 Hz, 2H), 2.80-2.74 (m, 2H), 2.46-2.37 (m, 3H), 2.13-2.01 (m, 2H), 1.95 (q, J=7.2 Hz, 2H), 1.83-1.22 (m, 13H), 1.19-1.13 (m, 2H), 0.99-0.91 (m, 2H), 0.81 (t, J=7.2 Hz, 3H)

Reference Example 6-(e): N-(3-{(1R,5S,6r)-3-[3-(4,4-difluorocyclohexyl)propyl]-6-ethyl-3-azabicyclo[3.1.0]hexan-6-yl}phenyl)cyclopropanesulfonamide hydrochloride 1.5 mL (6.0 mmol) of a 4 N hydrogen chloride/ethyl acetate solution was added to a solution of 1.42 g (3.04 mmol) of N-(3-{(1R,5S,6r)-3-[3-(4,4-difluorocyclohexyl)propyl]-6-ethyl-3-azabicyclo[3.1.0]hexan-6-yl}phenyl)cyclopropanesulfonamide, which was obtained in the same manner as in Reference Example 6-(d), in 15 mL of ethyl acetate, and the mixture was stirred at room temperature for 15 minutes. After the completion of reaction, the reaction solution was concentrated under a reduced pressure. Then, 15 mL of acetone was added to the residue, and the mixture was concentrated under a reduced pressure. Further, 15 mL of acetone was added to the residue, and the mixture was stirred at room temperature for 2 hours. The precipitated solid was collected by filtration and dried at 45° C. under a reduced pressure to obtain 1.10 g of the titled compound as a white solid. (Yield 72%, calculated as a monohydrochloride)

Mass spectrum (CI, m/z): 467[$M^+$+1]

$^1$H-NMR spectrum (400 MHz, CD$_3$OD) δppm: 7.28 (dd, J=7.9, 7.8 Hz, 1H), 7.24 (dd, J=2.0, 1.9 Hz, 1H), 7.12 (ddd, J=7.9, 2.0, 1.0 Hz, 1H), 7.10-7.06 (m, 1H), 4.61-3.73 (m, 2H), 3.40-2.85 (t, 4H), 2.51 (tt, J=7.8, 4.9 Hz, 1H), 2.37-2.28 (m, 2H), 2.10-1.97 (m, 2H), 1.88-1.65 (m, 8H), 1.51-1.19 (m, 5H), 1.04-0.85 (m, 4H), 0.87 (t, J=7.3 Hz, 3H)

The test substances used in the following Pharmacological Test Examples 1 to 6 were Reference Example 2-(d), Reference Example 4-(d), Reference Example 5-(f), Reference Example 6-(e), and Comparative Compound 1.

Comparative Compound 1 is the compound described in WO 2003/035622, N-(3-{(1R,5S,6r)-6-ethyl-3-[(2-hydroxy-2,3-dihydro-1H-inden-2-yl)methyl]-3-azabicyclo[3.1.0]hexan-6-yl}phenyl)methanesulfonamide methanesulfonate.

Pharmacological Test Example 1

(1) Preparation of Human μ-Opioid Receptor Expression Cell Membrane

Cells in which a human μ-opioid receptor had been highly expressed was purchased from ChanTest (Cleveland). The cells were cultured in a carbon dioxide gas culturing apparatus by using a Ham's F12 culture medium (Invitrogen) containing 10% of fetal bovine blood serum, 1% of non-essential amino acids, 0.4 mg/ml of G418, 100 U/ml of penicillin and 100 μg/ml of streptomycin. The cultured cells were suspended by using a 0.25% trypsin 1 mM EDTA solution, the suspension was collected by using phosphate-buffered saline and centrifuged at 4° C. and 1,000 rpm for 10 minute to remove the supernatant, whereby a cell mass was obtained. The weight of the obtained cell mass was measured, a homogenized buffer (a 10 mM KCl, 1 mM $MgCl_2$-containing 50 mM tris buffer to which a protease inhibitor (Complete EDTA free, Roche) had been added, pH 7.4) in a 5.5-fold amount was added, and the resultant was homogenized repeatedly three times in a Polytron homogenizer (SMT Multi Disperser PB95) under ice cooling at 13,000 rpm for 30 seconds, the product was then centrifuged at 4° C. and 20,000 rpm for 20 minutes, and the supernatant was removed to give a sediment. Similar homogenization and centrifugation operations were repeated on the sediment, a homogenized buffer was added again to the obtained sediment, and the resultant was similarly homogenized to give a membrane fraction solution. The obtained membrane fraction solution was dispensed, rapidly frozen and stored under freezing at −70° C. or less until use. Furthermore, the protein concentration of the obtained membrane fraction solution was measured by using a BCA protein Assay Kit (Cat. 23227, Pierce) according to the protocol attached to the kit.

(2) Antagonist Activity Test Using [$^{35}$S]-GTPγS Bond as Index Using Human μ-Opioid Receptor-Expressing Cell Membrane The cell membrane fraction solution in which the human μ-opioid receptor had expressed, which had been stored under freezing, was melted, a GTP assay buffer (100 mM NaCl, 5 mM $MgCl_2$, 1 mM EDTA-containing 50 mM Hepes (pH 7.4)) was added thereto, and the resultant was homogenized repeatedly twice by using a Polytron homogenizer (SMT Multi Disperser PB95) under ice cooling at 12,000 rpm for 20 seconds to give a homogeneous solution, and the homogeneous solution was diluted to 0.036 mg/ml with a GTP assay buffer containing 18.2 μM of GDP (final concentration: 4 μg/ml). The dilution was incubated for 15 minutes or more under ice cooling until the reaction was initiated. Test substances were each dissolved in DMSO, diluted with DMSO up to a concentration of 100-fold of the test concentration, and the dilution was subjected to two-fold dilution with a GTP assay buffer to set the DMSO concentration to 50% (final concentration: 1% DMSO). [$^{35}$S]-GTPγS (NEG030X, Perkinelmer) was diluted with a GTP assay buffer so as to be 0.616 nM (final concentration: 0.08 nM). The resultant was diluted with a GTP assay buffer so as to be 200 nM (final concentration: 10 nM) by using [D-Ala$^2$, N-Me-Phe$^4$, Gly$^5$-ol]-enkephalinacetate (DAMGO, Sigma) as a μ-opioid receptor agonist. WGA Coated PVT SPA Beads (RPNQ0001, Perkinelmer) were added so as to be 20 mg/ml with a GTP assay buffer, and the resultant was suspended (final concentration: 1 mg/well). 4 μL/well of a test substance solution, 10 μL/well of a DAMGO solution, 26 μL/well of a [$^{35}$S]-GTPγS solution, 50 μL/well of a suspension liquid of WGA Coated PVT SPA Beads, and 110 μL/well of the membrane fraction solution were added to a 96 well plate (1450-401, Perkinelmer), the top part of the plate was sealed, and a reaction was performed at 30° C. for 60 minutes under stirring with a plate shaker. For each measurement plate, a well to which DMSO had been added instead of the test substance, and a well to which DMSO had been added instead of the test substance and a GTP assay buffer had been added instead of the DAMGO solution were prepared. Furthermore, after the reaction was completed, the reactant was centrifuged at room temperature and 1,000 rpm for 3 minutes, and the radioactivity was measured by a microplate scintillation luminescence counter (Perkinelmer).

(3) Calculation of $IC_{50}$ Value

The $IC_{50}$ value of the test substance was calculated by using Graphpad Prism 5. The inhibition ratio of the test substance at the respective concentrations were calculated with setting the reaction value of the well to which DMSO had been added instead of the test substance to be 0%, and the reaction value of the well to which DMSO had been added instead of the test substance and a GTP assay buffer had been added instead of the DAMGO solution to be 100%, and a value that represented 50% inhibition was deemed as $IC_{50}$ from the concentration-reaction curve, and the obtained value is described in Table 1. As a result, it was found that the compounds that were tested at this time had a μ-opioid receptor antagonistic activity.

The compounds used in this study were different from the present invention in salt or crystalline form, but $IC_{50}$ values would be the same since each value had been calculated in tests conducted using a solution in which the compound was dissolved in DMSO.

TABLE 1

| Example | $IC_{50}$ (nM) | Example | $IC_{50}$ | Example | $IC_{50}$ (nM) |
|---------|----------------|---------|----------|---------|----------------|
| 2-(d)   | 2.0            | 5-(f)   | 1.3      | Comparative Compound 1 | 1.3 |
| 4-(d)   | 3.6            | 6-(e)   | 1.5      |         |                |

Pharmacological Test Example 2

(1) Evaluation of anti-pruritic effect by using pruritus mice model to which morphine had been intracisternally administered The anti-pruritic effects of the compounds (I) were evaluated by using pruritus mice model to which morphine had been intracisternally administered.

As experimental animals, male ICR (Crlj: CD1(ICR): Charles River Japan) mice were used at 5 to 6-week old. The mice were placed in an acrylic cage (colorless and transparent, W 13.5 cm×D 9.5 cm×H 40 cm) for observing scratching behavior for 30 minutes or more to thereby allow the mice to get used to the observation environment, and the test substance solutions were forcedly orally administered to the test substance-administered groups. In addition, an administration vehicle was forcedly orally administered to the normal control group and the pathological control group. A necessary amount of the test substance was weighed and formed into a micropowder in an agate mortar, an administration vehicle, a 0.5 w/v % methyl cellulose 400 solution (Wako Pure Chemical Industries Ltd.) was added little by little, and preparation was performed by suspending or dissolving so as to give an intended concentration (from 0.025 to 3 mg/ml). The test doses were preset to suitable doses in the range in which the maximum dose is 30 mg/10 ml/kg.

The morphine solution, which induces pruritus, was prepared by dissolving morphine hydrochloride hydrate "Shionogi" (Shionogi & Co., Ltd.) in saline so as to be 0.3 nmol/5 µL. The morphine solutions were intracisternally administered at 5 µL/site to the test substance-administered groups at after 30-120 minutes of the administration of the test substance solutions, whereby a scratching behavior was induced. Based on 30 minutes after the forced oral administration of the test substance as a criterion, the time for the intracisternal administration of morphine was suitably set up to 120 minutes after at the maximum, with consideration for the times of maximum plasma concentration of the respective test substances, in the case when the in vivo pharmacokinetics of the test substance had been confirmed in advance. Furthermore, saline was intracisternally administered to the normal control group, and the above-mentioned morphine solution was intracisternally administered to the pathogenic control group, so as to be 5 µL/site at the same time as that of the test substance group after the forced oral administration of the administration vehicle in either case.

The behavior of each mouse within 60 minutes from the intracisternal administration of the morphine solution or saline was recorded by a digital video camera that was installed immediately above the acrylic cage, the images were stored in a digital video recorder, and the number of frequency of the scratching behavior was measured. The number of frequency of the scratching behavior was measured with deeming a behavior in which the mouse raised its hindlimb, scratched the facial surface and the peripheral sites thereof, and got the hindlimb off from the body within 30 minutes from after the intracisternal administration of the morphine or saline as one time.

(2) Calculation of anti-pruritic effect The anti-pruritic effect of each test substance was obtained as follows. As an inhibition ratio against the number of frequency of the scratching behavior on the pathological control group, the inhibition ratio (%) of the respective individuals and the average value thereof were calculated from the following formula, and an $ED_{50}$ value was calculated based on the obtained inhibition ratio.

Inhibition ratio of each individual (%)={1−(*A*−Vehicle)/(Morphine−Vehicle)}×100

Morphine: the average of the scratching number of the pathological control group
Vehicle: the average of the scratching number of the normal control group
A: the scratching number of each individual in the test substance-administered group (3) Calculation of $ED_{50}$ value An $ED_{50}$ value was obtained as a value of 50% inhibition, which was performed by nonlinear regression analysis from a reaction curve of the dose-scratching behavior inhibition ratio using biostatic analysis software GraphPad Prism 5 (GraphPad Software), and the obtained value was described in Table 2.

The compounds used in this study were different from the present invention in salt or crystalline form, but the $ED_{50}$ values of at least Reference Example 2-(d), Reference Example 5-(f), and Reference Example 6-(e) that are highly active were calculated by conducting tests using a solution in which these compounds were dissolved, so the values would be the same even though the salt or crystalline form is different.

TABLE 2

| Example | $ED_{50}$ (mg/kg) | Example | $ED_{50}$ (mg/kg) | Example | $ED_{50}$ (mg/kg) |
|---|---|---|---|---|---|
| 2-(d) | 0.83 | 5-(f) | 0.42 | Comparative Compound 1 | 2.6 |
| 4-(d) | 4.2 | 6-(e) | 0.50 | | |

Pharmacological Test Example 3

(1) Collection of Sample for Calculation of Concentration in Plasma

The concentration of the test substances in blood plasma was confirmed by using mice of the same week-old for the same dose as that used in the evaluation of the anti-pruritic effect. The test substance was administered by forced oral administration of an administration cehicle prepared in a similar manner to that in the evaluation of the anti-pruritic effect under a non-fasting condition. The blood samples were collected from the orbital venous plexus, within from 15 minutes after the administration of the test substance to after 180 minutes at the maximum, for multiple times including the timing at which the morphine solution was intracisternally administered, under inhalation anesthesia with diethyl ether or isoflurane using a heparin-treated hematocrit tubes. The collected blood samples were immediately ice-cooled and centrifuged at 1,800 g for 15 minutes at 4° C., and the plasma fractions were transferred and stored under freezing at −30° C. or less until measurement.

(2) Measurement of Plasma Concentrations

The concentrations of the test substances in plasma were measured using LC/MS/MS. Furthermore, as the measurement samples for LC/MS/MS, the supernatants obtained by adding an internal standard substance and acetonitrile in an amount within a range from 5-fold to 10-fold of the amount of the plasma to the collected plasma samples, and removing proteins therefrom, was used.

(3) Calculation of Plasma Concentration of Test Substance at $ED_{50}$ Value

The plasma concentrations of test substances at the $ED_{50}$ values were calculated by deriving a linear regression formula from the administered doses and the plasma concentrations of test substances, by using, among the doses that were actually administered, the values at the time when morphine was administered at the immediate two doses in which the $ED_{50}$ value calculated in Pharmacological Test Example 2 was interposed, and the obtained values were described in Table 3.

TABLE 3

| Example | Plasma concentration of test substance (nM) | Example | Plasma concentration of test substance (nM) | Example | Plasma concentration of test substance (nM) |
|---|---|---|---|---|---|
| 2-(d) | 21.4 | 5-(f) | 7.94 | Comparative Compound 1 | 157 |
| 4-(d) | 48.8 | 6-(e) | 31.6 | | |

Pharmacological Test Example (1) hERG Inhibition Assay

Using hERG (human ether-a-go-go related gene)-transfected HEK293 cells, under a fixed potential, the hERG-derived potassium currents (hereinafter hERG currents) that had passed through the entirety of the cell membrane were measured by the whole-cell patch-clamp method. The effects on the hERG currents were confirmed by the changes in the maximum tail current value that were induced by repolarization pulse. The test conditions were as shown in Table 4.

The suppressive effect on the hERG current in each cell was calculated by a change rate after 10 minutes of application on the maximum tail current at 1 minute after the initiation of the application of the test substances. The hERG inhibition rate was calculated according to the following formula by correcting the suppression rate in each cell with the average suppression rate in a vehicle control (0.1% (v/v) DMSO) group.

hERG inhibition rate (%)=$(A-B)/(100-B) \times 100$

A: the suppression rate (%) of the test substance in each cell

B: the average suppression rate (%) of the vehicle control group

TABLE 4

| Cell line | hERG -transfected HEK293 cells (Wisconsin Alumni Research Foundation) |
|---|---|
| Culture medium | Dulbecco's Modified Eagle's Medium containing 10% of fetal bovine blood serum, 100 U/ml of penicillin, 100 µg/ml of streptomycin and 400 µg/ml of G418 |
| Cells used in tests | The cells were seeded on a collagen-coated cover glass and used within 72 hours. The cells were changed in every application. |
| Application method | Perfusion method |
| Application condition | Perfusion rate: 5 mL/min, temperature: 37.0 ± 1.0° C., application time: 11 min |
| Perfusion solution | 137 mM NaCl, 4 mM KCl, 1.8 mM $CaCl_2$, 1 mM $MgCl_2$, 10 mM D(+)-Glucose, 10 mM HEPES, pH 7.4 |
| Test substance | The DMSO solutions in which the test substances had been dissolved were diluted by 1,000-fold with the perfusion solution (hereinafter referred to as the application solution). Perfusion of the application solution was initiated after the electric current after the depolarization pulse had been provided was stabilized. The concentrations of the test substances were suitably set to be from 4 to 6 doses, and the effects on the hERG currents were evaluated by using two cells per dose. |
| Glass electrode | The glass electrodes having a resistance value of from 2 to 5 MΩ when filled with a glass electrode internal solution were used. |
| Glass electrode internal solution | 130 mM KCl, 1 mM $MgCl_2$ $6H_2O$, 5 mM EGTA, 5 mM MgATP, 10 mM HEPES, pH 7.2 |
| Patch clamp method | The membrane potential was kept at −80 mV, and a depolarization pulse at +20 mV for 0.5 seconds, and a subsequent repolarization pulse at −50 mV for 0.5 seconds were provided at a frequency of once every 15 seconds. |
| Measurement | The hERG current was measured by using an amplifier for patch clamping (Axopatch-200B, Molecular Devices Corporation), and the obtained electrical signal was recorded via recording-analyzing software for patch clamping (pCLAMP 9, Molecular Devices Corporation). |

(2) Calculation of $IC_{50}$ Value

The 50% inhibitory concentration ($IC_{50}$) against the hERG current was calculated by curve fitting program to which Hill equation is applied (KaleidaGraph 3.6, Synergy Software, Pennsylvania, USA) based on the average value of the hERG inhibition rate at the respective doses, and the obtained values were described in Table 5.

TABLE 5

| Example | patch $IC_{50}$ (µM) | Example | patch $IC_{50}$ (µM) | Example | patch $IC_{50}$ (µM) |
|---|---|---|---|---|---|
| 2-(d) | 0.16 | 5-(f) | 0.66 | Comparative compound 1 | 0.30 |
| 4-(d) | 0.58 | 6-(e) | 0.094 | | |

Pharmacological Test Example 5

(1) Mice Serum Protein Binding Assay

The protein binding rate was determined by equilibrium dialysis method using the RED Device (8K MWCO, Rapid Equilibrium Dialysis Device, Thermo Scientific). The test substances that had been dissolved in DMSO were added to the serum that was collected from Cr1: CD-1 (ICR) mice fasted overnight, so that the final concentration of DMSO became 1% (v/v). The serum to which the test substance had been added was added to the inner side of the dialysis membrane of the RED Device, and PBS (phosphate buffer saline, pH 7.4) containing 0.01% (v/v) Tween 80 was added to the outside in accordance with the method for using the RED Device and incubated at 37° C. for 5 to 6 hours with ellipsoidal shaking at 100 rpm so that the concentration of the unbound test substance in the serum and the concentration of the test substance in the PBS reached equilibrium. After the incubation was completed, the respective solutions were collected and stored under freezing at −60° C. or less as measurement samples. The proteins were removed from the measurement sample by adding acetonitrile in an amount of 5-fold or more of the amount of the internal standard substance and the serum sample, and the supernatants were measured by LC/MS/MS (liquid chromatograph-triple quadrupole mass spectrometer). The serum samples were measured after suitably diluting with distilled water as necessary. The protein binding rate was calculated by the following formula by using the ratio of the peak area of the obtained test substance and the peak area of the internal standard substance by LC/MS/MS measurement, and the obtained values were described in Table 6.

Protein binding rate in murine serum (%)=100−($A/B$)×100

A: the peak area of the test substance in the PBS sample/the peak area of the internal standard substance
B: the peak area of the test substance in the serum sample/the peak area of the internal standard substance However, in the case when the concentration in the sample was calculated by using a calibration curve, A and B were as follows.
A: the concentration of the test substance in the PBS sample
B: the concentration of the test substance in the serum sample

TABLE 6

| Example | Protein binding rate (%) | Example | Protein binding rate (%) | Example | Protein binding rate (%) |
|---|---|---|---|---|---|
| 2-(d) | 99.4 | 5-(f) | 96.1 | Comparative compound 1 | 93.2 |
| 4-(d) | 99.4 | 6-(e) | 98.1 | | |

Pharmacological Test Example 6

(1) Safety Margin Against hERG Inhibitory Activity

In order to compare the risks of extension of QT interval prolongation in the electrocardiogram among the test substances, the safety margins against the hERG inhibitory effect were calculated. The safety margin was the gap between the $IC_{50}$ value against the hERG current, which was obtained in Pharmacological Test Example 4, and the unbound drug concentration in plasma at the $ED_{50}$ value in the evaluation of the anti-pruritic effect of the morphine model, which was obtained in Pharmacological Test Example 3. Therefore, the following formula was used for calculating the safety margin, and the obtained values were described in Table 7.

Safety mergin against hERG inhibitory effect=$IC_{50}$×1000/{concentration in plasma×(1−protein binding rate/100)}

$IC_{50}$: the $IC_{50}$ value in a hERG inhibition assay (μM)
Plasma concentration: the plasma concentration of test substance (nM) at the $ED_{50}$ value in the test for evaluating the anti-pruritic effect in the morphine model
Protein binding rate: the protein binding rate (%) in the protein binding assay in murine serum As a result, it was found that most of the compounds which were tested at this time had a broad safety margin.

The compounds used in this study were different from the present invention in salt or crystalline from, but the values of "safety margin against hERG inhibitory activity" are the same although the salt or crystalline form is different. This is because "$IC_{50}$", "concentration in plasma", and "protein binding rate" used in the above formula to calculate "safety margin against hERG inhibitory activity" become the same despite of the differences in the salt or crystalline form.

That is, difference in salt or crystalline form may lead to different bioavailability when a compound is administered in vivo, and therefore the administration volume to exert the same pharmacological effect may be different, but drug efficacy is explained by drug concentration in plasma, so the drug concentrations in plasma at $ED_{50}$ value become the same even though the salt or crystalline form is different. Also, values of $IC_{50}$ and protein binding rate become the same although the salt or crystalline form of the compound is different because they were calculated by conducting tests using a solution in which the compound is dissolved in DMSO.

TABLE 7

| Example | Safety margin | Example | Safety margin | Example | Safety margin |
|---|---|---|---|---|---|
| 2-(d) | 1250 | 5-(f) | 2130 | Comparative Compound 1 | 28 |
| 4-(d) | 1980 | 6-(e) | 157 | | |

INDUSTRIAL APPLICABILITY

The compounds (I) have a μ-opioid receptor antagonistic activity, and are useful as an agent for preventing or treating diseases in which pruritus is the therapeutic target. In addition, the crystal of the salt of the compounds (I) of the present invention has great properties (including stability and solubility). Therefore, the crystal of the salt of the compounds (I) of the present invention is highly suitable for using as a medicine to prevent or treat diseases in which pruritus is the therapeutic target.

The invention claimed is:

1. A crystal of a salt comprising: a compound represented by a formula (I)

(I)

wherein $R^2$ is a hydrogen atom or a halogen atom, and $R^1$ is a group selected from the group consisting of

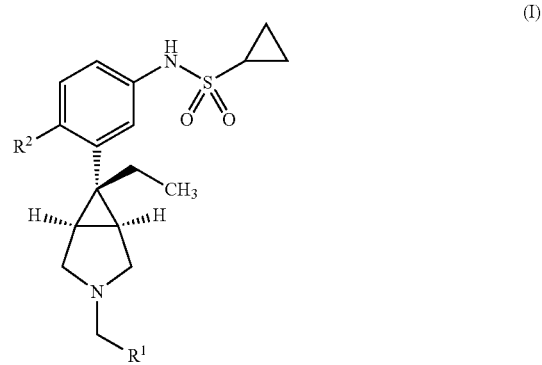

-continued

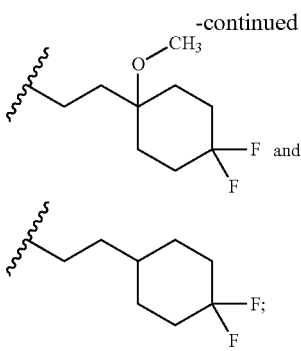

and an acid selected from the group consisting of hydrochloric acid, hydrobromic acid, and oxalic acid.

2. The crystal of a salt of claim 1, wherein the salt is N-(3{(1R,5S,6r)-6-ethyl-3-[(2-hydroxy-2,3-dihydro-1H-inden-2-yl)methyl]-3-azabicyclo[3.1.0]hexan-6-yl}-4-fluorophenyl)cyclopropanesulfonamide hydrochloride.

3. The crystal according to claim 2, which has a diffraction peak(s) at a diffraction angle(s) (2θ±0.2°) of 8.3°, 13.6°, 17.4°, and 24.3° in powder X-ray diffraction.

4. The crystal of a salt of claim 1, wherein the salt is N-(3{(1R,5S,6r)-6-ethyl-3-[2-hydroxy-2,3-dihydro-1H-inden-2-yl)methyl]-3-azabicyclo[3.1.0]hexan-6-yl}-4-fluorophenyl)cyclopropanesulfonamide hydrobromide.

5. The crystal according to claim 4, which has a diffraction peak(s) at a diffraction angle(s) (2θ±0.2°) of 9.1° 14.1°, 17.3°, and 24.2° in powder X-ray diffraction.

6. The crystal of a salt of claim 1, wherein the salt is N-(3-{(1R,5S,6r)-3-[3-(4,4-difluoro-1-methoxycyclohexyl)propyl]-6-ethyl-3-azabicyclo[3.1.0]hexan-6-yl}phenyl)cyclopropanesulfonamide hydrochloride.

7. The crystal according to claim 6, which has a diffraction peak(s) at a diffraction angle(s) (2θ±0.2°) of 8.6°, 16.2°, 23.9°, and 27.4° in powder X-ray diffraction.

8. The crystal of a salt of claim 1, wherein the salt is N-(3-{(1R,5S,6r)-3-[3-(4,4-difluoro-1-methoxycyclohexyl)propyl]-6-ethyl-3-azabicyclo[3.1.0]hexan-6-yl}phenyl)cyclopropanesulfonamide oxalate.

9. The crystal according to claim 8, which has a diffraction peak(s) at a diffraction angle(s) (2θ±0.2°) of 9.5°, 10.3°, 23.8°, and 25.1° in powder X-ray diffraction.

10. The crystal of a salt of claim 1, wherein the salt is N-(3-{(1R,5S,6r)-3-[3-(4,4-difluorocyclohexyl)propyl]-6-ethyl-3-azabicyclo[3.1.0]hexan-6-yl}phenyl)cyclopropanesulfonamide hydrobromide.

11. The crystal according to claim 10, which has a diffraction peak(s) at a diffraction angle(s) (2θ±0.2°) of 9.1°, 14.5°, 17.1°, and 25.2° in powder X-ray diffraction.

12. The crystal of a salt of claim 1, wherein the salt is N-(3-{(1R,5S,6r)-3-[3-(4,4-difluorocyclohexyl)propyl]-6-ethyl-3-azabicyclo[3.1.0]hexan-6-yl}phenyl)cyclopropanesulfonamide oxalate.

13. The crystal according to claim 12, which has a diffraction peak(s) at a diffraction angle(s) (2θ±0.2°) of 9.7°, 14.5°, 17.3°, and 26.0° in powder X-ray diffraction.

14. A pharmaceutical composition comprising the crystal according to claim 1 as an active ingredient.

15. The crystal according to claim 2, which has a diffraction peak(s) at a d-spacing(s) of 10.6 Å, 6.50 Å, 5.09 Å, and 3.66 Å in powder X-ray diffraction.

16. The crystal according to claim 2, which has absorption peaks at wave numbers ($v_{max}$±18 cm$^{-1}$) of 737 cm$^{-1}$, 800 cm$^{-1}$, 1150 cm$^{-1}$, 1466 cm$^{-1}$, and 3219 cm$^{-1}$ in its infrared absorption spectrum.

17. The crystal according to claim 4, which has a diffraction peak(s) at a d-spacing(s) of 9.71 Å, 6.27 Å, 5.12 Å, and 3.67 Å in powder X-ray diffraction.

18. The crystal according to claim 4, which has absorption peaks at wave numbers ($v_{max}$±18 cm) of 737 cm$^{-1}$, 797 cm$^{-1}$, 1148 cm$^{-1}$, 1460 cm$^{-1}$, and 3277 cm$^{-1}$ in its infrared absorption spectrum.

19. The crystal according to claim 6, which has a diffraction peak(s) at a d-spacing(s) of 10.3 Å, 5.46 Å, 3.72 Å, and 3.25 Å in powder X-ray diffraction.

20. The crystal according to claim 6, which has absorption peaks at wave numbers ($v_{max}$±18 cm$^{-1}$) of 706 cm$^{-1}$, 1148 cm$^{-1}$, 1477 cm$^{-1}$, 1607 cm$^{-1}$, and 2941 cm$^{-1}$ in its infrared absorption spectrum.

21. The crystal according to claim 8, which has a diffraction peak(s) at a d-spacing(s) of a 9.30 Å, 8.58 Å, 3.73 Å, and 3.54 Å in powder X-ray diffraction.

22. The crystal according to claim 8, which has absorption peaks at wave numbers ($v_{max}$±18 cm$^{-1}$) of 712 cm$^{-1}$, 1157 cm$^{-1}$, 1458 cm$^{-1}$, 1607 cm$^{-1}$, and 3254 cm$^{-1}$ its infrared absorption spectrum.

23. The crystal according to claim 10, which has a diffraction peak(s) at a d-spacing(s) of 9.71 Å, 6.10 Å, 5.18 Å, and 3.53 Å in powder X-ray diffraction.

24. The crystal according to claim 10, which has absorption peaks at wave numbers ($v_{max}$±18 cm$^{-1}$) of 733 cm$^{-1}$, 889 cm$^{-1}$, 1152 cm$^{-1}$, 1605 cm$^{-1}$, and 3071 cm$^{-1}$ in its infrared absorption spectrum.

25. The crystal according to claim 12, which has a diffraction peak(s) at a d-spacing(s) of 9.11 Å, 6.10 Å, 5.12 Å, and 3.42 Å; in powder X-ray diffraction.

26. The crystal according to claim 12, which has absorption peaks at wave numbers ($v_{max}$±18 cm$^{-1}$) of 704 cm$^{-1}$, 889 cm$^{-1}$, 1152 cm$^{-1}$, 1609 cm$^{-1}$, and 3244 cm$^{-1}$ in its infrared absorption spectrum.

* * * * *